United States Patent
Nakagawa et al.

[11] Patent Number: 5,095,013
[45] Date of Patent: Mar. 10, 1992

[54] 2-(2-VINYLPYRROLIDINYLTHIO)CARBAPENEM DERIVATIVES

[75] Inventors: Susumu Nakagawa; Fumio Nakano; Norikazu Otake; Ryosuke Ushijima, all of Okazaki, Japan

[73] Assignee: Banyu Pharmaceutical Co., Ltd., Tokyo, Japan

[21] Appl. No.: 562,564

[22] Filed: Aug. 3, 1990

[30] Foreign Application Priority Data
Aug. 4, 1989 [JP] Japan ................... 1-202568

[51] Int. Cl.$^5$ .................... C07D 487/04; A61K 31/40
[52] U.S. Cl. ...................... 514/210; 540/350
[58] Field of Search ................ 540/350; 514/210

[56] References Cited

U.S. PATENT DOCUMENTS
4,921,852  5/1990  Murata ................. 514/210
4,925,838  5/1990  Murata ................. 514/210

FOREIGN PATENT DOCUMENTS
0182213  5/1986  European Pat. Off.
0243686  11/1987 European Pat. Off.

Primary Examiner—Robert Gerstl
Attorney, Agent, or Firm—Oblon, Spivak, McClelland, Maier & Neustadt

[57] ABSTRACT

A compound of the formula:

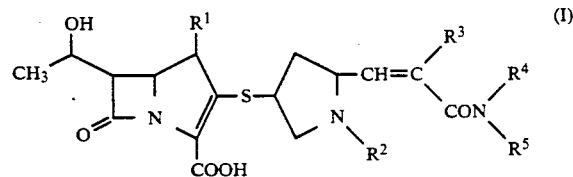

wherein $R^1$ is a hydrogen atom or a methyl group, $R^2$ is a hydrogen atom or a lower alkyl group, each of $R^3$, $R^4$ and $R^5$ is a hydrogen atom or a lower alkyl group, or $R^3$ and $R^4$ together form a methylene group, an ethylene group or a propylene group, or $R^4$ and $R^5$ form together with the adjacent nitrogen atom an aziridinyl group, an azetidinyl group, a pyrrolidinyl group, a piperidino group, a piperazinyl group or a morpholino group; or a pharmaceutically acceptable salt or ester thereof.

11 Claims, No Drawings

2-(2-VINYLPYRROLIDINYLTHIO)CARBAPENEM DERIVATIVES

The present invention relates to novel carbapenem (7-oxo-1-azabicyclo[3.2.0]hept-2-ene-2-carboxylic acid) compounds, and antibacterial agents containing such compounds as active ingredients, and processes for producing such compounds.

In recent years, new β-lactam antibiotic substances have been found in nature which have the same β-lactam rings as penicillin derivatives and as cephalosporin derivatives, but which have different basic structures.

For example, naturally derived carbapenem compounds such as thienamycin were isolated from the fermentation of Streptomyces cattleya (J. Am. Chem. Soc., vol. 100, p.6491 (1978)). Thienamycin has an excellent antibacterial spectrum and strong antibacterial activities over a wide range against gram positive bacteria and gram negative bacteria. Therefore, its development as a highly useful β-lactam agent has been expected. However, thienamycin itself is chemically unstable, and it has been reported that it is likely to be decomposed by a certain enzyme in vivo such as renal dehydropeptidase I (hereinafter referred to simply as DHP-I), whereby the antibacterial activities tend to decrease, and the recovery rate in the urine is low (Antimicrob. Agents Chemother., vol. 22, p.62 (1982); ditto, vol. 23, p.300 (1983)).

Merck & Co. Inc. have synthesized many thienamycin analogues with an aim to maintain the excellent antibacterial activities of thienamycin and to secure chemical stability. As a result, imipenem obtained by formimidation of the amino group of thienamycin, has been practically developed as a pharmaceutical product (J. Med. Chem., vol. 22, p. 1435 (1979)). Imipenem has antibacterial activities of an equal or higher level than thienamycin against various types of bacteria and has β-lactamase resistance. Especially against Pseudomonas aeruqinosa, its antibacterial activities are superior to thienamycin by from 2 to 4 times. Further, the stability of imipenem in the solid form or in an aqueous solution is remarkably improved over thienamycin.

However, like thienamycin, imipenem is likely to be decomposed by DHP-I in the human kidney. Therefore, it can not be used for treatment of the infectiousness of the genito-urinary tract. Further, it presents toxicity against the kidney due to the decomposition products. Therefore, imipenem can not be administered alone and is required to be used in combination with a DHP-I inhibitor like cilastatin (Antimicrob. Agents Chemother., vol 12 (Suppl. D), p. 1 (1983)). In recent years, imipenem has been frequently used for the treatment and prevention of infectious diseases. Consequently, highly methicillin resistant Staphylococcus aureus which is resistant to imipenem and imipenem resistant Pseudomonas aeruginosa are increasing in the clinical field. Imipenem does not show adequate treating effects against these resistant bacteria.

As the prior art closest to the present invention, Japanese Examined Patent Publication No. 55514/1988 may be mentioned. This publication discloses carbapenem compounds having a 2-(aminocarbonyl or N-mono- or N,N-di-lower alkylaminocarbonyl)pyrrolidin-4-ylthio group at the 2-position of the carbapenem structure, represented by meropenem, SM-7338, as a typical compound.

β-Lactam antibiotics exhibit selective toxicity against bacteria and show no substantial effects against animal cells. Therefore, they are widely used for treatment of infectious diseases caused by bacteria, as rare antibiotics having no side effects, and thus are highly useful drugs.

However, in recent years, highly methicillin resistant Staphylococcus aureus and resistant Pseudomonas aeruginosa have been isolated frequently from patients with the immunity decreased, as bacteria causing hardly curable infectious diseases. This is regarded as a clinically serious problem. Accordingly, it is strongly desired to develop an antibacterial agent having improved antibacterial activities against such resistant bacteria Especially with respect to carbapenem compounds, it is desired to improve the antibacterial activities, to improve the stability against DHP-I, to reduce the toxicity against the kidney and to reduce side effects against the central nerve.

The compounds disclosed in Japanese Examined Patent Publication No. 55514/1988, particularly meropenem, have the stability against DHP-I substantially improved. However, the antibacterial activities against the above-mentioned highly methicillin resistant Staphylococcus aureus are not adequate, and a carbapenem compound having superior antibacterial activities, is desired.

The carbapenem compounds having a 2-[2-(N-unsubstituted, N-substituted or N,N-disubstituted aminocarbonyl)vinyl]pyrrolidin-4-ylthio group at the 2-position of the carbapenem structure, as a feature of the present invention, are novel compounds, which have never been disclosed or suggested in any literatures or patent specifications.

The present inventors have made extensive researches with an aim to provide novel carbapenem compounds having excellent antibacterial activities particularly against highly methicillin resistant Staphylococcus aureus, which are resistant against DHP-I. As a result, they have found that novel carbapenem compounds having a 2-[2-(N-unsubstituted, N-substituted or N,N-disubstituted aminocarbonyl)vinyl]pyrrolidin-4-ylthio group at the 2-position of the carbapenem structure, have strong antibacterial activities against gram positive bacteria such as Staphylococcus aureus and against gram negative bacteria including Pseudomonas aeruginosa and further exhibit excellent stability against DHP-I. The present invention has been accomplished on the basis of this discovery.

The present invention provides a compound of the formula:

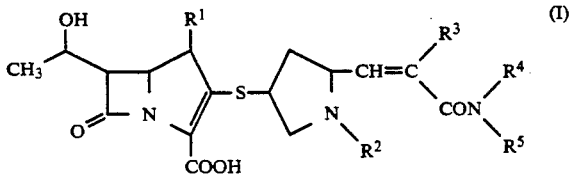

wherein $R^1$ is a hydrogen atom or a methyl group, $R^2$ is a hydrogen atom or a lower alkyl group, each of $R^3$, $R^4$ and $R^5$ is a hydrogen atom or a lower alkyl group, or $R^3$ and $R^4$ together form a methylene group, an ethylene group or a propylene group, or $R^4$ and $R^5$ form together with the adjacent nitrogen atom an aziridinyl group, an azetidinyl group, a pyrrolidinyl group, a piperidino group, a piperazinyl group or a morpholino group; or a pharmaceutically acceptable salt or ester thereof.

The present invention also provides a process for producing the compound of the formula (I) or a pharmaceutically acceptable salt or ester thereof, which comprises reacting a compound of the formula:

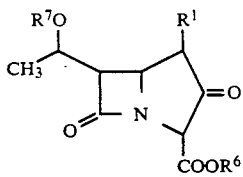
(II)

wherein $R^1$ is as defined above, $R^6$ is a hydrogen atom or a carboxyl-protecting group, and $R^7$ is a hydrogen atom or a hydroxyl-protecting group, or a reactive derivative thereof, with a compound of the formula:

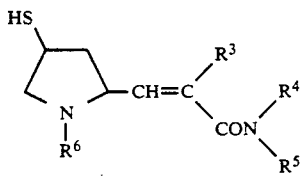
(III)

wherein $R^3$, $R^4$ and $R^5$ are as defined above, and $R^8$ is a hydrogen atom or an imino-protecting group, to obtain a compound of the formula:

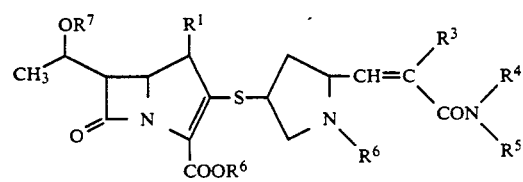
(IV)

wherein $R^1$, $R^3$, $R^4$, $R^5$, $R^6$, $R^8$ and $R^8$ are as defined above, and if necessary, removing any protecting group.

The present invention further provides a process for producing the compound of the formula (I) or a pharmaceutically acceptable salt or ester thereof, which comprises reacting an oxidizing agent to a compound of the formula:

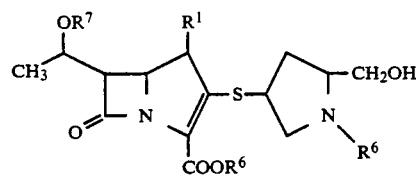
(V)

wherein $R^1$ is as defined above, $R^6$ is a hydrogen atom or a carboxyl-protecting group, $R^7$ is a hydrogen atom or a hydroxyl-protecting group, and $R^8$ is a hydrogen atom or an imino-protecting group, to obtain a compound of the formula:

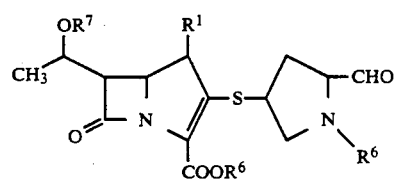
(VI)

wherein $R^1$, $R^6$, $R^7$ and $R^8$ are as defined above, reacting the compound of the formula (VI) with a compound of the formula:

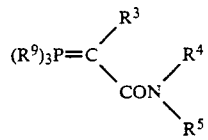
(VII-a)

or

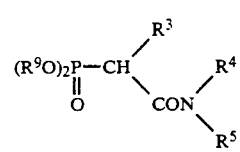
(VII-b)

wherein $R^3$, $R^4$ and $R^5$ are as defined above, and $R^9$ is a methyl group, an ethyl group, an isopropyl group, a 2,2,2-trifluoroethyl group or a phenyl group, to obtain a compound of the formula:

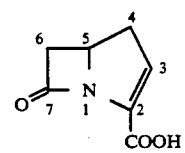
(IV)

wherein $R^1$, $R^3$, $R^4$, $R^5$, $R^6$, $R^7$ and $R^8$ are as defined above, and if necessary, removing any protecting group.

Further, the present invention provides an antibacterial agent comprising an antibacterially effective amount of the compound of the formula (I) or a pharmaceutically acceptable salt or ester thereof, and a pharmaceutically acceptable carrier or diluent.

Now, the present invention will be described in detail with reference to the preferred embodiments. Firstly, the symbols and terms used in this specification will be explained.

The compound of the present invention has a basic structure of the formula:

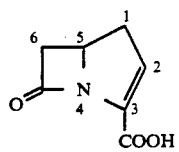

which is systematically referred to as a 7-oxo-1-azabicyclo[3.2.0]hept-2-ene-2-carboxylic acid. For the convenience sake, in this specification, this basic structure will be referred to as a 1-carbapen-2-em-3-carboxylic acid by putting the numbers based on a commonly widely used carbapenem of the formula:

The present invention includes optical isomers based on the asymmetrical carbon atoms at the 1-position, 5-position, 6-position and 8-position of the carbapenem structure. Among these isomers, preferred is a compound of a (5R,6S,8R) configuration i.e. a compound having a steric configuration of (5R,6S) (5,6-trans) like thienamycin and in which the carbon atom at the 8-position takes a R-configuration, or a compound of a (1R,5S,6S,8R) configuration in a case where a methyl group is present at the 1-position.

The 2'-[2-(N-unsubstituted, N-substituted or N,N-disubstituted aminocarbonyl)vinyl]pyrrolidin-4'-ylthio group at the 2-position of the carbapenem structure also includes isomers based on the asymmetrical carbon atoms at the 2- and 4-positions of the pyrrolidine structure. Among these isomers, preferred are compounds of a (2'S,4'S) configuration and a (2'R,4'R) configuration.

Accordingly, among compounds of the formula (I), a group of compounds having preferred steric configurations are represented by the formula (I-a):

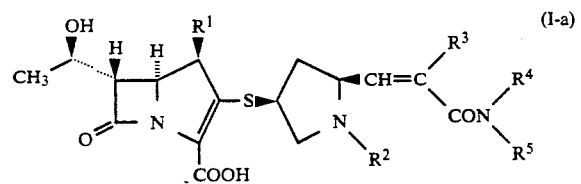

wherein $R^1$, $R^2$, $R^3$, $R^4$ and $R^5$ are as defined above.

Among the compounds of the formula (I-a), a group of compounds wherein $R^3$ and $R^4$ together form a methylene group, an ethylene group or a propylene group and a group of compounds wherein at least one of $R^4$ and $R^5$ is a hydrogen atom, have particularly excellent antibacterial activities.

Further, with respect to the double bond of the 2-(N-unsubstituted, N-substituted or N,N-di-substituted aminocarbonyl)vinyl group, cis(Z) and trans(E) geometrical isomers are present. These isomers are also included in the present invention. Of these isomers, the (E)-isomer has particularly excellent antibacterial activities.

The lower alkyl group means a linear or branched alkyl group having from 1 to 6 carbon atoms, preferably from 1 to 4 carbon atoms. Particularly preferred are a methyl group, an ethyl group and a tert-butyl group.

The carboxyl-protecting group may, for example, be a lower alkyl group such as a methyl group, an ethyl group, a propyl group, an isopropyl group or a tert-butyl group; a halogenated lower alkyl group such as a 2,2,2-trichloroethyl group or a 2,2,2-trifluoroethyl group; a lower alkanoyloxyalkyl group such as an acetoxymethyl group, a propionyloxymethyl group, a pivaloyloxymethyl group, a 1-acetoxyethyl group or a 1-propionyloxyethyl group; a lower alkoxycarbonyloxyalkyl group such as a 1-(methoxycarbonyloxy)ethyl group, a 1-(ethoxycarbonyloxy)ethyl group or a 1-(isopropoxycarbonyloxy)ethyl group; a lower alkenyl group such as a 2-propenyl group, a 2-chloro-2-propenyl group, a 3-methoxycarbonyl-2-propenyl group, a 2-methyl-2-propenyl group, a 2-butenyl group or a cinnamyl group; an aralkyl group such as a benzyl group, a p-methoxybenzyl group, a 3,4-dimethoxybenzyl group, an o-nitrobenzyl group, a p-nitrobenzyl group, a benzhydryl group or a bis(p-methoxyphenyl)methyl group; a (5-substituted 2-oxo-1,3-dioxol-4-yl)methyl group such as a (5-methyl-2-oxo-1,3-dioxol 4-yl)methyl group; a lower alkylsilyl group such as a trimethylsilyl group or a tertbutyldimethylsilyl group; an indanyl group, a phthalidyl group or a methoxymethyl group. Particularly preferred are a 2-propenyl group, a p-nitrobenzyl group, a p-methoxybenzyl group, a benzhydryl group and a tertbutyldimethylsilyl group.

The hydroxyl-protecting group may, for example, be a lower alkylsilyl group such as a trimethylsilyl group or a tert-butyldimethylsilyl group; a lower alkoxymethyl group such as a methoxymethyl group or a 2-methoxyethoxymethyl group; a tetrahydropyranyl group; an aralkyl group such as a benzyl group, a p-methoxybenzyl group, a 2,4-dimethoxybenzyl group, an o-nitrobenzyl group, a p-nitrobenzyl group or a trityl group; an acyl group such as a formyl group or an acetyl group; a lower alkoxycarbonyl group such as a tert-butoxycarbonyl group, a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; or an aralkyloxycarbonyl group such as a benzyloxycarbonyl group, a p-methoxybenzyloxycarbonyl group, an o-nitrobenzyloxycarbonyl group or a p-nitrobenzyloxycarbonyl group. Particularly preferred are a 2-propenyloxycarbonyl group, a p-nitrobenzyloxycarbonyl group and a tert-butyldimethylsilyl group.

The imino-protecting group may, for example, be an aralkyl group such as a benzyl group, a p-methoxybenzyl group, a 3,4-dimethoxybenzyl group, an o-nitrobenzyl group, a p-nitrobenzyl group, a benzhydryl group or a bis(p-methoxyphenyl)methyl group; a lower alkanoyl group such as a formyl group, an acetyl group, a propionyl group, a butyryl group, an oxalyl group, a succinyl group or a pivaloyl group; a halogenated lower alkanoyl group such as a chloroacetyl group, a dichloroacetyl group, a trichloroacetyl group or a trifluoroacetyl group; an arylalkanoyl group such as a phenylacetyl group or a phenoxyacetyl group; a lower alkoxycarbonyl group such as a methoxycarbonyl group, an ethoxycarbonyl group, a propoxycarbonyl group or a tert-butoxycarbonyl group; a halogenated lower alkoxycarbonyl group such as a 2-iodoethoxycarbonyl group or a 2,2,2-trichloroethoxycarbonyl group; an alkenyloxycarbonyl group such as a 2-propenyloxycarbonyl group, a 2-chloro-2-propenyloxycarbonyl group, a 3-methoxycarbonyl-2-propenyloxycarbonyl group, a 2-methyl-2-propenyloxycarbonyl group, a 2-butenyloxycarbonyl group or a cinnamyloxycarbonyl group; an aralkyloxycarbonyl group such as a benzyloxycarbonyl group, an o-nitrobenzyloxycarbonyl group, a p-nitrobenzyloxycarbonyl group or a phenethyloxycarbonyl group; or a lower alkylsilyl group such as a trimethylsilyl group or a tert-butyldimethylsilyl group. Particularly preferred are a 2-propenyloxycarbonyl group, a tert butoxycarbonyl group and a p-nitrobenzyloxycarbonyl group.

The meanings of abbreviations used in this specification are as follows:
Ac: acetyl group
Me: methyl group
Ms: methanesulfonyl group
PMB: p-methoxybenzyl group
Tr: trityl group
Et: ethyl group tBu: tert-butyl group
Pr: propyl group
Preferred examples of the compound of the formula (I) will be given in the following Table.
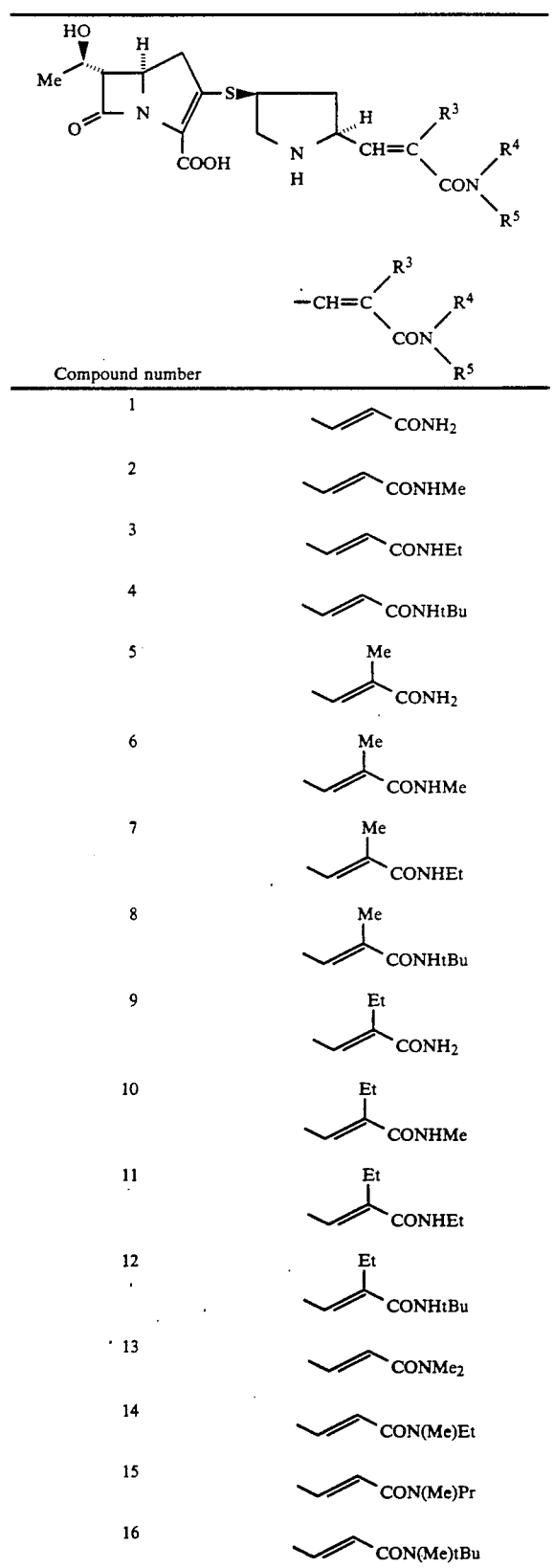
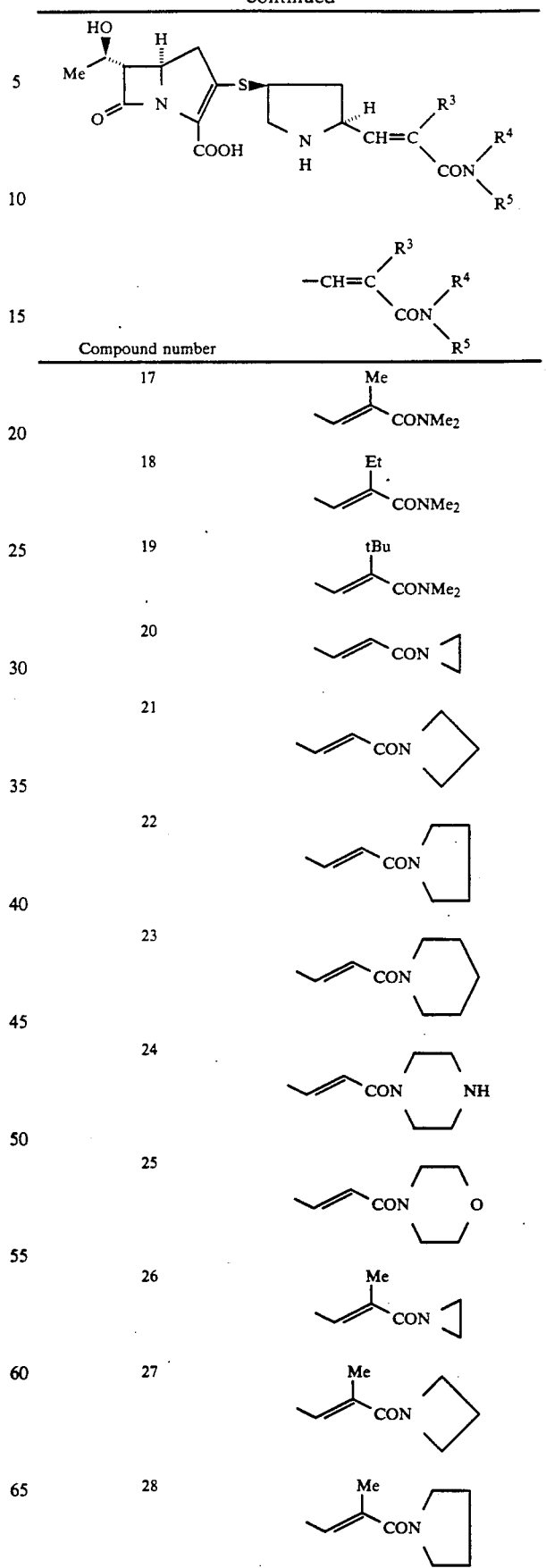

-continued
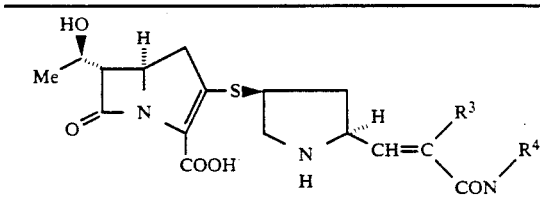
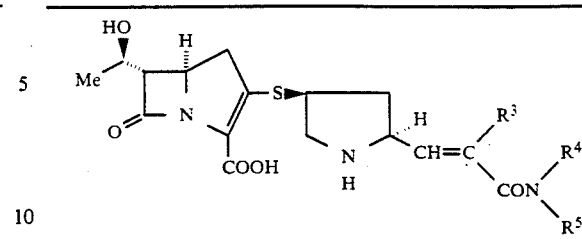
| Compound number | | Compound number | |
|---|---|---|---|
| 2 | 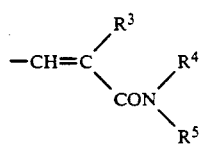 | 38 | 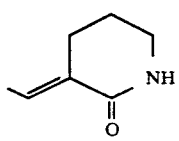 |
| 30 | 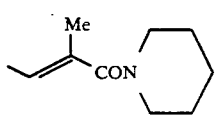 | 39 | 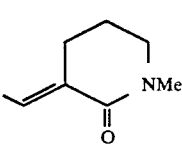 |
| 31 | 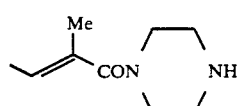 | 40 | 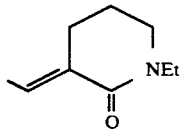 |
| 32 | 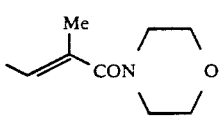 | 41 | 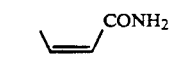 CONH$_2$ |
| 33 | 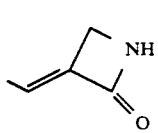 | 42 | 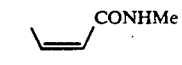 CONHMe |
| 34 | 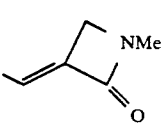 | 43 | 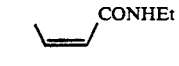 CONHEt |
| 35 | 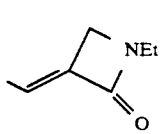 | 44 | 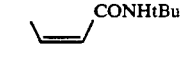 CONHtBu |
| 36 | 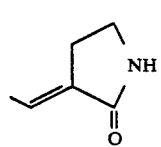 | 45 | 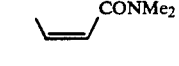 CONMe$_2$ |
| | | 46 | 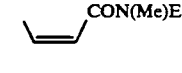 CON(Me)Et |
| | | 47 | 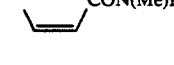 CON(Me)Pr |
| | | 48 | 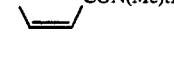 CON(Me)tBu |
| 37 | 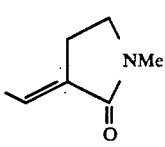 | 49 | 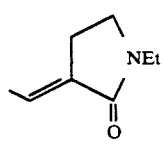 |
| | | 50 | 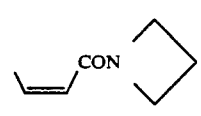 |

-continued
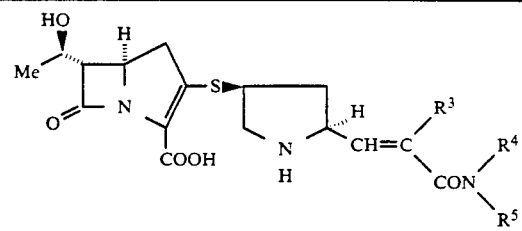
$$-CH=C\begin{matrix}R^3\\\\CON\begin{matrix}R^4\\R^5\end{matrix}\end{matrix}$$
| Compound number | |
|---|---|
| 51 | 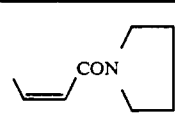 |
| 52 | 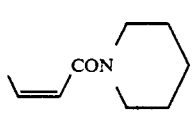 |
| 53 | 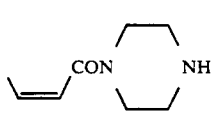 |
| 54 | 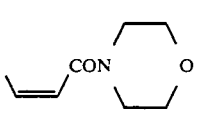 |
| 55 | 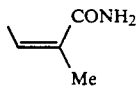 |
| 56 | 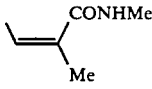 |
| 57 | 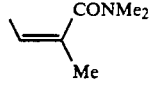 |
| 58 | 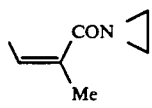 |
| 59 | 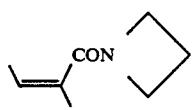 |
| 60 | 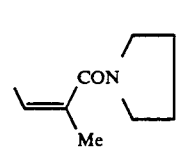 |
-continued
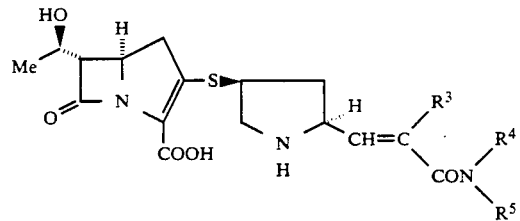
$$-CH=C\begin{matrix}R^3\\\\CON\begin{matrix}R^4\\R^5\end{matrix}\end{matrix}$$
| Compound number | |
|---|---|
| 61 | 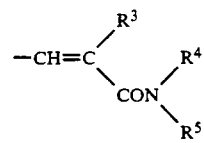 |
| 62 | 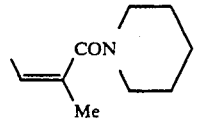 |
| 63 | 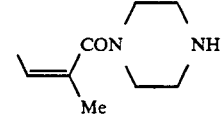 |
| 64 | 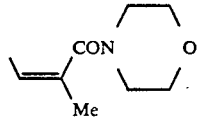 |
| 65 | 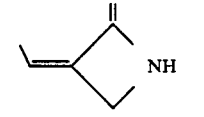 |
| 66 | 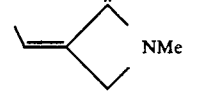 |
| 67 | 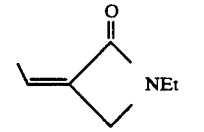 |
| 68 | 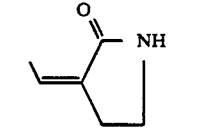 |
| 69 | 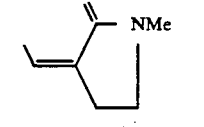 |
|  | 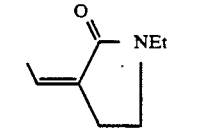 |

-continued

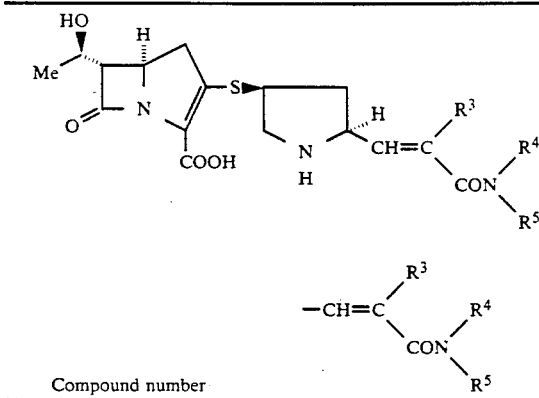

| Compound number | |
|---|---|
| 70 | 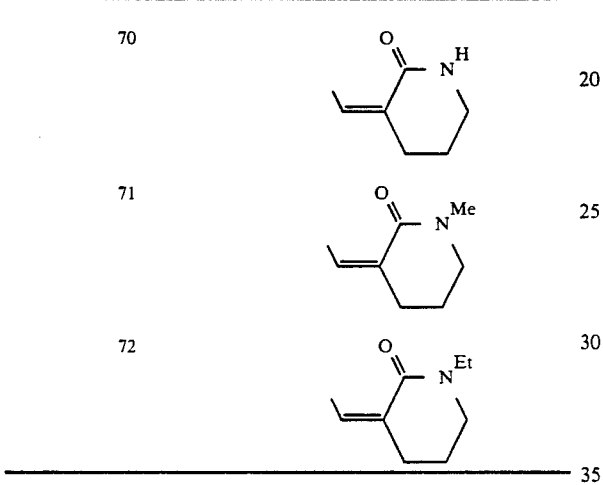 |
| 71 | |
| 72 | |

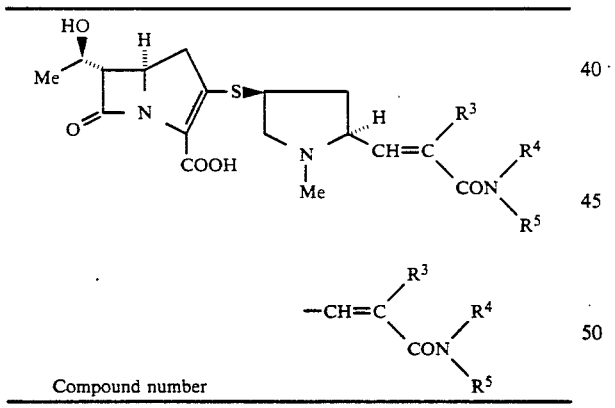

| Compound number | |
|---|---|
| 73 | CONH₂ |
| 74 | CONHMe |
| 75 | CONHEt |
| 76 | CONHtBu |
| 77 | $\overset{Me}{\diagdown}$ CONH₂ |

-continued

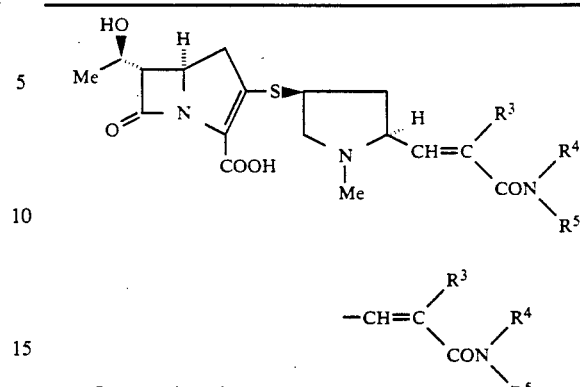

| Compound number | |
|---|---|
| 78 | $\overset{Me}{\diagdown}$ CONHMe |
| 79 | $\overset{Me}{\diagdown}$ CONHEt |
| 80 | $\overset{Me}{\diagdown}$ CONHtBu |
| 81 | $\overset{Et}{\diagdown}$ CONH₂ |
| 82 | $\overset{Et}{\diagdown}$ CONHMe |
| 83 | $\overset{Et}{\diagdown}$ CONHEt |
| 84 | $\overset{Et}{\diagdown}$ CONHtBu |
| 85 | CONMe₂ |
| 86 | CON(Me)Et |
| 87 | CON(Me)Pr |
| 88 | CON(Me)tBu |
| 89 | $\overset{Me}{\diagdown}$ CONMe₂ |
| 90 | $\overset{Et}{\diagdown}$ CONMe₂ |
| 91 | $\overset{tBu}{\diagdown}$ CONMe₂ |
| 92 | CON⟨ |

-continued
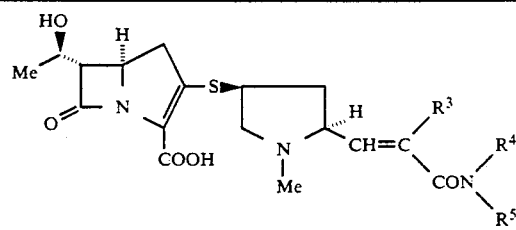
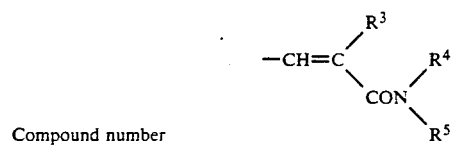
| Compound number | |
|---|---|
| 93 | 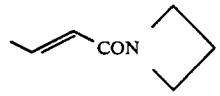 |
| 94 | 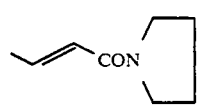 |
| 95 | 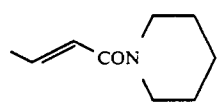 |
| 96 | 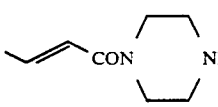 |
| 97 | 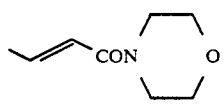 |
| 98 | 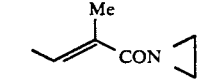 |
| 99 | 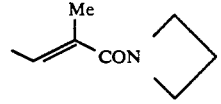 |
| 100 | 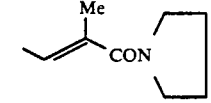 |
| 101 | 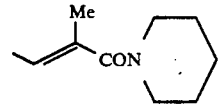 |
| 102 | 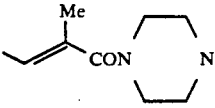 |
-continued
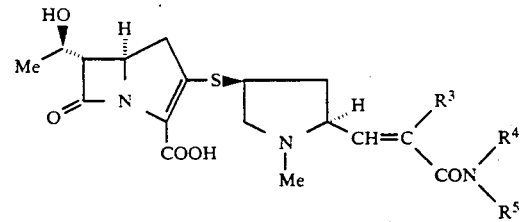
| Compound number | |
|---|---|
| 103 | 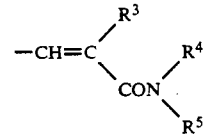 |
| 104 | 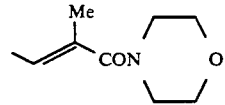 |
| 105 | 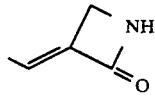 |
| 106 | 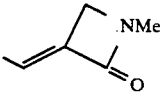 |
| 107 | 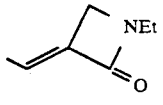 |
| 108 | 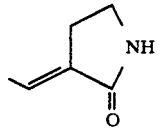 |
| 109 | 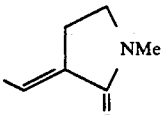 |
| 110 | 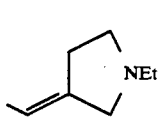 |
| 111 | 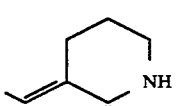 |

-continued

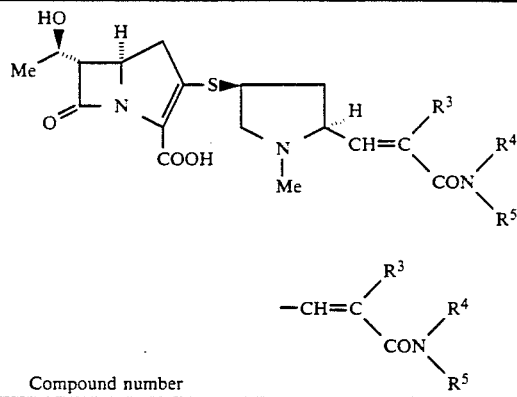

| Compound number | |
|---|---|
| 112 | ethylidene-piperidone with NEt |
| 113 | CH=CH-CONH₂ |
| 114 | CH=CH-CONHMe |
| 115 | CH=CH-CONHEt |
| 116 | CH=CH-CONHtBu |
| 117 | CH=CH-CONMe₂ |
| 118 | CH=CH-CON(Me)Et |
| 119 | CH=CH-CON(Me)Pr |
| 120 | CH=CH-CON(Me)tBu |
| 121 | CH=CH-CON(aziridine) |
| 122 | CH=CH-CON(azetidine) |
| 123 | CH=CH-CON(pyrrolidine) |
| 124 | CH=CH-CON(piperidine) |
| 125 | CH=CH-CON(piperazine NH) |

-continued

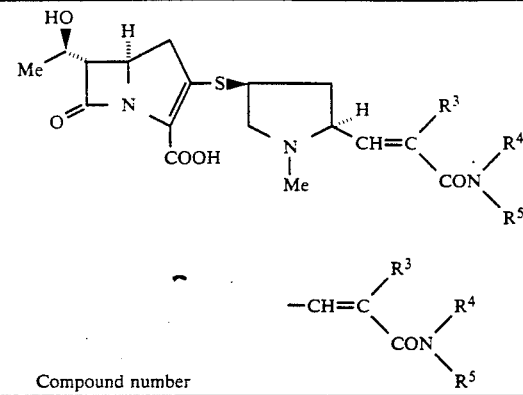

| Compound number | |
|---|---|
| 126 | CH=CH-CON(morpholine) |
| 127 | CH=C(Me)-CONH₂ |
| 128 | CH=C(Me)-CONHMe |
| 129 | CH=C(Me)-CONMe₂ |
| 130 | CH=C(Me)-CON(aziridine) |
| 131 | CH=C(Me)-CON(azetidine) |
| 132 | CH=C(Me)-CON(pyrrolidine) |
| 133 | CH=C(Me)-CON(piperidine) |
| 134 | CH=C(Me)-CON(piperazine NH) |
| 135 | CH=C(Me)-CON(morpholine) |

-continued
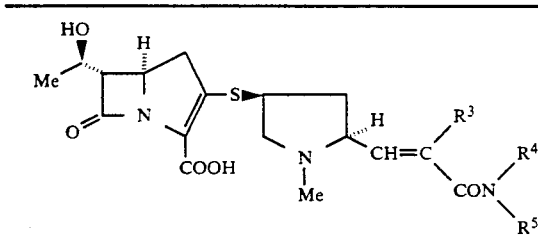
| Compound number | $-CH=C \begin{matrix} R^3 \\ CON \begin{matrix} R^4 \\ R^5 \end{matrix} \end{matrix}$ |
|---|---|
| 136 | 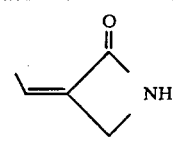 |
| 137 | 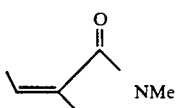 |
| 138 | 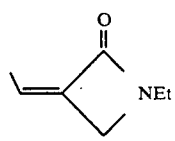 |
| 139 | 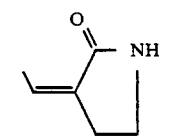 |
| 140 | 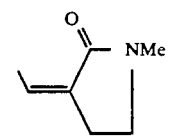 |
| 141 | 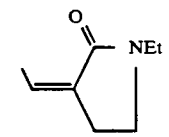 |
| 142 | 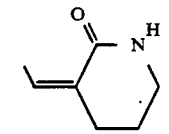 |
| 143 | 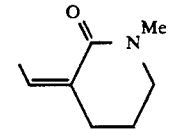 |
-continued
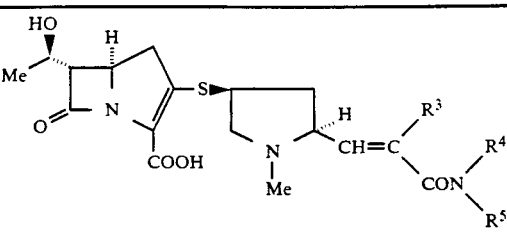
| Compound number | $-CH=C \begin{matrix} R^3 \\ CON \begin{matrix} R^4 \\ R^5 \end{matrix} \end{matrix}$ |
|---|---|
| 144 | 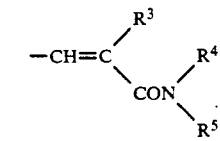 |
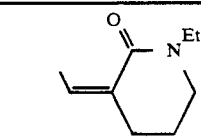
| Compound number | $-CH=C \begin{matrix} R^3 \\ CON \begin{matrix} R^4 \\ R^5 \end{matrix} \end{matrix}$ |
|---|---|
| 145 | 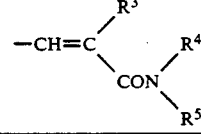 |
| 146 | 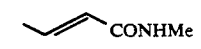 |
| 147 | 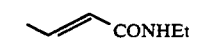 |
| 148 | 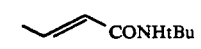 |
| 149 |  |
| 150 |  |
| 151 | 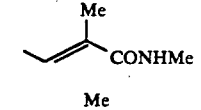 |
| 152 | 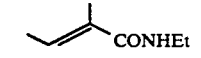 |
| 153 | 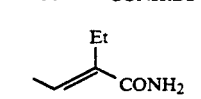 |

-continued
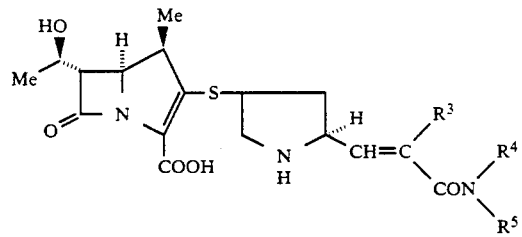
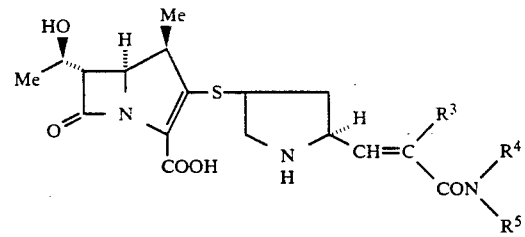
| Compound number | -CH=C(R³)CONR⁴R⁵ |
|---|---|
| 154 | 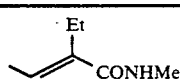 |
| 155 | 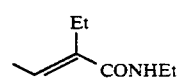 |
| 156 | 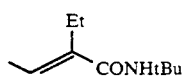 |
| 157 | 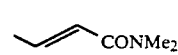 |
| 158 | 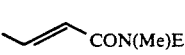 |
| 159 | 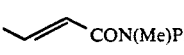 |
| 160 |  |
| 161 | 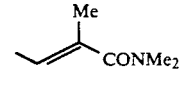 |
| 162 | 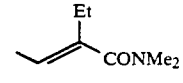 |
| 163 | 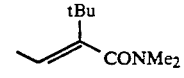 |
| 164 | 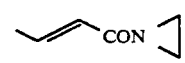 |
| 165 | 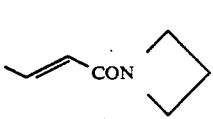 |
| 166 |  |
| 167 | 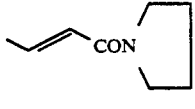 |
| Compound number | -CH=C(R³)CONR⁴R⁵ |
|---|---|
| 168 | 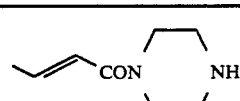 |
| 169 | 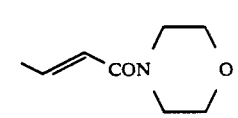 |
| 170 | 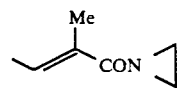 |
| 171 | 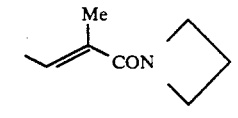 |
| 172 | 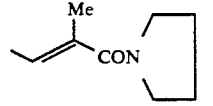 |
| 173 | 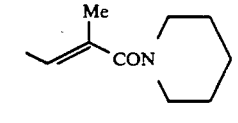 |
| 174 | 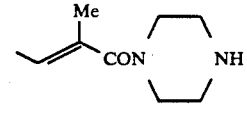 |
| 175 | 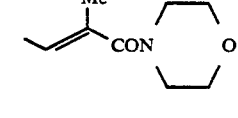 |
| 176 | 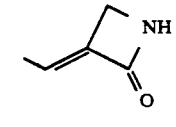 |
| 177 | 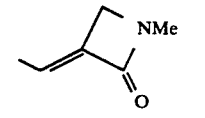 |

| | 23 | | 24 |
|---|---|---|---|
| | -continued | | -continued |
| | 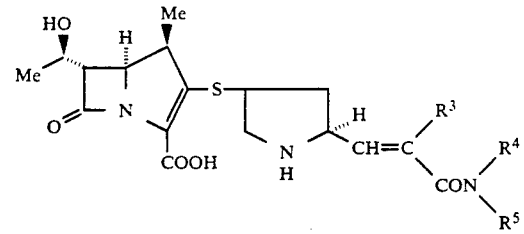 | | 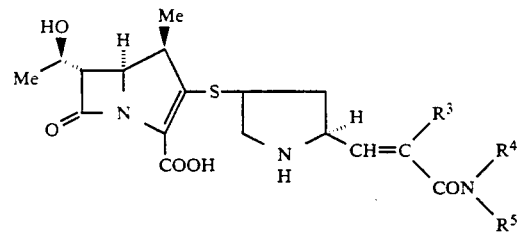 |
| Compound number | $-CH=C\begin{matrix}R^3\\CON\begin{matrix}R^4\\R^5\end{matrix}\end{matrix}$ | Compound number | $-CH=C\begin{matrix}R^3\\CON\begin{matrix}R^4\\R^5\end{matrix}\end{matrix}$ |
| 178 | 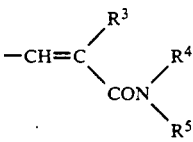 | 188 | 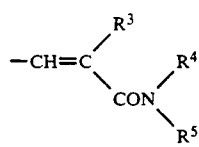 CONHtBu |
| 179 | 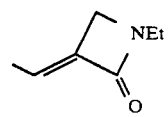 | 189 | 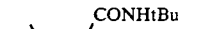 CONMe$_2$ |
| 180 | 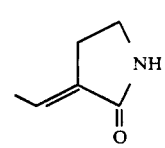 | 190 | 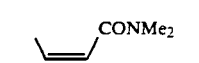 CON(Me)Et |
| 181 | 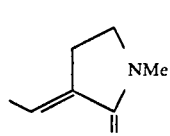 | 191 |  CON(Me)Pr |
| 182 | 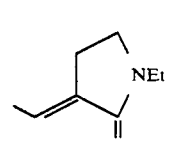 | 192 |  CON(Me)tBu |
| 183 | 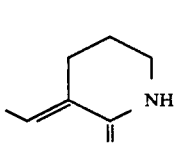 | 193 |  |
| 184 | 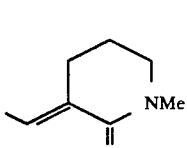 | 194 | 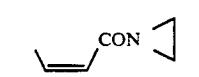 |
| | | 195 | 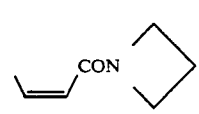 |
| | | 196 | 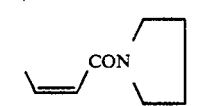 |
| | | 197 | 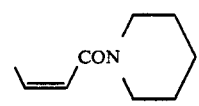 |
| 185 | 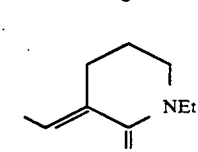 CONH$_2$ | 198 | 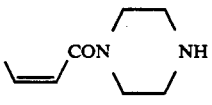 |
| 186 | 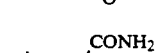 CONHMe | 199 | 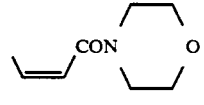 CONH$_2$ |
| 187 | 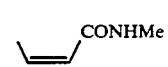 CONHEt | 200 | 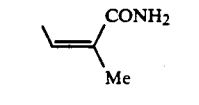 CONHMe |

-continued

[Structure shown with HO, Me, S, N, COOH, pyrrolidine-CH=C(R³)-CON(R⁴)(R⁵)]

$-CH=\overset{R^3}{\underset{\underset{R^5}{\overset{|}{CON}}}{C}}{\overset{}{}_{R^4}}$

| Compound number | |
|---|---|
| 201 | CH=C(Me)-CONMe₂ |
| 202 | CH=C(Me)-CON(cyclopropyl) |
| 203 | CH=C(Me)-CON(azetidinyl) |
| 204 | CH=C(Me)-CON(pyrrolidinyl) |
| 205 | CH=C(Me)-CON(piperidinyl) |
| 206 | CH=C(Me)-CON(piperazinyl-NH) |
| 207 | CH=C(Me)-CON(morpholinyl) |
| 208 | CH=C-(β-lactam NH, 4-membered) |
| 209 | CH=C-(β-lactam NMe, 4-membered) |

-continued

[Structure shown with HO, Me, S, N, COOH, pyrrolidine-CH=C(R³)-CON(R⁴)(R⁵)]

$-CH=\overset{R^3}{\underset{\underset{R^5}{\overset{|}{CON}}}{C}}{\overset{}{}_{R^4}}$

| Compound number | |
|---|---|
| 210 | CH=C-(lactam NEt, 4-membered) |
| 211 | CH=C-(γ-lactam NH, 5-membered) |
| 212 | CH=C-(γ-lactam NMe, 5-membered) |
| 213 | CH=C-(γ-lactam NEt, 5-membered) |
| 214 | CH=C-(δ-lactam NH, 6-membered) |
| 215 | CH=C-(δ-lactam NMe, 6-membered) |
| 216 | CH=C-(δ-lactam NEt, 6-membered) |

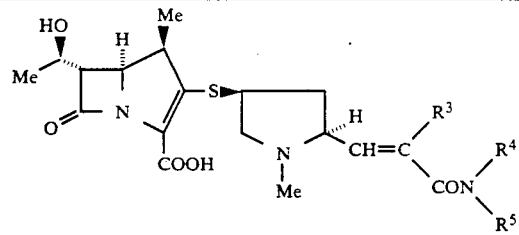
| Compound number | 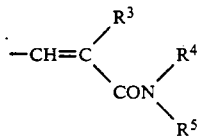 |
|---|---|
| 217 | 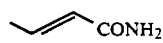 |
| 218 |  |
| 219 | 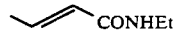 |
| 220 | 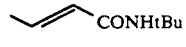 |
| 221 | 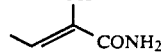 |
| 222 | 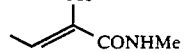 |
| 223 | 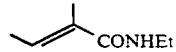 |
| 224 | 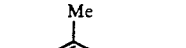 |
| 225 | 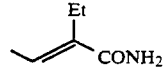 |
| 226 | 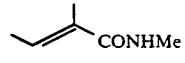 |
| 227 | 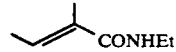 |
| 228 |  |
| 229 | 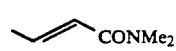 |
| 230 |  |
| 231 |  |
| 232 | 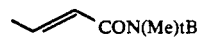 |
| 233 | 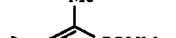 |
-continued
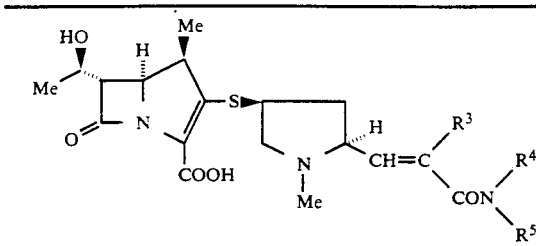
| Compound number | 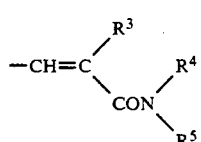 |
|---|---|
| 234 | 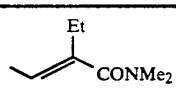 |
| 235 | 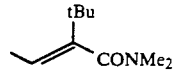 |
| 236 | 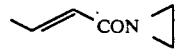 |
| 237 | 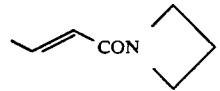 |
| 238 | 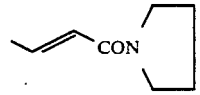 |
| 239 | 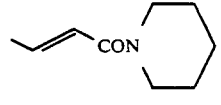 |
| 240 | 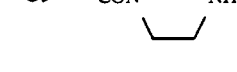 |
| 241 | 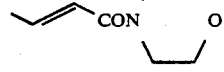 |
| 242 | 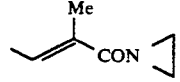 |
| 243 | 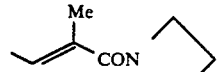 |
| 244 | 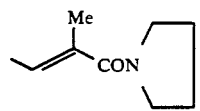 |

-continued

[Structure: carbapenem with HO-CH(Me)- group, Me, S-pyrrolidine-N-Me, with =CH-C(R³)(CONR⁴R⁵) substituent]

| Compound number | -CH=C(R³)(CONR⁴R⁵) |
|---|---|
| 245 | -CH=C(Me)-CO-piperidinyl |
| 246 | -CH=C(Me)-CO-piperazinyl (NH) |
| 247 | -CH=C(Me)-CO-morpholinyl |
| 248 | =CH-ethylidene-azetidinone (NH) |
| 249 | =CH-ethylidene-azetidinone (NMe) |
| 250 | =CH-ethylidene-azetidinone (NEt) |
| 251 | =CH-ethylidene-pyrrolidinone (NH) |
| 252 | =CH-ethylidene-pyrrolidinone (NMe) |
| 253 | =CH-ethylidene-pyrrolidinone (NEt) |

-continued

[Structure: same carbapenem core, different stereochemistry at pyrrolidine]

| Compound number | -CH=C(R³)(CONR⁴R⁵) |
|---|---|
| 254 | =CH-ethylidene-piperidinone (NH) |
| 255 | =CH-ethylidene-piperidinone (NMe) |
| 256 | =CH-ethylidene-piperidinone (NEt) |
| 257 | -CH=CH-CONH₂ |
| 258 | -CH=CH-CONHMe |
| 259 | -CH=CH-CONHEt |
| 260 | -CH=CH-CONHtBu |
| 261 | -CH=CH-CONMe₂ |
| 262 | -CH=CH-CON(Me)Et |
| 263 | -CH=CH-CON(Me)Pr |
| 264 | -CH=CH-CON(Me)tBu |
| 265 | -CH=CH-CON(aziridinyl) |
| 266 | -CH=CH-CON(azetidinyl) |

-continued
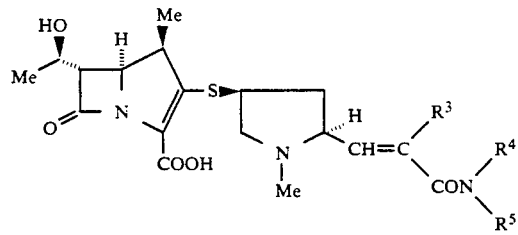
| Compound number | $-CH=C\begin{matrix}R^3\\CON\begin{matrix}R^4\\R^5\end{matrix}\end{matrix}$ |
|---|---|
| 267 | 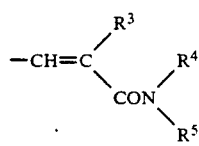 |
| 268 | 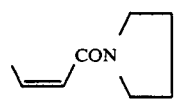 |
| 269 | 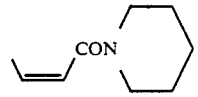 |
| 270 |  |
| 271 |  |
| 272 | 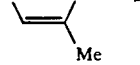 |
| 273 | 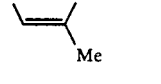 |
| 274 |  |
| 275 | 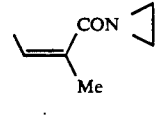 |
| 276 | 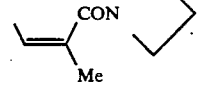 |
-continued
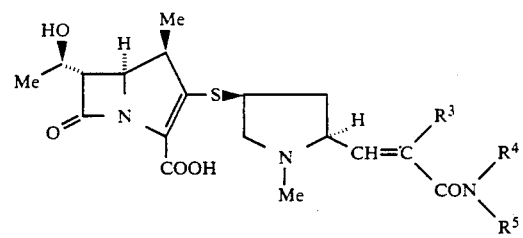
| Compound number | $-CH=C\begin{matrix}R^3\\CON\begin{matrix}R^4\\R^5\end{matrix}\end{matrix}$ |
|---|---|
| 277 | 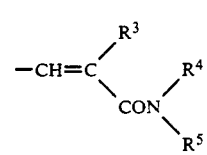 |
| 278 | 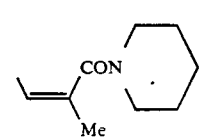 |
| 279 | 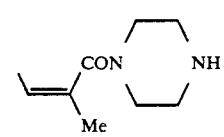 |
| 280 | 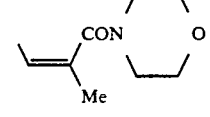 |
| 281 | 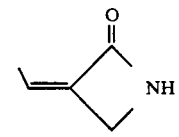 |
| 282 | 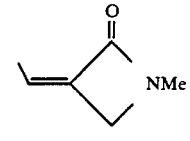 |
| 283 | 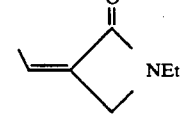 |
| 284 | 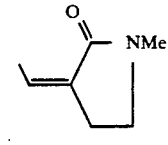 |
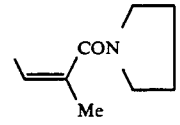
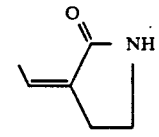

-continued

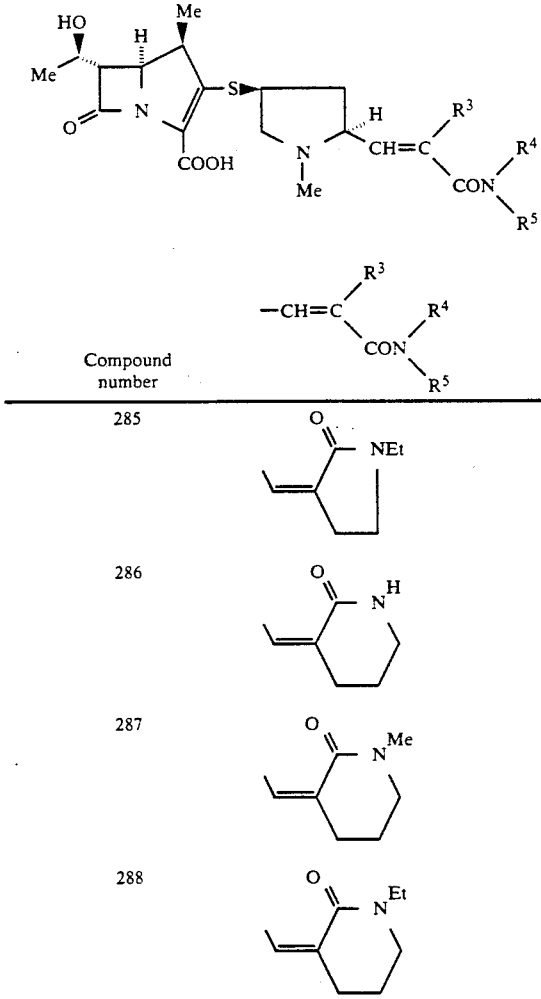

| Compound number | $-CH=C\begin{matrix}R^3\\R^4\\CON\\R^5\end{matrix}$ |
|---|---|
| 285 | ≠NEt (α,β-unsaturated amide, N-ethyl) |
| 286 | ≠NH (α,β-unsaturated lactam, 6-membered) |
| 287 | ≠NMe |
| 288 | ≠NEt |

The preferred examples of the compounds listed above are as follows:

(1) (5R,6S)-2-[(2S,4S)-2-[(E)-2-(aminocarbonyl)vinyl]-pyrrolidin-4-ylthio]-6-[(R)-1-hydroxyethyl]-1-carbapen-2-em-3-carboxylic acid (2) (5R,6S)-2-[(2S,4S)-2-[(E)-2-(N-methylaminocarbonyl)vinyl]pyrrolidin-4-ylthio]-6-[(R)-1-hydroxyethyl]-1-carbapen-2-em-3-carboxylic acid (5) (5R,6S)-2-[(2S,4S)-2-[(E)-2-(aminocarbonyl)-2-methylvinyl]pyrrolidin-4-ylthio]-6-[(R)-1-hydroxyethyl]-1-carbapen-2-em-3-carboxylic acid

(13) (5R,6S)-2-[(2S,4S)-2-[(E)-2-(N,N-dimethylaminocarbonyl)vinyl]pyrrolidin-4-ylthio]-6 [(R)-1-hydroxyethyl]-1-carbapen-2-em-3-carboxylic acid

(17) (5R,6S)-2-[(2S,4S)-2-[(E)-2-(N,N-dimethylaminocarbonyl)-2-methylvinyl]pyrrolidin-4-ylthio]-6-[(R)-1-hydroxyethyl]-1-carbapen-2-em-3-carboxylic acid

(20) (5R,6S)-2-[(2S,4S)-2-[(E)-2-(1-aziridinylcarbonyl)-vinyl]pyrrolidin-4-ylthio]-6-[(R)-1-hydroxyethyl]-1-carbapen-2-em-3-carboxylic acid

(22) (5R,6S)-2-[(2S,4S)-2-[(E)-2-(1-pyrrolidinylcarbonyl)vinyl]pyrrolidin-4-ylthio]-6-[(R)-1-hydroxyethyl]-1-carbapen-2-em-3-carboxylic acid

(24) (5R,6S)-2-[(2S,4S)-2-[(E)-2-(1-piperazinylcarbonyl)vinyl]pyrrolidin-4-ylthio]-6-[(R)-1hydroxyethyl]-1-carbapen-2-em-3-carboxylic acid

(32) (5R,6S)-2-[(2S,4S)-2-[(E)-(2-oxoazetidin-3-ylidene)methyl]pyrrolidin-4-ylthio]-6-[(R)-1hydroxyethyl]-1-carbapen-2-em-3-carboxylic acid

(35) (5R,6S)-2-[(2S,4S)-2-[(E)-(2-oxopyrrolidin-3-ylidene)methyl]pyrrolidin-4-ylthio]-6-[(R)-1hydroxyethyl]-1-carbapen-2-em-3-carboxylic acid

(41) (5R,6S)-2-[(2S,4S)-2-[(Z)-2-(aminocarbonyl)vinyl]-pyrrolidin-4-ylthio]-6-[(R)-1hydroxyethyl]-1-carbapen-2-em-3-carboxylic acid

(53) (5R,6S)-2-[(2S,4S)-2-[(Z)-2-(1-piperazinylcarbonyl)vinyl]pyrrolidin-4-ylthio]-6-[(R)-1hydroxyethyl]-1-carbapen-2-em-3-carboxylic acid

(67) (5R,6S)-2-[(2S,4S)-2-[(Z)-(2-oxopyrrolidin-3-ylidene)methyl]pyrrolidin-4-ylthio]-6-[(R)-1hydroxyethyl]-1-carbapen-2-em-3-carboxylic acid

(73) (5R,6S)-2-[(2S,4S)-2-[(E)-2-(aminocarbonyl)vinyl]-1-methylpyrrolidin-4-ylthio]-6-[(R)-1-hydroxyethyl]-1-carbapen-2-em-3-carboxylic acid

(85) (5R,6S)-2-[(2S,4S)-2-[(E)-2-(N,N-dimethylaminocarbonyl)vinyl]-1-methylpyrrolidin-4-ylthio]-6-[(R)-1-hydroxyethyl]-1-carbapen-2-em-3-carboxylic acid

(92) (5R,6S)-2-[(2S,4S)-2-[(E)-2-(1-aziridinylcarbonyl)-vinyl]-1-methylpyrrolidin-4-ylthio]-6[(R)-1-hydroxyethyl]-1-carbapen-2-em-3-carboxylic acid

(96) (5R,6S)-2-[(2S,4S)-2-[(E)-2-(1-piperazinylcarbonyl)vinyl]-1-methylpyrrolidin-4-ylthio]- 6-[(R)-1-hydroxyethyl]-1-carbapen-2-em-3-carboxylic acid (107) (5R,6S)-2-[(2S,4S)-2-[(E)-(2-oxopyrrolidin-3-ylidene]methyl]-1-methylpyrrolidin-4-ylthio]-6-[(R)-1-hydroxyethyl]-1-carbapen-2-em-3-carboxylic acid (145) (1R,5S,6S)-2-[(2S,4S)-2-[(E)-2-(aminocarbonyl)-vinyl]pyrrolidin-4-ylthio]-6-[(R)-1hydroxyethyl]-1-methyl-1-carbapen-2-em-3-carboxylic acid (146) (1R,5S,6S)-2-[(2S,4S)-2-[(E)-2-(N-methylaminocarbonyl)vinyl]pyrrolidin-4-ylthio]-6-[(R)-1hydroxyethyl]-1-methyl-1-carbapen-2-em-3-carboxylic acid (149) (1R,5S,6S)-2-[(2S,4S)-2-[(E)-2-(aminocarbonyl}-2-methylvinyl]pyrrolidin-4-ylthio]-6-[(R)-1-hydroxyethyl]-1-methyl-1-carbapen-2-em-3-carboxylic acid (157) (1R,5S,6S)-2-[(2S,4S)-2-[(E)-2-(N,N-dimethylaminocarbonyl)vinyl]pyrrolidin-4-ylthio]6-[(R)-1-hydroxyethyl]-1-methyl-1-carbapen-2-em-3-carboxylic acid (161) (1R,5S,6S)-2-[(2S,4S)-2-[(E)-2-(N,N-thio]-6-[(R)-1-hydroxyethyl]-1-methyl-1-carbapen-2-em-3-carboxylic acid (164) (1R,5S,6S)-2-[(2S,4S)-2-[(E}-2-(1-aziridinylcarbonyl)vinyl]pyrrolidin-4-ylthio]6-[(R)-1hydroxyethyl]-1-methyl-1-carbapen-2-em-3-carboxylic acid (166) (1R,5S,6S)-6-[(R)-1-hydroxyethyl]-1-methyl 2-[(2S,4S)-2-[(E)-2-(1-pyrrolidinylcarbonyl)vinyl]pyrrolidin-4-ylthio]-1-carbapen-2-em-3-carboxylic acid (168) (1R,5S,6S)-6-[(R)-1-hydroxyethyl]-1-methyl-2-[(2S,4S)-2-[(E)-2-(1-piperazinylcarbonyl)vinyl]-pyrrolidin-4-ylthio]-1-carbapen-2-em-3-carboxylic acid (176) (1R,5S,6S)-6-[(R)-1-hydroxyethyl]-1-methyl-2-[(2S,4S)-2-[(E)-2-(2-oxoazetidin-3-ylidene)methyl]pyrrolidin-4-ylthio]-1-carbapen-2-em-3-carboxylic acid (179) (1R,5S,6S)-6-[(R)-1-hydroxyethyl]-1-methyl-2-[(2S,4S)-2-[(E)-2-(2-oxopyrrolidin-3ylidene)methyl]-pyrrolidin-4-ylthio]-1-carbapen-2-em-3carboxylic acid (182) (1R,5S,6S)-6-[(R)-1-hydroxyethyl]-1-methyl-2-[(2S,4S)-2 [(E)-(2-oxopiperidin-3-ylidene)methyl]pyrrolidin-4-ylthio]-1-carbapen-2-em-3carboxylic acid (185) (1R,5S,6S)-2-[(2S,4S)-2-[(Z}-2-(aminocarbonyl)-vinyl]pyrrolidin-4-ylthio]-6-[(R)-1-hydroxyethyl]-1-methyl-1-carbapen-2-em-3-carboxylic acid (189) (1R,5S,6S)-2-[(2S,4S)-2-[(Z)-2-(N,N-dimethylaminocarbonyl)vinyl]pyrrolidin-4-ylthio]-6-[(R)-1 hydroxyethyl]-1-methyl-1-carbapen-2-em-3-carboxylic acid (197) (1R,5S,6S)-6-[(R)-1-hydroxyethyl]-1-methyl-2-[(2S,4S)-2-[(Z}-2-(1-piperazinylcarbonyl)vinyl]-pyrrolidin 4-ylthio]-1-carbapen-2-em-3-carboxylic acid (211) (1R,5S,6S)-6-[(R)-1-hydroxyethyl]-1-methyl-2-[(2S,4S)-2-[(Z)-(2-oxopyrrolidin-3-ylidene)methyl]-pyrrolidin- 4-ylthio]-1-carbapen-2-em-3-carboxylic acid (217) (1R,5S,6S)-2-[(2S,4S)-2-[(E)-2-(aminocarbonyl)-vinyl]-1-methylpyrrolidin-4-ylthio]-6-[(R)-1-hydroxyethyl]-1-methyl-1-carbapen-2-em-3-carboxylic acid (229) (1R,5S,6S)-2-[(2S,4S)-2-[(E)-2-(N,N-dimethylaminocarbonyl)vinyl]-1-methylpyrrolidin-4-ylthio]-6-[(R)-1-hydroxyethyl]-1-methyl-1-carbapen-2-em-3-carboxylic acid (236) (1R,5S,6S)-2-[(2S,4S)-2-[(E)-2-(1-aziridinylcarbonyl)vinyl]-1-methylpyrrolidin-4-ylthio]-6-[(R)-1-hydroxyethyl]-1-methyl-1-carbapen-2-em-3-carboxylic acid (240) (1R,5S,6S}-6-[(R)-1-hydroxyethyl]-1-methyl-2-[(2S,4S)-2-[(E)-2-(1-piperazinylcarbonyl)vinyl]-1-methylpyrrolidin-4-ylthio]-1-carbapen-2-em-3-carboxylic acid and (251) (1R,5S,6S)-6-[(R)-1-hydroxyethyl]-1-methyl-2-[(2S,4S)-2-[(E)-(2-oxopyrrolidin-3-ylidene)methyl]-1-methylpyrrolidin-4-ylthio]-1-carbapen-2-em-3-carboxylic acid.

Especially the compounds of (1), (2), (5), (13), (35), (73), (85), (96}, (145), (146), (149), (157), (164), (168), (179), (182), (185), (189), (211), (217) and (229) are preferred among the above compounds.

Among the compounds of the formula (I) and among the preferred specific examples given above, more preferred are a group of compounds represented by the formula (I-b):

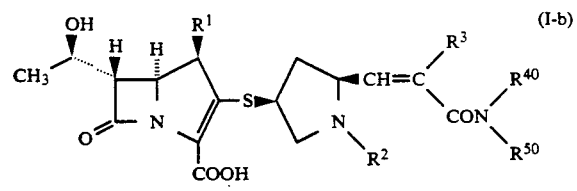

wherein at least one of $R^{40}$ and $R^{50}$ is a hydrogen atom, and $R^1$, $R^2$ and $R^3$ are as defined above, and a group of compounds represented by the formula (I-c):

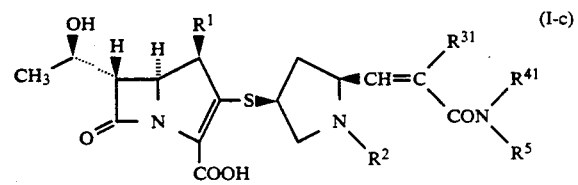

wherein $R^{31}$ and $R^{41}$ together form a methylne group, an ethylene group or a propylene group, and $R^1$, $R^2$ and $R^5$ are as defined above.

The compound of the formula (I) can be formed into a pharmaceutically acceptable salt or ester by a conventional method.

The salt of the compound of the formula (I) means a common pharmaceutically acceptable salt and includes salts of the carboxyl group at the 3-position of the carbapenem structure or at the nitrogen atom capable of forming a salt on the pyrrolidine ring at the 2-position of the carbapenem structure.

The basic addition salt at said carboxyl group includes, for example, an alkali metal salt such as a sodium salt or a potassium salt; an alkaline earth metal salt such as a calcium salt or a magnesium salt; an ammonium salt; an aliphatic amine salt such as a trimethylamine salt, a triethylamine salt, a dicyclohexylamine salt, an ethanolamine salt, a diethanolamine salt, a triethanolamine salt or a procaine salt; an aralkylamine salt such as an N,N'-dibenzylethylenediamine salt; an aromatic heterocyclic amine salt such as a pyridine salt, a picoline salt, a quinoline salt or an isoquinoline salt; a quaternary ammonium salt such as a tetramethylammonium salt, a tetraethylammonium salt, a benzyltrimethylammonium salt, a benzyltriethylammonium salt, a benzyltributylammonium salt, a methyltrioctylammonium salt or a tetrabutylammonium salt; and a basic amino acid salt such as an arginine salt or a lysine salt.

The acid addition salt at the pyrrolidine base includes, for example, an inorganic salt such as a hydrochloride, a sulfate, a nitrate, a phosphate, a carbonate, a hydrogencarbonate or a perchlorate; an organic salt such as an acetate, a propionate, a lactate, a maleate, a fumarate, a tartrate, a malate, a succinate or an ascorbate; a sulfonate such as a methanesulfonate, an isethionate, a benzenesulfonate or a p-toluenesulfonate; and an acidic amino acid salt such as an aspartate or a glutamate.

The non-toxic ester of the compound of the formula (I) means a common pharmaceutically acceptable ester at the carboxyl group at the 3-position of the carbapenem structure. For example, it includes an ester with an alkanoyloxymethyl group such as an acetoxymethyl group or a pivaloyloxymethyl group, an ester with an alkoxycarbonyloxyalkyl group such as a 1-(ethoxycarbonyloxy)ethyl group, an ester with a phthalidyl group and an ester with a (5-substituted 2-oxo-1,3-dioxol-4-yl)methyl group such as a (5-methyl-2-oxo-1,3-dioxol-4-yl)methyl group.

Now, processes for producing the compounds of the present invention will be described.

The compounds of the present invention can be prepared by the following processes A and B.

Process A

The compound of the formula (I) of the present invention can be prepared by reacting a compound of the formula (II) as defined above or its reactive derivative with a compound of the formula (III) as defined above to form a compound of the formula (IV) as defined above and if necessary, removing any protecting group of the compound of the formula (IV).

Process B

The compound of the formula (I) of the present invention can be prepared by reacting an oxidizing agent to a compound of the formula (V) as defined above, to form a compound of the formula (VI) as defined above, then reacting the compound of the formula (VI) with a compound of the formula (VII-a) or (VII-b) as defined above to form a compound of the formula (IV) as defined above, and if necessary, removing any protecting group of the compound of the formula (IV).

The reaction of the compound of the formula (II) with the compound of the formula (III) is preferably conducted by using as the compound of the formula (II) a reactive derivative thereof. Namely, the compound of the formula (II) can be converted to a reactive derivative of the formula:

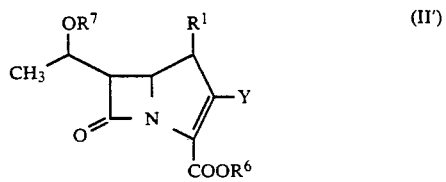

wherein $R^1$, $R^6$ and $R^7$ are as defined above, and Y is a leaving group, by reacting an activating reagent to the compound of the formula (II) in an inert organic solvent in the presence of a base.

The inert organic solvent to be used for the reaction may, for example, be diethyl ether, tetrahydrofuran, dioxane, benzene, toluene, chlorobenzene, methylene chloride, chloroform, carbon tetrachloride, dichloroethane, trichloroethylene, acetone, ethyl acetate, acetonitrile, N,N-dimethylformamide, hexamethylphosphoric triamide or a mixture of such solvents. Particularly preferred are acetonitrile and benzene.

The base to be used for the reaction may, for example, be a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) or 1,5-diazabicyclo[4.3.0]non-5-ene (DBN); or an aromatic amine such as pyridine, 4-dimethylaminopyridine, picoline, lutidine, quinoline or isoquinoline. Particularly preferred are N,N-diisopropylethylamine and triethylamine.

The activating reagent to be used for the reaction may, for example, be an acid anhydride such as trifluoroacetic anhydride, methanesulfonic anhydride, trifluoromethanesulfonic anhydride or p-toluenesulfonic anhydride; or an acid chloride such as methanesulfonyl chloride, p-toluenesulfonyl chloride or diphenyl chlorophosphate. Particularly preferred is diphenyl chlorophosphate.

In the formula (II'), Y is a leaving group such as a trifluoroacetoxy group, a methanesulfonyloxy group, a trifluoromethanesulfonyloxy group, a p-toluenesulfonyloxy group or a diphenoxyphosphoryloxy group. Particularly preferred is a diphenoxyphosphoryloxy group.

For the reaction, from 1 to 3 mol, preferably from 1 to 1.5 mol of the base and from 1 to 1.2 mol of the activating reagent are used per mol of the compound of the formula (II).

The reaction is conducted usually within a temperature range of from −40° to 50° C., preferably from −20° to 20° C. and usually completed quantitatively in from 0.5 to 3 hours.

After completion of the reaction, the reaction product is treated in accordance with a usual method to obtain the reactive derivative (II') of the compound of the formula (II) quantitatively.

The compound of the formula (II') may be reacted with the compound of the formula (III) without or after being isolated. The reaction is conducted using the abovementioned inert organic solvent and the base, and from 1 to 2 mol, preferably from 1 to 1.5 mol, of the base and from 1 to 1.2 mol of the compound of the formula (III) are used per mol of the compound of the formula (II'). The reaction is conducted usually within a temperature range of −40° to 50° C., preferably from −20° to 20° C. and usually completed quantitatively in from 0.5 to 3 hours.

Further, the compound of the formula (IV) can be prepared in one step from the compound of the formula (II). Namely, without isolating the reactive derivative of the formula (II') prepared from the compound of the formula (II), the compound of the formula (III) is reacted thereto in the same reaction system to prepare the compound of the formula (IV) efficiently. To conduct the production in one step, from 2 to 4 mol, preferably from 2.5 to 3.5 mol, of the base is employed per mol of the compound of the formula (II).

After completion of the reaction, usual treatment is conducted to obtain a crude product of the formula (IV), which may be subjected to a reaction for removing a protecting group without purification. However, it is preferred to purify the crude product (IV) by crystallization or by column chromatography by means of e.g. silica gel.

From the compound of the formula (IV) thus obtained, a compound of the formula (I) can be obtained, if necessary, by conducting a reaction for removing a protecting group for a hydroxyl group, an imino group and a carboxyl group.

The starting material of the formula (II) can be prepared, for example, by a method by Salzmann et al. when $R^1$ is a hydrogen atom (J. Am. Chem. Soc., vol. 102, p.6161–6163 (1981)) or by a method by Shih et al. when $R^1$ is a methyl group (Heterocycles, vol. 21, p.29–40 (1984)).

The compound of the formula (III) as the starting material, can be synthesized from hydroxyproline in accordance with the following reaction scheme:

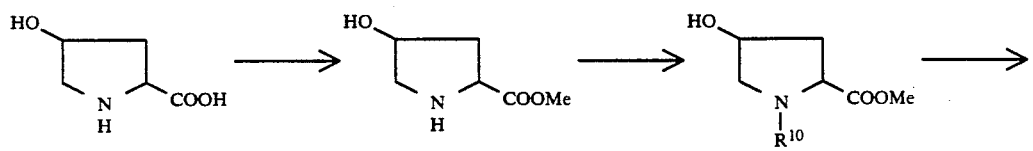

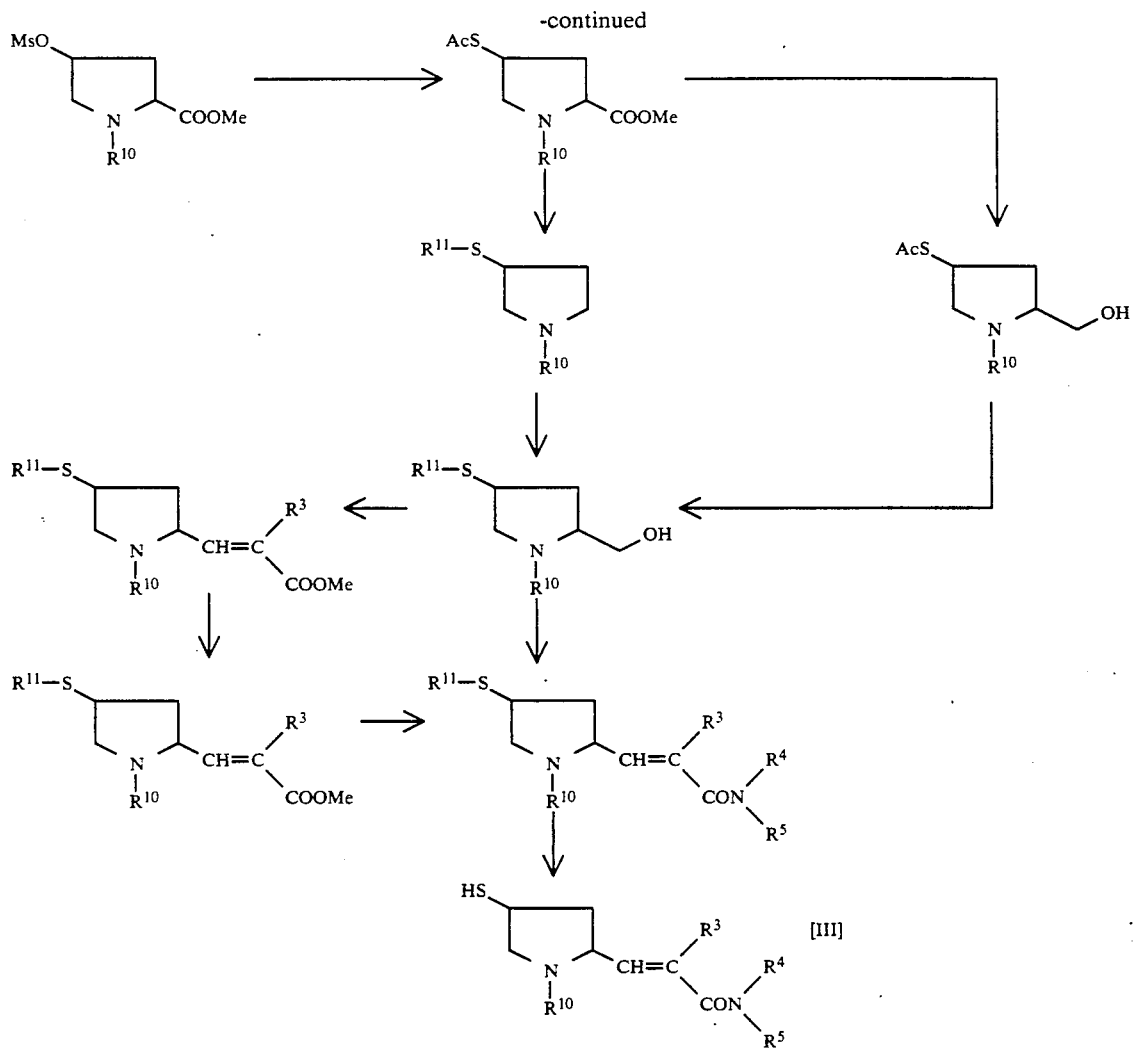

In the above formulas, $R^3$, $R^4$ and $R^5$ are as defined above, $R^{10}$ is an imino-protecting group, and $R^{11}$ is a trityl group or a p-methoxybenzyl group.

Now, Process B will be described.

The method of subjecting the compound of the formula (V) to an oxidation reaction to obtain a compound of the formula (VI) will be described.

A number of processes for producing aldehydes by oxidation reactions of primary alcohols, are generally known. However, there has been no report on a method of converting a hydroxyl compound having a carbapenem structure to an aldehyde compound, since the carbapenem structure is unstable. As a result of an extensive study of such a conversion reaction, the present inventors have found it possible to readily produce a compound of the formula (VI) without decomposing the carbapenem structure, by using a combination of a hexavalent chromium or a dimethyl sulfoxide with an electrophilic reagent, as the oxidizing agent.

As a suitable chromium (VI) oxidizing agent, a chromium oxide-pyridine complex (Collins reagent), pyridinium dichromate (PDC), pyridinium chlorochromate (PCC), 4-dimethylaminopyridinium chlorochromate or tertbutyl chromate may, for example, be mentioned.

As a suitable electrophilic reagent to be used in combination with dimethyl sulfoxide, oxalyl chloride, thionyl chloride, methanesulfonyl chloride, p-toluenesulfonyl chloride, benzoyl chloride, acetyl chloride, acetyl bromide, cyanuric chloride, methyl chloroformate, ethyl chloroformate, acetic anhydride, trifluoroacetic anhydride, methanesulfonic anhydride, p-toluenesulfonic anhydride, dicyclohexylcarbodiimide, a sulfur trioxide-pyridine complex, phosphorus trichloride, phosphorus oxychloride or phosphorus pentoxide may, for example, be mentioned. Particularly preferred electrophilic reagents are oxalyl chloride, thionyl chloride, methanesulfonyl chloride, methanesulfonic anhydride and trifluoroacetic anhydride.

The oxidation reaction can be carried out by properly combining such conditions as the amount of the reagent, the solvent, the reaction temperature and the reaction time, although such conditions vary depending upon the types of the compound of the formula (V) and the oxidizing reagent.

For example, the oxidation reaction by means of a chromium (VI) oxide-pyridine complex can be conducted in an inert solvent using from 4 to 8 mol, preferably from 5 to 6 mol, of the complex per mol of the compound of the formula (V). The reaction time is from 5 to 30 minutes, preferably from 10 to 15 minutes, at room temperature. As a preferred solvent, an inert solvent such as pyridine, acetone, methylene chloride or a solvent mixture thereof, may be mentioned. Particularly preferred is methylene chloride.

The oxidation reaction using e.g. pyridinium dichromate as the oxidizing agent, can be conducted in an inert solvent using from 1 to 1.5 mol, preferably from 1.2 to 1.3 mol, of the oxidizing agent per mol of the compound of the formula (V). The reaction can be completed in from 2 to 5 hours at a temperature of from $-10°$ to $20°$ C., preferably from $0°$ to $10°$ C. As a preferred solvent, water or an inert organic solvent such as N,N-dimethylformamide, dimethyl sulfoxide, methylene chloride, acetone or a solvent mixture thereof, may, for example, be mentioned. Particularly preferred are N,N-dimethylformamide and methylene chloride.

The oxidation reaction using e.g. pyridinium chlorochromate as the oxidizing agent, can be conducted in an inert solvent using from 1 to 2 mol, preferably from 1.2 to 1.5 mol, of said oxidizing agent per mol of the compound of the formula (V). The reaction time is from 1 to 2 hours at room temperature. As a preferred solvent, water or an inert organic solvent such as N,N-dimethylformamide, dimethyl sulfoxide, methylene chloride, acetone or a solvent mixture thereof, may be mentioned. Particularly preferred are N,N-dimethylformamide and methylene chloride. When the compound of the formula (V) is unstable against an acid, it is preferred to conduct the reaction by adding about 2 mol of a weakly alkaline salt such as sodium acetate, per mol of the oxidizing agent.

The oxidation reaction by means of e.g. a combination of dimethyl sulfoxide with an electrophilic reagent can be carried out in accordance with a method disclosed by D. Swern et al. in "Synthesis", p.165–185 (1981). The reaction can be conducted in an inert solvent at a temperature of from $-75°$ C. to room temperature by reacting from 1.5 mol to a large excess of dimethyl sulfoxide and from 1 to 2 mol of an electrophilic reagent per mol of the compound of the formula (V) to form a dimethylsulfoxonium salt, then adding and reacting a compound of the formula (V) thereto, and if necessary, reacting from 1 to 8 mol of triethylamine, to obtain a compound of the formula (VI).

As a preferred solvent, an inert organic solvent such as dimethyl sulfoxide, methylene chloride, hexane, benzene, toluene, diethyl ether, acetone, acetonitrile, hexamethylphosphoric triamide or a solvent mixture thereof, may, for example, be mentioned. Particularly preferred is methylene chloride, hexamethylphosphoric triamide, dimethyl sulfoxide or a solvent mixture thereof.

The amount of the electrophilic reagent, the solvent and the reaction temperature may suitably be selected depending upon the type of the electrophilic reagent to be used for the reaction.

For example, when oxalyl chloride or thionyl chloride is used as the electrophilic reagent, from 1.2 to 1.5 mol of the electrophilic reagent is added at a temperature of from $-78°$ to $-60°$ C. to a methylene chloride solution containing from 2 to 3 mol of dimethyl sulfoxide per mol of the compound of the formula (II). This solution is stirred at the same temperature for 30 minutes. Then, to the solution of the resulting dimethylsulfoxonium salt, the compound of the formula (V) is added at a temperature of from $-78°$ to $-60°$ C. After stirring the mixture for from 15 to 30 minutes, from 2 to 7 mol of triethylamine is added to the reaction solution. This solution is stirred at a temperature of from $-78°$ to $-30°$ C. for from 15 to 30 minutes and further at room temperature for from 30 to 60 minutes to complete the oxidation reaction.

When an acid anhydride such as methanesulfonic anhydride, p-toluenesulfonic anhydride or trifluoroacetic anhydride, or an acid chloride such as methanesulfonic acid chloride, p-toluenesulfonic acid chloride or benzoyl chloride, is used as the electrophilic reagent, from 1.5 to 2 mol of the electrophilic reagent is added at a temperature of from $-30°$ to $-20°$ C. to hexamethylenephosphoric triamide, methylene chloride or a solvent mixture thereof containing 1 mol of the compound of the formula (V) and from 5 to 20 mol of dimethyl sulfoxide. After stirring the mixture at the same temperature for 2 to 4 hours, from 2 to 4 mol of triethylamine is added to the reaction solution. This solution is stirred at room temperature for from 10 to 30 minutes to complete the oxidation reaction.

After completion of the oxidation reaction, usual treatment is conducted, and the compound of the formula (VI) is extracted with methylene chloride. This extract solution is dried, and the filtrate thereof or the concentrated residue is used for the subsequent reaction without conducting purification.

Now, a process for producing a compound of the formula (IV) by reacting the compound of the formula (VI) with the compound of the formula (VII-a) or (VII-b), will be described.

The synthesis of an $\alpha,\beta$-unsaturated carbonyl derivative by a Wittig reaction, is conducted in accordance with the methods disclosed in references by A. Maerchker, "Org. Reactions", vol. 14, p.344 (1965); Mukaiyama et al., "Chem. Lett.", p. 405–408 (1984); W. C. Still et al., "Tetrahedron Letters", vol. 24, p.4405–4408 (1983).

The compound of the formula (IV) has cis(Z) and trans(E) geometrical isomers with respect to the double bond. In the Wittig reaction, by properly selecting the type of the compound of the formula (VII-a) or (VII-b), the reaction solvent and the reaction temperature, it is possible to selectively or preferentially produce either one of the (Z)-isomer or (E)-isomer.

The Wittig reaction by a phosphorane compound of the formula (VII-a) is conducted in an inert organic solvent by reacting from 1 to 2 mol of the compound of the formula (VII-a) to 1 mol of the compound of the formula (VI) at a temperature of from $0°$ to $80°$ C., preferably at room temperature for from 2 to 6 hours.

The inert organic solvent useful for the reaction may, for example, be methylene chloride, benzene, toluene, N,N-dimethylformamide, diethyl ether, diisopropyl ether, tetrahydrofuran, dioxane, 1,2-dimethoxyethane, hexane, methanol, ethanol or a solvent mixture thereof. By properly selecting such a solvent, it is possible to selectively or preferentially produce either one of the (Z)-isomer or the (E)-isomer.

The phosphorane compound useful for the reaction includes, for example, aminocarbonylmethylene(triphenyl)phosphorane, N-methylaminocarbonylmethylene(triphenyl)phosphorane, N-ethylaminocarbonylmethylene (triphenyl)phosphorane, triphenyl(N-propylaminocarbonylmethylene)phosphorane, triphenyl(N-isopropylaminocarbonylmethylene)phosphorane, N,N-dimethylaminocarbonylmethylene(triphenyl)phosphorane, N,N-diethylaminocarbonylmethylene(triphenyl)phosphorane, triphenyl(N,N-dipropylaminocarbonylmethylene)phosphorane, triphenyl(N,N-diisopropylaminocarbonylmethylene)phosphorane, 1-aziridinylcarbonylmethylene(triphenyl)-phosphorane, 1-azetidinylcarbonylmethylene(-triphenyl)-phosphorane, triphenyl(1-pyrrolidinylcarbonylmethylene)-phosphorane, piperidinocarbonylmethylene(triphenyl)-phosphorane, (2-oxo-3-pyrrolidinylidene)-triphenylphosphorane and (2-oxo-3-piperidylidene)triphenylphosphorane.

The Wittig reaction by a phosphonate compound of the formula (VII-b) is conducted either by reacting a base to the compound of the formula (VII-b) in the above-mentioned inert organic solvent to form an ylide and reacting the ylide with the compound of the formula (VI), or by reacting a base in the presence of both the compound of the formula (VII-b) and the compound of the formula (VI). The reaction proceeds smoothly under a mild condition when conducted in the presence of a catalytic amount or an excess amount of a metal chelating agent such as crown ether.

The base useful for the reaction includes, for example, n-butyl lithium, lithium diisopropylamide, lithium hexamethyldisilazie, potassium hexamethyldisilazide, sodium hydride and cesium carbonate.

The phosphonate compound useful for the reaction includes, for example, di(2,2,2-trifluoroethyl) (aminocarbonylmethyl)phosphonate, di(2,2,2-trifluoroethyl) (N-methylaminocarbonylmethyl)-phosphonate, di(2,2,2-trifluoroethyl) (N-isopropylaminocarbonylmethyl)-phosphonate, di(2,2,2-trifluoroethyl) (N,N-dimethylaminocarbonylmethyl)phosphonate, di(2,2,2-trifluoroethyl) (N,N-diethylaminocarbonylmethyl)-phosphonate, di(2,2,2-trifluoroethyl) (N,N-dipropylaminocarbonylmethyl)phosphonate, di(2,2,2-trifluoroethyl) (N,N-diisopropylaminocarbonylmethyl)-phosphonate, di(2,2,2-trifluoroethyl) (1-aziridinylcarbonylmethyl)phosphonate, di(-2,2,2trifluoroethyl) (1-azetidinylcarbonylmethyl)phosphonate, di(2,2,2-trifluoroethyl) (1-pyrrolidinylcarbonylmethyl)-phosphonate, di(2,2,2-trifluoroethyl) (piperidinocarbonylmethyl)-phosphonate, di(2,2,2-trifluoroethyl) (2-oxo-3-pyrrolidinyl)phosphonate, di(2,2,2-trifluoroethyl) (2-oxo 3-piperidyl)phosphonate, dimethylaminocarbonylmethyl phosphonate, dimethyl (N-methylaminocarbonylmethyl)phosphonate, dimethyl (N-propylaminocarbonylmethyl)phosphonate, dimethyl (N-isopropylaminocarbonylmethyl)phosphonate, dimethyl (N,N-dimethylaminocarbonylmethyl)phosphonate, dimethyl (N,N-diethylaminocarbonylmethyl)-phosphonate, dimethyl (N,N-dipropylaminocarbonylmethyl)phosphonate, dimethyl (N,N-diisopropylaminocarbonylmethyl)phosphonate, dimethyl (1-aziridinylcarbonylmethyl)phosphonate, dimethyl (1-azetidinylcarbonylmethyl)phosphonate, dimethyl (1-pyrrolidinylcarbonylmethyl)phosphonate, dimethyl (piperidinocarbonylmethyl)phosphonate, dimethyl (2-oxo-3-pyrrolidinyl)phosphonate, dimethyl (2-oxo-3-piperidyl)phosphonate, diethyl (aminocarbonylmethyl)phosphonate, diethyl (N-methylaminocarbonylmethyl)phosphonate, diethyl (N-ethylaminocarbonylmethyl)phosphonate, diethyl (N-propylaminocarbonylmethyl)phosphonate, diethyl (N-isopropylaminocarbonylmethyl)phosphonate, diethyl (N,N-dimethylaminocarbonylmethyl)phosphonate, diethyl (N,N-diethylaminocarbonylmethyl)phosphonate, diethyl (N,N-dipropylaminocarbonylmethyl)phosphonate, diethyl (N,N-diisopropylaminocarbonylmethyl)phosphonate, diethyl (1-aziridinylcarbonylmethyl)phosphonate, diethyl (1-azetidinylcarbonylmethyl)phosphonate, diethyl (1-pyrrolidinylcarbonylmethyl)phosphonate, diethyl (piperidinocarbonylmethyl)phosphonate, diethyl (2-oxo-3-pyrrolidinyl)phosphonate, diethyl (2-oxo-3-piperidyl)phosphonate, diisopropyl (aminocarbonylmethyl)phosphonate, diisopropyl (N-methylaminocarbonylmethyl)phosphonate, diisopropyl (N-ethylaminocarbonylmethyl)phosphonate, diisopropyl (N-propylaminocarbonylmethyl)phosphonate, diisopropyl (N-isopropylaminocarbonylmethyl)phosphonate, diisopropyl (N,N-dimethylaminocarbonylmethyl)-phosphonate, diisopropyl (N,N-diethylaminocarbonylmethyl)phosphonate, diisopropyl (N,N-dipropylaminocarbonylmethyl)phosphonate, diisopropyl (N,N-diisopropylaminocarbonylmethyl)phosphonate, diisopropyl (1-aziridinylcarbonylmethyl)phosphonate, diisopropyl (1-azetidinylcarbonylmethyl)phosphonate, diisopropyl (1-pyrrolidinylcarbonylmethyl)-phosphonate, diisopropyl (piperidinocarbonylmethyl)-phosphonate, diisopropyl (2-oxo-3-pyrrolidinyl)phosphonate and diisopropyl (2-oxo-3-piperidyl)phosphonate. The metal chelating reagent useful for the reaction includes, for example, 15-crown-5, 18-crown-6, dicyclohexano-18-crown-6, hexamethylphosphoric triamide and cryptand 222. Particularly preferred are 15-crown-5 and 18-crown-6.

In the reaction, the selection of the types of the phosphonate compound and the base, their combination as well as the selection of the reaction solvent and the reaction temperature, give a substantial influence over the yield and the Z/E ratio of the geometrical isomers with respect to the double bond.

The reaction is usually conducted using from 1 to 1.15 mol of the compound of the formula (VII-b), from 1 to 5 mol of the base and, if necessary, from 1 to 5 mol of the metal chelating reagent per mol of the compound of the formula (VI). The reaction temperature is from $-75°$ to $50°$ C., and the reaction time is from 0.5 to 3 hours.

After completion of the reaction, usual treatment is conducted to obtain a crude product of the formula (IV), which can be subjected to a reaction for removing any protecting group without purification. However, it is preferred to purify the crude compound (IV) by e.g. crystallization or column chromatography using silica gel.

The compound of the formula (I) can be produced by optionally conducting the reactions for removing the protecting groups for the hydroxyl group, the imino group and the carboxyl group, as the case requires, from the compound of the formula (IV) obtained by the process A or B.

For the removal of the protecting groups, the method varies depending upon the type of the protecting groups. However, the removal can be conducted in accordance with conventional methods, for example, by addition of a solvent for decomposition, by chemical reduction or by hydrogenation.

For example, when in the above formula (IV), the protecting group for the hydroxyl group and/or for the imino group is an aralkyloxycarbonyl group such as a benzyloxycarbonyl group or a p-nitrobenzyloxycarbonyl group, and the protecting group for the carboxyl group is an aralkyl group such as a benzyl group, a p-nitrobenzyl group or a benzhydryl group, such protecting groups can be removed by catalytic hydrogenation by means of a platinum catalyst such as platinum oxide, platinum wire or platinum black, or a palladium catalyst such as palladium black, palladium oxide, palladium-carbon or palladium hydroxide-carbon.

As a solvent to be used for such a catalytic hydrogenation reaction, methanol, ethanol, tetrahydrofuran, dioxane, acetic acid or a solvent mixture of such an organic solvent with water or with a buffer solution of e.g. a phosphate, may be used.

The reaction can be completed in from 0.5 to 4 hours at a temperature within a range of from 0° to 50° C. under hydrogen gas stream of from 1 to 4 atm.

When in the above formula (IV), the protecting group for the hydroxyl group and/or the imino group is an allyloxycarbonyl group, and the protecting group for the carbonyl group is an allyl group, such protecting groups can be removed by reacting an organo-soluble palladium complex catalyst in an inert organic solvent containing an allyl group-capturing agent (method by W. McCombie et al., J. Org. Chem., vol. 47, p. 587-590 (1982), and method by F. Guibé et al., ditto, vol. 52, p. 4984-4993 (1987)).

The solvent useful for the reaction includes, for example, water, acetone, diethyl ether, tetrahydrofuran, dioxane, ethyl acetate, acetonitrile, methylene chloride, chloroform and a solvent mixture thereof.

The palladium catalyst suitable for use in this reaction, includes, for example, palladium-carbon, palladium hydroxide-carbon, palladium (II) chloride, palladium (II) acetate, tetrakis(triphenylphosphine)palladium (0), tetrakis(triphenoxyphosphine)palladium (0), tetrakis(triethoxyphosphine)palladium (0), bis[ethylenebis(diphenylphosphine]palladium (0), tetrakis[tri(2-furyl)phosphine]palladium (0), bis(triphenylphosphine)palladium (II) chloride and bis(triphenylphosphine)palladium (II) acetate.

The allyl group-capturing agent may, for example, be dimedone, formic acid, acetic acid, ammonium formate, sodium formate, sodium 2-ethylhexanoate, potassium 2-ethylhexanoate, pyrrolidine, piperidine and tributyltin hydride.

The reaction is conducted usually within a temperature range of from −10° to 50° C., preferably from 0° to 30° C. using from 0.01 to 0.5 mol of the palladium complex catalyst and from 1 to 6 mol of the capturing agent relative to 1 mol of the compound of the formula (IV), and the reaction is completed usually in from 0.5 to 3 hours.

Further, when in the above formula (IV), the protecting group for the hydroxyl group and/or the imino group is an o-nitrobenzyloxycarbonyl group, and the protecting group for the carboxyl group is an o-nitrobenzyl group, such protecting groups can be removed by a photo reaction (method by Amit et al., J. Org. Chem., vol. 39, p. 192-196 (1974)).

After completion of the reactions for removing the protecting groups, the compound of the formula (I) can be isolated by usual treatment such as column chromatography using silica gel or adsorptive resin, or freeze drying or crystallization.

Further, when the protecting group for the carboxyl group at the 3-position of the compound of the formula (IV) is a lower alkanoyloxyalkyl group such as an acetoxymethyl group or a pivaloyloxymethyl group, a methoxymethyl group, an indanyl group, or a phthalidyl group, such an ester will be physiologically hydrolyzed in vivo. Therefore, such a compound can directlybbe administered to a human being or to an animal without preliminarily removing the protecting group.

The compound of the formula (V) as the starting material, can be obtained by reacting a 4-mercaptopyrrolidine derivative of the formula (VIII) to an active derivative of the compound of the formula (II), as shown in the following reaction scheme (Reference Examples 8 and 9).

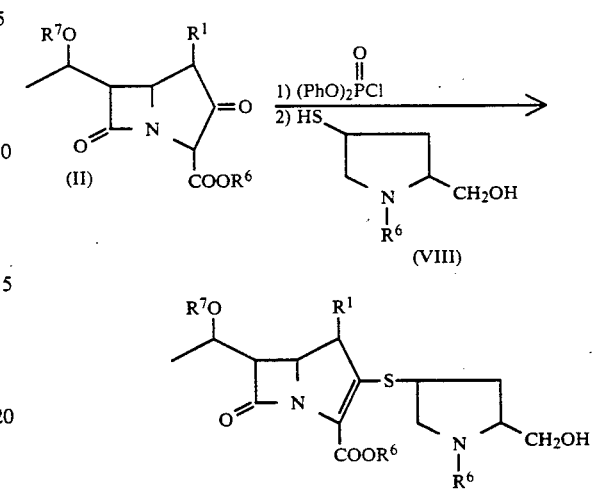

In the above formulas, $R^1$, $R^6$, $R^7$ and $R^8$ are as defined above.

The phosphorane compound of the formula (VII-a) as the starting material, can be produced in accordance with a method by Trippett et al., J. Chem. Soc., p. 3874 (1959). Likewise, the phosphate compound of the formula (IV-b) can be produced in accordance with a method by P. D. Landor et al., J. Chem. Soc., p. 93 (1977).

The compounds of the present invention exhibit strong antibacterial activities against various gram positive bacteria and gram negative bacteria.

To demonstrate the usefulness of the compounds of the present invention, the in vitro antibacterial activities against bacteria were measured by the following agar plate dilution method (standard method by Japan Chemotherapy Society, Chemotherapy, vol. 29, p. 76-79 (1981)). One platinum loopful of each test microorganism incubated overnight in Mueller Hinton broth, was inoculated to Mueller Hinton agar (inoculum size: 106 CFU/ml). Such culture media contained antibacterial agents in various concentrations. After incubation at 37° C. for 16 hours, the minimum inhibitory concentrations (MIC: μg/ml) were measured.

The DHP-I susceptivity was quantitatively analyzed by the method by Kropp et al., Antimicrob., Agents Chemother., vol. 22, p. 62-70 (1982), whereby the smaller the numerical value representing the ratio to imipenem (=1.0), the higher the stability.

The antibacterial activities and the DHP-I stability of the compounds of the present invention were measured using imipenem as a comparative compound. The results are shown in the following Tables.

| Minimum inhibitory concentration (MIC: μg/ml) | | |
| --- | --- | --- |
| Test microorganism | (E)-isomer of the compound of Example 3 | Compound of Example 12 |
| S. aureus MB4970 | 0.025 | 0.025 |
| E. cloacae Nek39 | 0.025 | 0.025 |
| Ps. aeruginosa MB5000 | 0.39 | 0.39 |

| DHP-I susceptivity | | |
| --- | --- | --- |
| (E)-isomer of the compound of Example 3 | Compound of Example 12 | Imipenem |

| | | |
|---|---|---|
| 0.2 | 0.04 | 1.0 |

The compounds of the present invention have excellent antibacterial activities against various gram positive bacteria and gram negative bacteria and are useful as antibacterial agents for the treatment and prevention of the human infectious diseases caused by such bacteria. Typical pathogens sensitive to the antibacterial agents of the present invention include, for example, species of genus Staphylococcus, genus Enterococcus, genus Escherichia, genus Enterobacter, genus Klebsiella, genus Serratia, genus Proteus and genus Pseudomonas. The, compounds of the present invention exhibit excellent antibacterial activities particularly against Methicillin resistant *Staphylococcus aureus* and against thienamycin resistant *Pseudomonas aeruqinosa*.

The compounds of the present invention are very stable against DHP-I although the stability varies depending upon the individual compounds, and they are excellent also in the physicochemical stability and in the solubility in water.

The compounds of the present invention may be used in the form of drug formulations suitable for non-oral administration, oral administration or external administration, by mixing them with carriers of solid or liquid excipients known in this field. The main administration route is non-oral (intravenous or intramuscular injection) administration by injection or local administration. Drug formulations include liquid formulations such as injection solutions, syrups or emulsions, solid formulations such as tablets, capsules or granules, and external application formulations such as ointments or suppositories. These formulations may contain additives such as a base, an assisting agent, a stabilizer, a wetting agent, an emulsifier, an absorption-promoting agent, a surfactant, etc. which are commonly employed, as the case requires.

The additives include, for example, distilled water for injection, Ringer's solution, glucose, sucrose syrup, gelatin, edible oil, cacao butter, ethylene glycol, sucrose, corn starch, magnesium stearate and talc.

The dose varies depending upon the condition of the patient, the weight, the age, the sex, the type of formulation, the number of administration times, etc. Usually, however, a preferred daily dose of the active ingredient to an adult is from about 5 to 50 mg/kg, and a preferred daily dose to a child is within a range of from about 5 to 25 mg/kg, which is preferably administered once a day or in a few times a day.

The compound of the present invention may be administered in combination with a DHP-I inhibiting agent such as cilastatin [sodium (Z)-7-(L-amino-2-carboxyethylthio)-2-(2,2-dimethylcyclopropanecarboxamide)-2-heptenoate] (Japanese Unexamined Patent publication No. 81518/1981; European Patent No. 28,778; J. Med. Chem., vol. 30, p. 1074 (1987)).

Now, the present invention will be described in further detail with reference to Examples and Reference Examples. However, it should be understood that the present invention is by no means restricted by such specific Examples.

In the Examples and Reference Examples, for the thin layer chromatography, Silicagel 60F₂₄₅ (Merck) was used as the plate, and an ultraviolet detector or ninhydrin color development method was used as a detecting means. As the silica gel for a column, Wakogel ® C-300 (Wako Junyaku) was used, and as silica gel for a reversed phase column, LC-SORB ® SP-B-ODS (Chemco) was used. For the high speed liquid chromatography, JASCO ® 800 series (Nippon Bunko) was used. When the NMR spectrum was measured in dimethyl sulfoxide-d₆ or chloroform-d₁ solution, tetramethylsilane (TMS) was used as the internal standard, and when it was measured in a deuterium oxide solution, 2,2-dimethyl-2-silapentane-5-sulfonate (DSS) was used. The measurement was conducted by XL200 (200 MHz: Varian) model spectrometer, and all δ values were represented by ppm.

The meanings of the abbreviations used in the NMR measurements, are as follows:

s: singlet
d: doublet
t: triplet
q: quartet
ABq: AB type quartet
dd: double doublet
m: multiplet
br: broad
J: coupling constant
Hz: hertz
DMSO-d₆ dimethyl sulfoxide-d₆
CDCl₃: chloroform-d₁
D₂O: deuterium oxide

EXAMPLE 1

Potassium (5R,6S)-2-[(2S,4S)-2-[(E)-2-(aminocarbonyl)vinyl]pyrrolidin-4-ylthio]-6-[(R)-1-hydroxyethyl]-1-carbapen-2-em-3-carboxylate

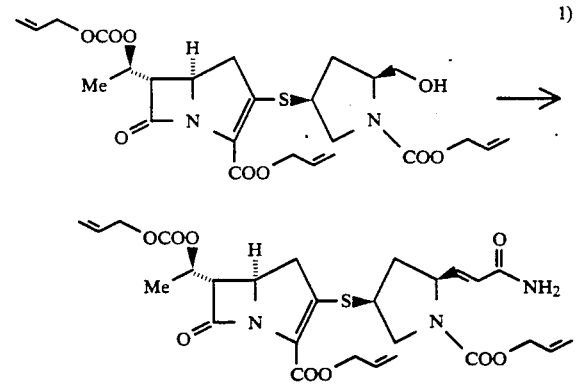

To a solution of dimethyl sulfoxide (0.29 ml, 4.0 mmol) and methylene chloride (12 ml), precooled at −70° C. with a dry ice-acetone bath was dropwise added oxalyl chloride (0.18 ml, 2.2 mmol), and the solution stirred for 30 minutes at the same temperature. A solution of allyl (5R,6S)-2-[(2S,4S)-N-allyloxycarbonyl-2-hydroxymethylpyrrolidin-4-ylthio]-6-[(R)-1-allyloxycarbonyloxyethyl]-1-carbapen-2-em-3-carboxylate (0.77 g, 1.4 mmol) in methylene chloride (3 ml) was treated dropwise with the reaction mixture at −78° C., stirred for 30 minutes, and treated dropwise with triethylamine (1.0 ml, 7.2 mmol) at −78° C. The mixture was stirred for 30 minutes and for another 1 hour after removal of the dry ice-acetone bath. The reaction mixture was washed each once with water, saturated aqueous sodium bicarbonate and saturated aqueous sodium chloride, and dried over anhydrous magnesium sulfate. To the filtrate was added aminocarbonylmethylene(triphenyl)phosphorane (0.69 g, 2.2 mmol; prepared by the method of Trippett et al., J. Chem. Soc., 3874 (1959)) and the mixture stirred at room temperature for 4 hours and concentrated. The residue was subjected to flash column chromatography on silica gel (Wakogel® C-300, 40 ml; elution with ethyl acetate) to give allyl (5R,6S)-2-[(2S,4S)-N-allyloxycarbonyl-2-(E)-2-(aminocarbonyl)vinyl]pyrrolidin-4-ylthio]-6-[(R)-1-allyloxycarbonyloxyethyl]-1-carbapen-2-em-3-carboxylate (0.20 g, 24% yield).

NMR(CDCl₃) δ: 1.46(3H,d,J=6 Hz), 1.9(1H,m), 2.7(1H,m), 3.1–3.4(4H,m), 3.6(1H,m), 4.1–4.3(2H,m), 4.6–4.9(7H,m), 5.15(1H,m), 5.2–5.6(8H,m), 6.0(4H,m), 6.8(1H,dd,J=6,15 Hz)

IR(KBr)cm⁻¹: 1780, 1750, 1700, 1650, 1260

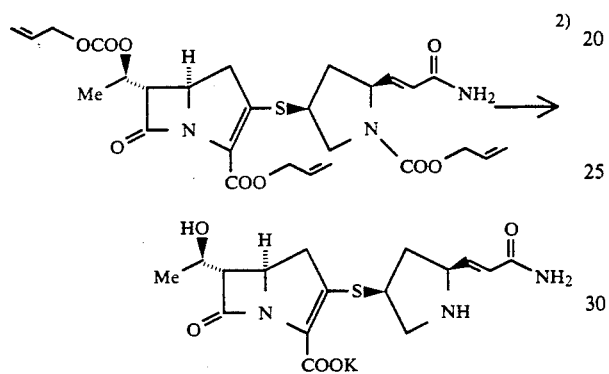

The compound (200 mg, 0.35 mmol) obtained in the previous reaction was dissolved in degassed acetone (10 ml). To the solution under ice-cooling under nitrogen were added successively triphenylphosphine (41 mg, 0.16 mmol), tributyltin hydride (0.31 ml, 1.15 mmol) and tetrakis(triphenylphosphine)palladium (O) (60 mg, 0.052 mmol), and the reaction solution was stirred at the same temperature for 30 minutes, followed by at room temperature for 30 minutes. A 0.5M solution of potassium 2-ethylhexanate (0.38 mmol) in ethyl acetate was treated with the reaction mixture. The mixture was stirred for 10 minutes, diluted with diethyl ether (20 ml), and stirred for 30 minutes under ice-cooling. The precipitate was collected, dissolved in water (5 ml), and the clarified filtrate subjected to reverse phase column chromatography (LC-SORB® SP-B-ODS, 50 ml; elution with 5% methanol in water. The fractions containing the desired product were combined, concentrated in vacuo, and lyophilized to afford the title compound (28.5 mg, 20% yield).

NMR(D₂O) δ: 1.4(3H,d,J=6 Hz), 1.8(1H,m), 2.8(1H,m), 3.2–3.7(5H,m), 4.0–4.4(4H,m), 6.35(1H,d,J=15 Hz), 6.95(1H,brd,J=15 Hz)

IR(KBr)cm⁻¹: 1760, 1680, 1590, 1400

HPLC;
Column YMC®-Pack ODS-A, 5 μ, 4.6. φ×150 mm.
Eluent: 0.01M Phosphate buffer (pH 6.5)/MeOH (90/10).
Flow rate: 1.5 ml/min.
Column temperature: 40° C.
Detector: UV 290 nm.
Retention time : 2.73 min.

EXAMPLE 2

Potassium [5R,6S)-2-[(2S,4S)-2-[(E)-2-(N,N-dimethylaminocarbonyl)vinyl]pyrrolidin-4-ylthio]-6-[(R)-1-hydroxyethyl]-1-carbapen-2-em-3-carboxylate

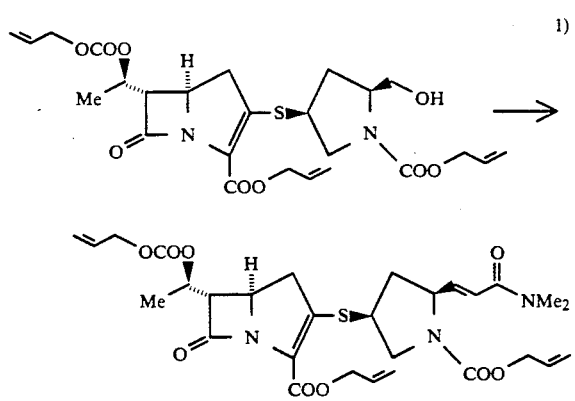

According to the same procedure as in Example 1-1), Swern oxidation of allyl (5R,6S)-2-[(2S,4S)-N-allyloxycarbonyl-2-hydroxymethylpyrrolidin-4-ylthio]-6-[(R)-1-allyloxycarbonyloxyethyl]-1-carbapen-2-em1-3-carboxylate (0.7 g, 1.4 mmol), followed by treatment with N,N-dimethylaminocarbonylmethylene(triphenyl)phosphorane (0.75 g, 2.2 mmol) afforded allyl (5R,6S}-2-[(2S,4S)-N-dimethylaminocarbonyl)vinyl]pyrrolidin-4-ylthio]-6-[(R)-1-allyloxycarbonyloxyethyl]-1-carbapen-2-em-3-carboxylate (170 mg, 20% yield).

NMR(CDCl₃) δ: 1.48(3H,d,J=6 Hz), 1.84(1H,m), 2.64(1H,m), 3.02(3H,s), 3.06(3H,s), 3.1–3.6(5H,m), 4.2(2H,m), 4.5–4.8(7H,m), 5.1–5.5(7H,m), 5.9(3H,m), 6.35(1H,d,J=14 Hz), 6.7(1H,brd,J=14 Hz)

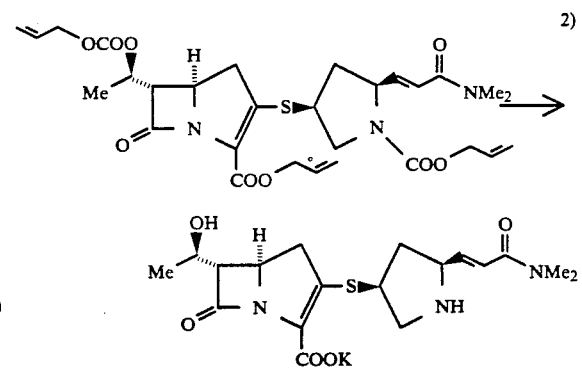

The same operation as in Example 1-2) was carried out by using the compound (170 mg, 0.28 mmol) obtained in the previous reaction to obtain the title compound (32 mg, 6% yield).

NMR(D₂O) δ: 1.44(3H,d,J=6 Hz), 1.95(1H,m), 2.9(1H,m), 3.2(3H,s), 3.35(3H,s), 3.3–3.7(5H,m), 4.0–4.2(2H,m), 4.45(2H,m), 6.8(1H,d,J=15 Hz), 6.9(1H,dd,J=5,15 Hz)

IR(KBr)cm⁻¹: 1765, 1600, 1400

HPLC;
Column: YMC®-Pack ODS-A, 5 μ, 4.6 φ×150 mm.
Eluent: 0.01M Phosphate buffer (pH 6.5)/MeOH (80/20).
Flow rate: 1.0 ml/min.

Column temperature: 40° C.
Detector: UV 290 nm.
Retention time: 3.32 min.

EXAMPLE 3

Potassium (1R,5S,6S)-2-[(2S,4S)-2-[(E)-2-(aminocarbonyl)vinyl]-pyrrolidin-4-ylthio]-6-[(R)-1-hydroxyethyl]-1-methyl-1-carbapen-2-em-3-carboxylate and its (Z)-isomer

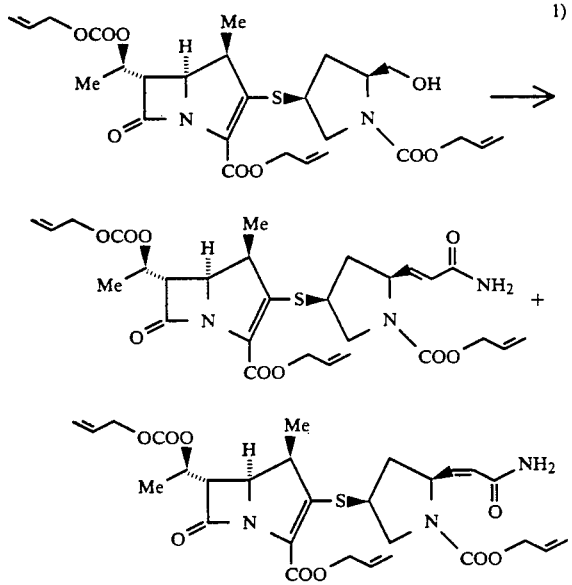

According to the same procedure as in Example 1-1), Swern oxidation of allyl (1R,5S,6S)-2-[(2S,4S)-N-allyloxycarbonyl-2-hydroxymethylpyrrolidin-4-ylthio]-6-[(R)-1-allyloxycarbonyloxyethyl]-1-methyl-1-carbapen-2-em-3-carboxylate (410 mg, 0.74 mmol), followed by treatment with aminocarbonylmethylene(triphenyl) phosphorane (357 mg, 1.1 mmol) were carried out. The concentrated residue was subjected to flash column chromatography on silica gel (Wakogel ® C-300 40 ml; elution with ethyl acetate) to afford allyl (1R,5S,6S)-2-(aminocarbonyl)vinyl]pyrrolidin-4-ylthio]-6-[(R)-1-allyloxycarbonyloxyethyl]-1-methyl-1-carbapen-2-em-3-carboxylate (50 mg, 11% yield) with the higher $R_f$ value, and its (E)-isomer (140 mg, 32% yield) with the lower $R_f$ value.

(E)-isomer
NMR(CDCl$_3$) δ: 1.26(3H,d,J=7 Hz), 1.48(3H,d,J=7 Hz), 1.8(1H,m), 2.65(1H,m), 3.35(3H,m), 3.66(1H,m), 4.0–4.25(2H,m), 4.5–4.9(7H,m), 5.15(1H,m), 5.25–5.5(7H,m), 5.65(1H,brs), 5.95(4H, m), 6.76(1H,dd,J=6,15 Hz) (Z)-isomer
NMR(CDCl$_3$) δ: 1.26(3H,d,J=7 Hz), 1.48(3H,d,J=7 Hz), 1.8(1H,m), 2.8(1H,m), 3.4(3H,m), 3.66(1H,m), 3.9–4.3(3H,m), 4.6–4.9(6H,m), 5.1–5.5(9H,m), 5.7(1H,brs), 6.0(5H,m)

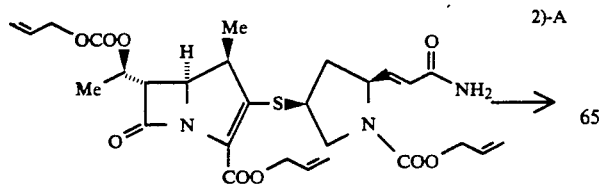

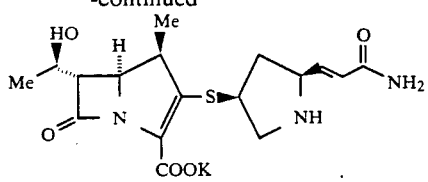

The same operation as in Example 1-2) was carried out by using the (E)-isomer obtained in the previous reaction. The mixture was worked up, chromatogaphed over reverse phase column (YMC.GEL ® ODS-AQ 120-S50, 50 ml: graduent elution with 10–15% methanol in water), concentrated the fractions containing the desired product, and lyophilized to afford the (E)-isomer (41.3 mg, 41% yield) of the title compounds.

NMR(D$_2$O) δ: 1.43(3H,d,J=7 Hz), 1.50(3H,d,J=7 Hz), 1.84(1H,m), 2.9(1H,m), 3.38(1H,dd,J=4,12 Hz), 3.65(3H,m), 4.1(1H,m), 4.25(1H,m), 4.45(2H,m), 6.43(1H,d,J=15 Hz), 7.03(1H,dd,J=7,15 Hz)
IR(KBr)cm$^{-1}$: 1750, 1680, 1590, 1390
HPLC;
   Column: YMC ®-Pack ODS-A, 5 μ, 4.6 φ×150 mm.
   Eluent: 0.01M Phosphate buffer (ph 6.5)/MeOH (95/5).
   Flow rate: 2.0 ml/min.
   Column temperature: 40° C.
   Detector: UV 290 nm.
   Retention time: 16.4 min.

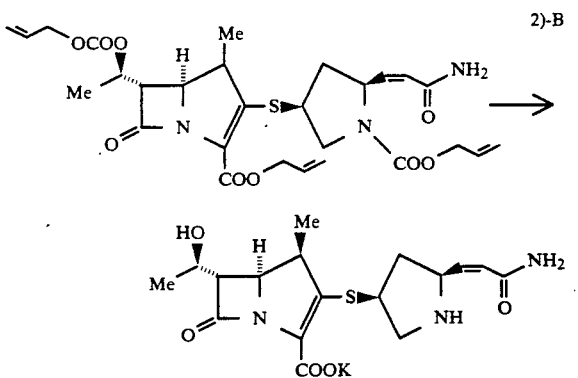

The same operation as in Example 1-2) was carried out by using the (Z)-isomer obtained in the previous reaction. The mixture was worked up, chromatographed over reverse phase column (LC-SORB ® SP-B-ODS, 14 ml; elution with 15% methanol-water), concentrated the fractions containing the desired product, and lyophilized to afford the (Z)-isomer (9.0 mg, 25% yield) of the title compounds.

NMR(D$_2$O) δ: 1.48(3H,d,J=7 Hz), 1.52(3H,d,j=7 Hz), 1.9(1H,m), 3.0(1H,m), 3.45(1H,dd,J=4,12 Hz), 3.7(3H,m), 4.2(1H,m), 4.5(3H,m), 5.1(1H,m), 6.39(1H,d,J=12.5 Hz), 6.49(1H,dd,J=7,12.5 Hz)
IR(KBr)cm$^{-1}$: 1750, 1680, 1600, 1390
HPLC;
   Column: YMC ®-Pack ODS-A, 5 μ, 4.6 φ×150 mm.
   Eluent: 0.01M Phosphate buffer (pH 6.5) MeOH (95/5).
   Flow rate: 2.0 ml/m:n.
   Column temperature: 40° C.

Detector: UV 290 nm.
Retention time : 18.9 min.

EXAMPLE 4

Potassium
(1R,5S,6S]-2-[(2S,4S)-2-[(E)-2-(N,N-dimethylaminocarbonyl)vinvl]cyrrolidin-4-ylthio]-6-[(R)-1-hydroxmethyl-1-methyl-1-carbapen-2-em-3-carboxylate

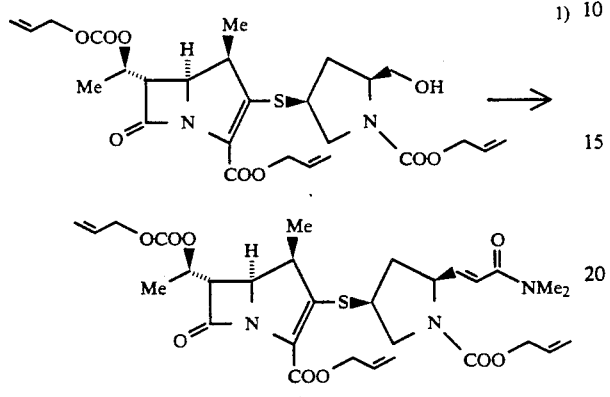

According to the same procedure as in Example 1-1), Swern ox;dation of allyl (1R,5S,6S)-2-[(2S,4S)-N-allyloxycarbonyl-2-hydroxymethylpyrrolidin-4-ylthio]-6-[(R)-1-allyloxycarbonyloxyethyl]-1-methyl-1-carbapen 2-em-3-carboxylate (320 mg, 0.58 mmol), followed by treatment with N,N-dimethylaminocarbonylmethylene(triphenyl)phosphorane (303 mg, 0.87 mmol afforded allyl (1R,5S,6S)-2-[(2S,4S)-N-allyloxycarbonyl-2 [(E)-2-(N,N-dimethylaminocarbonyl)vinyl]pyrrolidin-4-ylthio]-6-[(R)-1-allyloxycaroon loxyethyl]-1-methyl-1-carbapen-2-em-3-carboxylate 240 mg, 67% yield).

NMR(CDCl$_3$) δ: 1.26(3H,d,J=7 Hz), 1.48(3H,d,J=7 Hz), 1.9(1H,m), 2.7(1H,m), 3.0(3H,s), 3.06(3H,s), 3.4(3H,m), 3.65(1H,m), 4.0-4.25(2H,m), 4.6-4.9(7H,m), 5.1-5.5(7H,m), 6.0(3H,m), 6.4(1H,d,J=15 Hz), 6.7(1H,brd,J=15 Hz)

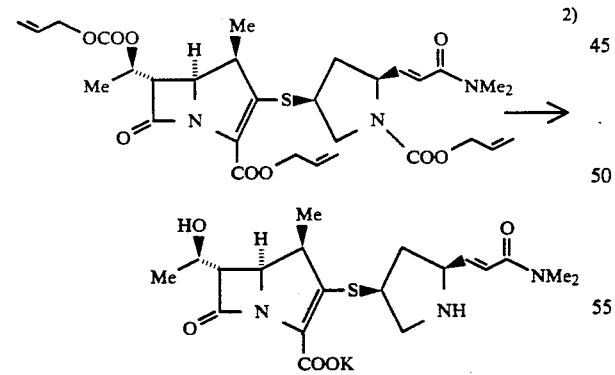

The same operation as in Example 1-2) was carried out by using the compound (240 mg, 0.39 mmol) obtained in the previous reaction. The mixture was worked up, chromatograpned over reverse phase column (YMC.GEL® ODS-AQ 120-S50, 50 ml; elution with 15% methanol-water), concentrated the fractions containing the desired product, and lyophilized to afford the title compound (58.6 mg, 34% yield).

NMR(D$_2$O) δ: 1.43(3H,d,J=7 Hz), 1.50(3H,d,J=7 Hz) 1.75(1H,m), 2.85(1H,m), 3.21(3H,s), 3.26(1H,dd,J=4,12 Hz), 3.36(3H,s), 3.6(3H,m), 4.1(2H,m), 4.45(2H,m), 6.80(1H,d,J=16 Hz), 6.92(1H,dd,J=6,16 Hz)

IR(KBr)cm$^{-1}$: 1750, 1660, 1600, 1400

HPLC;
  Column: YMC®-Pacx ODS-A, 5 μ, 4.6 φ×150 mm.
  Eluent: 0.01M Phosphate ouffer (pH 6.5)/MeOH (70/30).
  Flow rate: 1.0 ml/min.
  Column temperature: 40° C.
  Detector: UV 290 nm.
  Retention time : 2.86 min.

EXAMPLE 5

(5R,6S)-2-[(2S,4S)-2
[(E)-2-Aminocarbonyl-2-methylvinyl]pyrrolidin-4-ylthio]-6-[(R)-1-hydroxyethyl]-1-carbacen-2-em-3-carboxylic acid

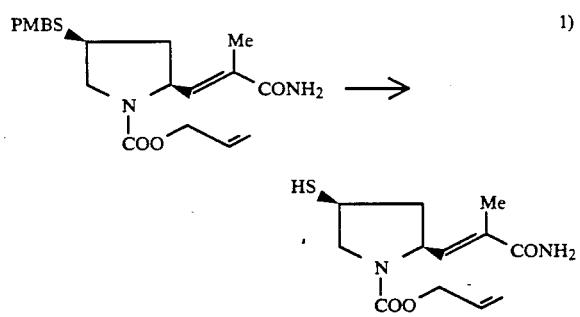

To a solution of (E)-3-[(2S,4S)-N-allyloxycarbonyl-4-(p-methoxyoenzyl)th:opyrrolidin-2-yl]-2-methylacrylamide (the compound cbtained in Reference Example 2-4); 445 mg, 1.27 mmol) in trifluoroacetic acid (2.0 ml) were added anisole (0.125 ml) and trifluoromethanesulfonic acid (0.5 ml) under ice-cooling under nitrogen. The reaction mixture was stirred for 45 minutes at the same temperature, and concentrated under reduced pressure, and the residue extracted with ethyl acetate (25 ml). The organic layer was washed successively with 1M pnospnate buffer (pH 5.7×3), and saturated aqueous sodium chloride, dried over anhydrous magnesium sulfate and concentrated to give a crude product containing (E)-3-[(2S,4S)-N-allyloxycarbonyl-4-mercaptopyrrolidin-2-yl]-2-methylacrylamide, which was used for the next reaction withour purification.

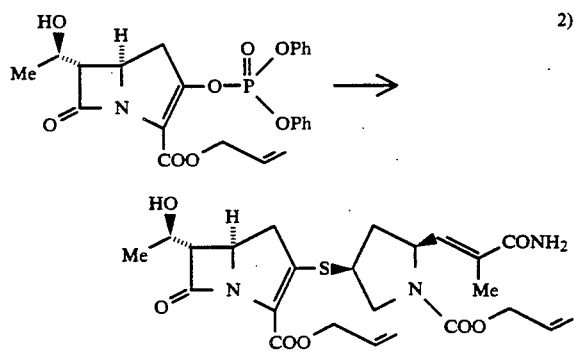

To a solution of allyl (5R,6S)-2-diphenoxyphosphoryloxy-6-[(R)-1-hydroxyethyl]-1-carbapen-2-em-3-carboxylate (300 mg, 0.62 mmol) in acetonitrile (10 ml)

were added N,N-diisopropylethylamine (0.113 ml, 0.65 mmol) and a solution of the crude thiol, obtained in the previous reaction, in acetonitrile (5 ml) under icecooling under nitrogen. The reaction mixture was stirred for 5.5 nours at the same temperature, and extracted with ethyl acetate (50 ml), and the organic layer washed successively with water and saturated aqueous sodium chloride, dried over anhydrous magnesium sulfate, and concentrated. The residue was purified by silica gel column chromatography (Wakogel ® C-300, elution with 5% methanol-chloroform) to give allyl (5R,6S)-2-[(2S,4S)-N-allyloxycaroonyl-2-[(E)-2-aminocarbonyl-2-methylvinyl]pyrrolidin-4-ylthio]-6-[(R)-1-hydroxyerhyl]-1-carbapen-2-em- 3-carboxylate (158 mg, 50.6% yield).

IR(KBr)cm$^{-1}$: 1780, 1700, 1640, 1410, 1330, 1130

NMR(CDCl$_3$) δ: 1.30(3H,d,J=6 Hz), 1.93(3H,br s), 5.16–5.54(4H,m), 5.94(2H,m), 6.14–6.48(3H,m)

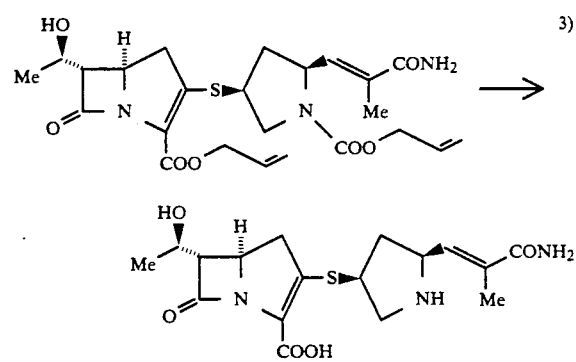

To a solution of the compound (158 mg, 0.31 mmol), obtained in the previous reaction, in methylene chloride (3.2 ml) were successively added water (28 μl), bis(triphenylphosphine)palladium (II) chloride (5 mg, 0.0071 mmol), and tributyltin hydride (0.37 ml, 1.38 mmol) under ice-cooling under nitrogen. The reaction mixture was stirred for 5 minutes under ice-cooling and for an additional 15 minutes at room temperature, and extracted with water (10 ml×2). The combined aqueous layer was washed with ethyl acetate (15 ml). The clarified filtrate was concentrated to ca. 10 ml and subjected to reverse phase column chromatography (LC-SORB ® SP-B-ODS, elution with 15% methanol-water). The fractions containing the desired compound were concentrated and lyophilized to give the title compound (47 mg, 39.4% yield).

IR(KBr)c$^{-1}$; 1760, 1680, 1650, 1600, 1390

NMR(D$_2$O) δ: 1.42(3H,d,J=6 Hz), 2.12(3H,br s), 2.53(2H,m), 6.49(1H,br d,J=8 Hz)

HPLC;
  Column: YMC ®-Pack ODS-A, 5 μ, 4.6 φ×150 mm.
  Eluent: 0.01M Phosphate buffer (pH 6.5)/MeOH (80/20).
  Flow rate: 1.5 ml/min.
  Column temperature: 40° C.
  Detector: UV 290 nm.
  Retention time : 1.98 min.

EXAMPLE 6

(1R,5S,6S)-2-[(2S,4S)-2-[(E)-2-Aminocarbonyl-2methylvinyl]pyrrolidin-4-ylthio]-6-[(R)-1-hydroxyethyl]-1-methyl-1-carbacen-2-em-3-carboxylic acid

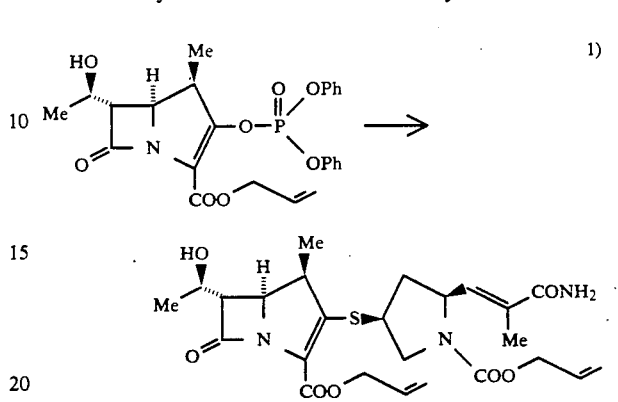

To a solution of allyl (1R,5S,6S)-2-diphenoxyphosphoryloxy-6-[(R)-1-hydroxyethyl]-1-methyl-1-carbapen-2-em-3-carboxylate (300 mg, 0.60 mmol) in acetonitrile (10 ml) were added N,N-diisopropylethylamine (0.11 ml, 0.63 mmol) and the crude thiol, obtained in the step 1) of Example 5, in acetonitrile under ice-cooling under nitrogen. The reaction mixture was stirred for 5.5 hours at the same temperature, and extracted with ethyl acetate (50 ml). The organic layer was washed successively with water and saturated aqueous sodium chloride, dried over anhydrous magnesium sulfate, and concenrrated. The residue was purified by silica gel column chromatography (Wakogel ® C-300, elution with 4% methanol-chloroform) to give allyl (1R,5S,6S-)-2-[(2S,4S)-N-allyloxycaroonyl-2-[(E)-2-aminocaroonyl-2-methylvinyl]pyrrolidin-4-ylthio]-6-[(R)-1-hydroxyethyl]-1-methyl-1-carbapen-2-em-3-carboxylate (154 mg, 49.3% yield).

IR(KBr)cm$^{-1}$; 1770, 1700, 1640, 1410, 1140

NMR(CDCl$_3$) δ: 1.26(3H,d,J=7 Hz), 1.35(3H,d,J=6 Hz), 1.96(3H, br s), 5.15–5.54(4H,m), 5.75–6.08(4H,m), 6.24(1H,br d,J=8 Hz)

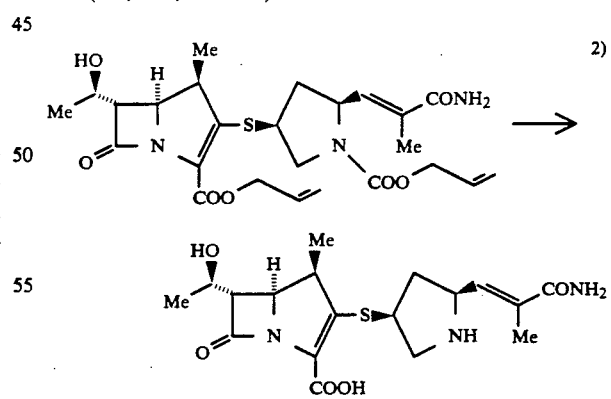

To a solution of the compound (154 mg, 0.30 mmol) obtained in the previous reaction, in methylene chloride (3.2 ml) were successively added water (27 μl), bis(triphenylphosphine)palladium (II) chloride (5 mg, 0.0071 mmol, and tributyltin hydride (0.35 ml, 1.30 mmol) under ice-cooling. The reaction mixture was stirred for 5 minutes at 0° C. and for an additional 15 minutes at room temperature, and extracted with water (10 ml)×2). The combined aqueous layer was washed with ethyl acetate (15 ml), and the clarified filtrate concentrated to ca. 10 ml, and subjected to reverse phase column chromatography (LC-SORB® SP-B-ODS, elution with 15% methanol-water). The fractions containing the desired compound were concentrated and lyophilized to give the title compound (54 mg, 46% yield).

IR(KBr)cm$^{-1}$: 1760, 1680, 1650, 1600, 1390

NMR((D$_2$O) δ: 1.38(3H,d,J=7 Hz), 1.45(3H,d,J=6 Hz), 2.13(3H,br s), 2.54(2H,m), 6.52(1H, br d,J=8 Hz)

HPLC; (the same condition as in Example 5)

Retention time: 3.22 min.

EXAMPLE 7

(1R,5S,6S) 2-[(2S,4S)-2-(Z)-2(Aminocarbonyl)vinyl]pyrrolidin-4-ylthio-6-[(R)-1-hydroxyethyl]-1-methyl-1-carbapen-2-em-3-carboxylic acid

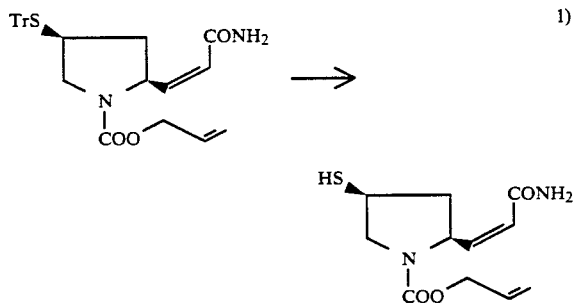

1)

To a solution of (Z)-3-[(2S,4S)-N-allyloxycarbonyl-4-tritylthiopyrrolidin-2-yl]acrylamide (1.02 g, 2.06 mmol) in methylene chloride (1 ml) were added trifluoroacetic acid (1 ml) and trietnylsilane (0.33 ml, 2.07 mmol) under ice-cooling under nitrogen. The reaction mixture was srirred for 30 minutes at the same temperature, concentrared under reduced pressure, and diluted with methylene chloride (5 ml). The mixture was concentrated again, and extracted with ethyl acetate (50 ml). The organic layer was washed with 0.1M phosphate buffer (pH 5.7×2) and saturated aqueous sodium chloride, dried over anhydrous magnesium sulfate, and concentrated to give (Z)-3 [(2S,4S)-N-allyloxycarbonyl-4-mercaptopyrrolidin-2-yl]acrylamide, which was used for the next reaction without purification.

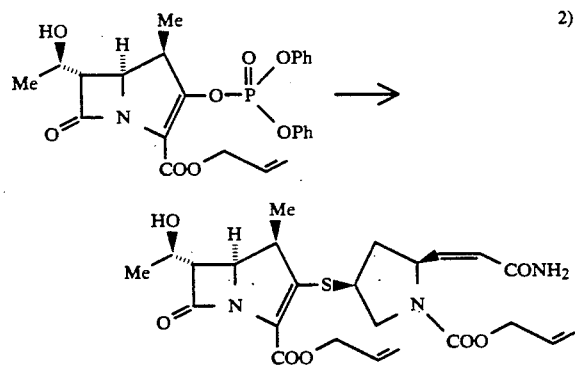

2)

To a solution of allyl (1R,5S,6S)-2-diphenoxyphosphoryloxy-6-[(R)-1-hydroxyethyl]-1-methyl-1-carbapen-2 em-3-carboxylate (650 mg, 1.3 mmol) in acetonitrile (20 ml) were dropwise added N,N-diisopropylethylamine (0.23 ml, 1.3 mmol) and a solution of the crude thiol, obtained in the previous reaction, in acetonitrile (10 ml) under ice-cooling under nitrogen. he reaction mixture was stirred for 6 hours at the same emperature, exrracred with ethyl acetate (100 ml). The organic layer was washed with water and saturated aqueous sodium chloride, dried over anhydrcus magnesium sulfate, and concentrated. The residue was purified cy silica gel column chromatography (Wakogel ® C-300, elution with 5% MeOH-CHCl$_3$, to give allyl (1R,5S,6S)-2-[(2S,4S)-N-allyloxycarbonyl-2-[(Z)-2-(aminocarbonylvinyl)pyrrolidin-4-ylthio]-6-[(R)-1-hydromethyl]-1-methyl-1-carbapen-2-em-3-carboxylate (236 mg, 35.9% y:eld).

IR(KBr)cm$^{-1}$: 1770, 1680, 1410

NMR(CDCl$_3$) δ: 1.26(3H,d,J-8 Hz), 1.33(3H,d,J=8 Hz), 5.12–5.53(4H,m), 5.74–6.24(4H,m)

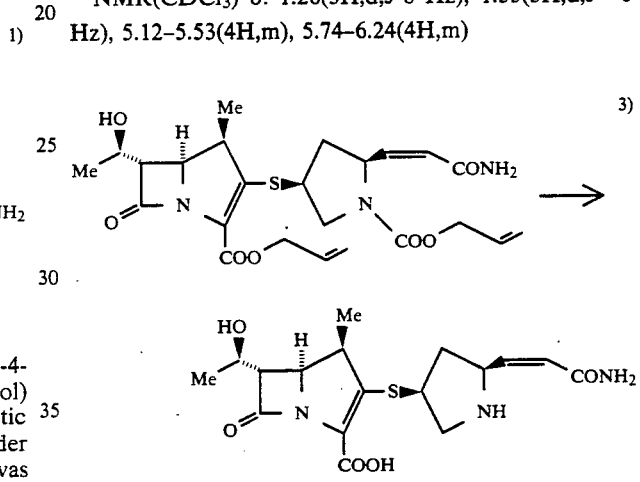

3)

To a solution of the compound (236 mg, 0.47 mmol) obtained in tne previous reaction, in methylene chloride (5 ml) were successively added water (42 μl), bis (triphenylphospnine)palladium (II) chloride (7.5 mg, 0.011 mmol) and tributyltin hydride (0.55 ml, 2.04 mmol) under ice-cooling. The reaction mixture was stirred for minutes at 0° C. and for an additional 15 minutes at room temperature, and extracted with water (10 ml). The aqueous layer was concentrated in vacuo to remove the methylene chloride. The residue was washed with ethyl acetate (15 ml), and the clarified filtrate, concentrated, and subjectedd to reverse pnase column chromatography (LC-SORB ® SP-B-ODS, elution with 10% methanol-water). The fractions containing rhe desired compound was ccncentrated and lyophilized to give the title compound (87 mg, 48% yield).

NMR((D$_2$O) δ: 1.38(3H,d,J=8 Hz), 1.45(3H,d,J=6 Hz), 2.03(1H,m), 3.06(1H,m), 3.44–3.58(3H,m), 3.92(1H,dd,J=12,6 Hz), 4.24(1H,m), 4.41(2H,m), 5.36(1H,q,J=8 Hz), 6.42(1H,d,J=12 Hz), 6.50(1H,dd,J=12,6 Hz)

HPLC; (the same cperation as in Example 5)

Retention time: 2.67min.

EXAMPLE 8

(1R,5S,6S)-2-[(2S,4S)-2-[(E)-2-(Aminocarbonyl)vinyl]-pyrrolidin-4-ylthio]-6-[(R)-1-hydroxyethyl]-1-methyl-1-carbapen-2-em-3-carboxylic acid

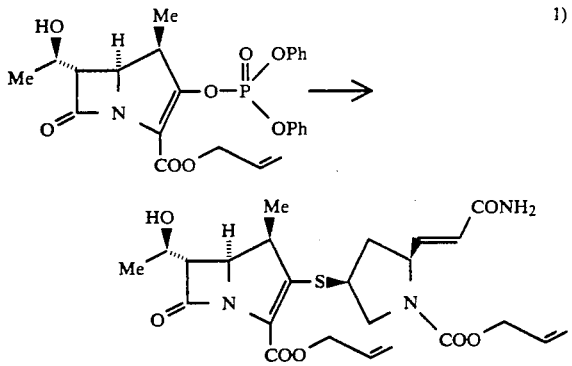

To a solution of allyl (1R,5S,6S)-2-diphenoxyphosphoryloxy-6-[(R)-1-hydroxyethyl]-1-methyl-1-carbapen-2-em-3-carboxylate (27.0 g, 54.06 mmol) and (E)-3-[(2S,4S)-N-allyloxycarbonyl-4-mercaptopyrrolidin-2-yl]acrylamide (16.63 g, 64.88 mmol) in acetonitrile (405 ml) was dropwise added N,N-diisopropylethylamine (9.42 ml, 54.06 mmol) at −30° C. over 15 minutes. The reaction mixture was stirred at −30° C. for 4 hours and at 5° C. for another 16 hours, partitioned between ethyl acerate (400 ml) and water (400 ml), and the eacn layer separated. The aqueous layer was treated with ethyl acerate (200 ml) for back exrraction, the combined organic layer washed successively with saturated aqueous sodium bicarbonate (300 ml) and saturated aqueous sodium chloride (300 ml), dried over anhydrous sodium sulfate and concentrated. The residue was purified by flash column chromatography on silica gel (Wakogel ® C-300, 400 ml; elution with ethyl acetate-acetone 7:3) to afford allyl (1R,5S,6S)-2-[(2S,4S)-N-allylcxycarbonyl-2-[(E)-2-(aminocarbonyl)vinyl]pyrrolidin-4-ylthio]-6-[(R)-1hydroxyethyl]-1-methyl-1-carbapen-2-em-3-carboxylate (22.64 g, 82.8% yield) as a foam powder.

NMR(CDCl$_3$) δ: 1.25(3H,d,J=6 Hz), 1.34(3H,d,J=7 Hz), 1.84(1H,m), 2.68(1H,m), 3.2–3.4(3H,m), 3.68(1H,m), 3.9–4.3(3H,m), 4.5–4.9(5H,m), 5.1–5.5(4H,m), 5.7–6.1(5H,m), 6.74(1H,dd,J=7,15 Hz)

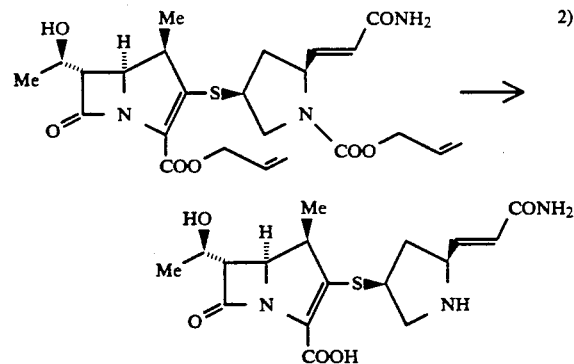

The compound (22.64 g, 44.78 mmol) obtained in the previous reaction was dissolved in methylene chloride (450 ml), treared with water (4.03 ml, 224 mmol), bis(-rriphenylphosphine)palladium (II) cnloride (629 mg, 0.896 mmol) and tributyltin hydride (31.32 ml, 116.4 mol) under ice-cooling. The reaction mixture was stirred tnere for 5 minutes and ar room temperature for another 15 minures, treated w:th water (400 ml, 100 ml×3) to evaporate the organic solvent in vacuo, and active charcoal (1 g) added thereto. The m:xture was stirred for 30 minutes and filtered by suction. The filtrate was concentrated to a weight of 66 g, treated dropwise with ethanol (540 ml) at room temperarure over 1.5 hours, and stirred for 30 minutes and at 5° C. for another 16 hours. The precipitate was collected by filtration, washed sequentially with 90% ethanol (20 ml×2) and acetone (60 ml), and dried in vacuo for 2 hours to afford the title compound (13.69 g, 80.1% yield).

NMR((D$_2$O) δ: 1.20(3H,d,J=7 Hz), 1.28(3H,d,J=6 Hz), 1.90(1H,ddd,J=6,8,14 Hz), 2.86(1H,ddd,J=7,7,14 Hz), 3.3–3.5(3H,m), 3.76(1H,dd,J=7,12 Hz), 4.08(1H,m), 4.2–4.3(2H,m), 4.44(1H,ddd,J=6,7,7 Hz), 6.34(1H,d,J=15 Hz), 6.82(1H,dd,J=7,15 Hz)

IR(KBr)cm$^{-1}$; 1750, 1690, 1650, 1610, 1450, 1400, 1290, 1270

EXAMPLE 9

(5R,6S)-6-[(R)-1-Hydroxyethyl]-2-[(2S,4S)-2-(E)-2-(N-methylaminocarbonyl)vinyl]pyrrolidin-4-ylthio]-1-carbapen-2-em-3-carboxylic acid

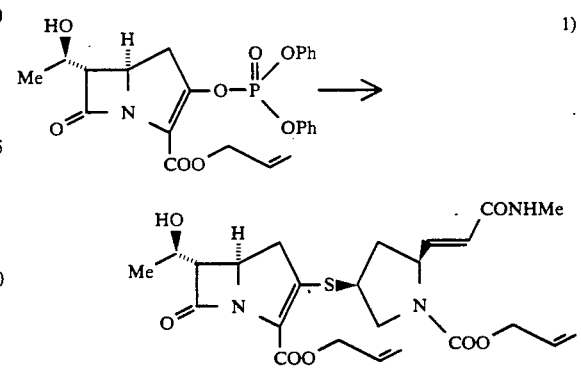

The same operation as in Example 8-1) was carried out by using allyl (5R,6S)-2-diphenoxyphosphoryloxy-6-[(R)-1-hydroxyerhyl]-1-carbapen-2-em-3-carboxylate (359 mg, 0.74 mmol), (E)-3-[(ZS,4S)-N-allyloxycarbonyl-4-mercapcopyrrolidin-2-yl-N-merhylacrylamide 200 mg, 0.74 mmol) and N,N-diisopropylethylamine (0.129 ml, 0.74 mmol) to obtain allyl (5R,6S)-2-[(2S,4S)-N-allyloxycarbonyl-2[(E)-2-(N-methylaminocarbonyl)-vinyl]pyrrolidin-4-ylthio]-1-carbapen-2-em-3-carboxylate (296 mg, 79.2% yield).

NMR(CDCl$_3$) δ: 1.34(3H,d,J=6 Hz), 1.84(1H,m), 2.64(1H,m), 2.88(3H,d,J=4 Hz), 3.0–3.4(4H,m), 3.62(1H,m), 4.0–4.3(3H,m), 5–4.9(5H,m), 5.1–5.5(4H,m), 5.7–6.1(4H,m), 6.7(1H,dd,J=7,15 Hz)

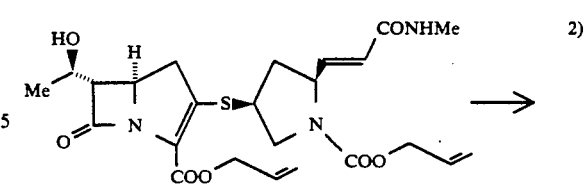

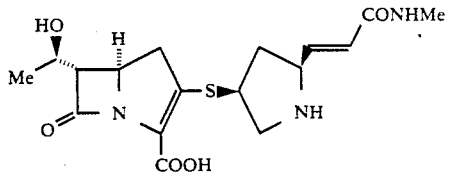

The same operation as in Example 8-2) was carried out by using the compound (296 mg, 0.585 mmol) cotained in the previous reaction, water 53 μl, 2.93 mmol), bis(triphenylphosphine)palladium (II) chloride (8.2 mg, 0.012 mmol) and tributyltin hydride (0.409 ml, 1.52 mmol) to obtain the title compound (160 mg, 71.7% yield) as a powder.

NMR((D$_2$O) δ: 1.27(3H,d,J=6 Hz), 1.94(1H,m), 2.7-2.9(1H,m), 2.82(3H,s), 3.20(2H,d,J=8 Hz), 3.46(2H,m), 3.83(1H,dd,J=8,12 Hz), 4.08(1H,m), 4.2(2H,m), 4.4(1H,m), 6.32(1H,d,J=15 Hz), 6.75(1H,dd,J=8,15 Hz)

IR(KBr)cm$^{-1}$; 1770, 1680, 1630, 1550, 1440, 1400, 1290, 1280, 1230

EXAMPLE 10

(1R,5S,6S)-6-[(R)-1-Hydroxyethyl]-1-methyl-2-[(2S,4S)-2-(E)-2-(N-methylaminocarbonyl)vinyl]pyrrolidin-4-ylthio]-1-carbacen-2-em-3-carboxylic acid

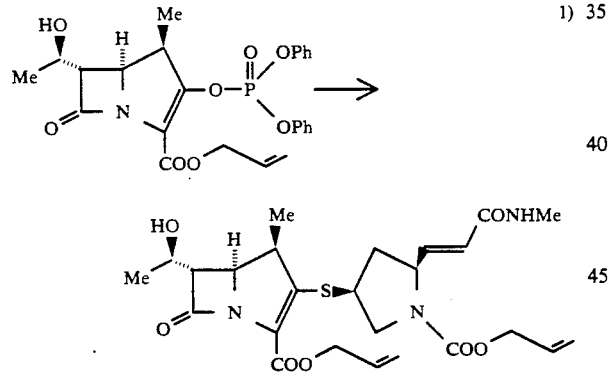

The same operation as in Example 8-1) was carried out by using allyl (1R,5S,6S)-2-diphenoxyphosphoryloxy-6-[(R)-1-hydroxyerhyl]-1-methyl-1-carbapen-2-em-3-carboxylate 776 mg, 1.55 mmol), (E)-3-[(2S,4S)-N-allyloxycarbonyl-4-mercaptopyrrolidin-2-yl]-N-methylacrylamide (420 mg, 1.55 mmol) and N,N-diisopropylethylamine 0.27 ml, 1.55 mmol) to obtain allyl (1R,5S,6S)-2-[.2S,4S)-N-allyloxycarbonyl-2-[(E)-2-(N-methylaminocarbonyl)vinyl]pyrrolidin-4-ylthio]-1-methyl-1-caroapen-2-em-3-carboxylate (256 mg, 31.7% yield) as a foam powder.

NMR(CDCl$_3$) δ: 1.26 (3H,d,J=7 Hz), 1.36(3H,d,J=6 Hz), 1.84(1H,m), 2.64(1H,m), 2.89(3H,d,J=4 Hz), 3.2-3.4(3H,m), 3.69(1H,m), 3.9-4.3(3H,m), 4.5-4.9(5H,m), 5.1-5.5(4H,m), 5.7-6.1(4H,m), 6.72(1H,dd,J=7,15 Hz)

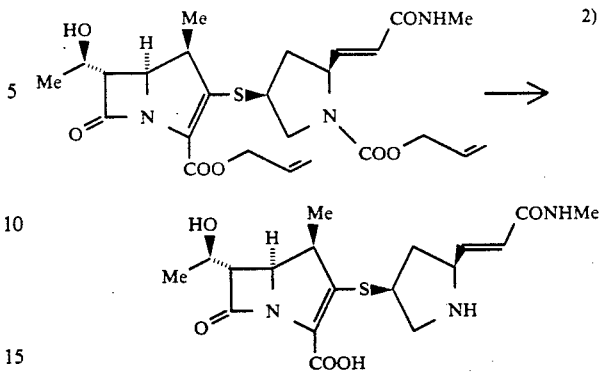

The same operation as in Example 8-2) was carried out by using the compound (256 mg, 0.49 mmol obtained in the previous reaction, water (45 μl, 2.46 mmol), bis(triphenylphosphine)palladium (II) chloride (7 mg, 0.01 mmol) and tributyltin hydride (0.345 ml, 1.28 mmol) to obtain the title compound (83 mg, 42.6% yield) as a powder.

NMR((D$_2$O) δ: 1.22 (3H,d,J=7 Hz), 1.28(3H,d,J=6 Hz), 1.90(1H,ddd,J=7,9,16 Hz), 2.75-2.9(1H,m), 2.82(3H,s), 3.3-3.5(3H,m), 3.76(1H,dd,J=7,12 Hz), 4.04(1H,m), 4.22(2H,m), 4.40(1H,brq,J=7 Hz), 6.32(1H,d,J=15 Hz), 6.77(1H,dd,J=7,15 Hz)

IR(KBr)cm$^{-1}$; 1760, 1680, 1630, 1580, 1450, 1390, 1280, 1260

EXAMPLE 11

(5R,6S)-6-[(R)-1-Hydroxyethyl]-2-[(2S,4S)-2-[(E)-2-oxopyrrolidin-3-ylidene)methyl]pyrrolidin-4-ylthio]-1-carbapen-2-em-3-carboxylic acid

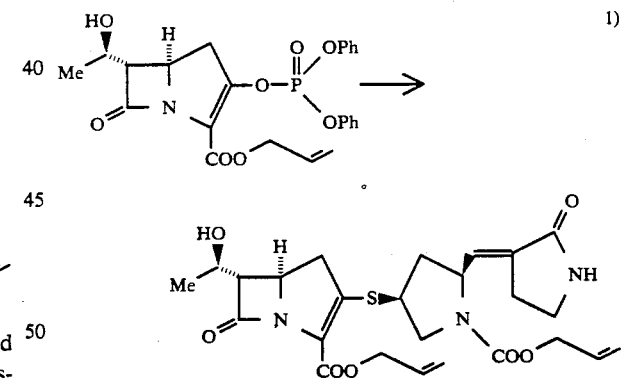

The same operation as in Example 8-1) was carried out by using allyl (5R,6S)-2-diphenoxyphosphoryloxy-6-[(R)-1-hydroxyethyl]-1-carbapen-2-em-3-carboxylate (378 mg, 0.779 mmol), (2S,4S)-N-allyloxycarbonyl-4-mercapto-2-[(E)-(2-oxopyrrolidin-3-ylidene)methyl]pyrrolidine (220 mg, 0.779 mmcl) and N,N-diisopropylethylamine (0.136 ml, 0.779 mmol) to obtain allyl (5R,6S)-2-[(2S,4S)-N-allyloxycarbonyl-2-[(E)-(2-oxopyrrolidin-3-ylidene)metnyl]pyrrolidin 4-ylthio]-1-carbapen-2-em-3-carboxylate (276 mg, 68.5% yield) as a foam powder.

NMR(CDCl$_3$) δ: 1.35(3H,d,J=7 Hz), 1.8(1H,m), 2.5-2.9(2H,m), 3.0-3.6(8H,m), 4.1-4.3(1H,m), 4.4-4.9(5H,m), 5.2-5.5(4H,m), 5.8-6.2(3H,m), 6.35(1H,m)

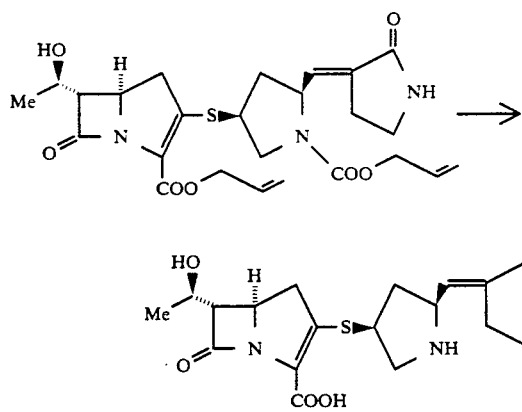

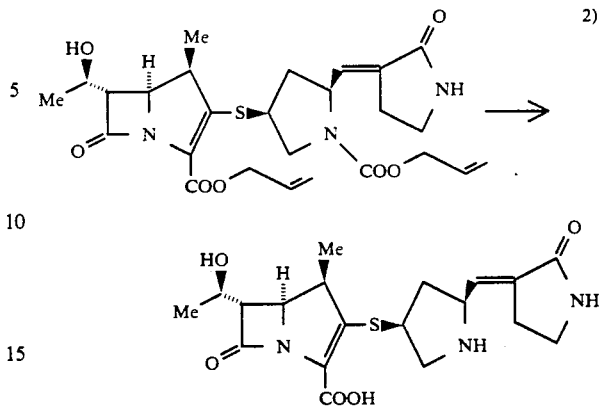

The same operation as in Example 8-2) was carried out by using the compound (276 mg, 0.533 mmol) obtained in the previous reaotion, water (48 [l, 2.7 mmol), bis(triphenylphosphine)palladium (II) chloride (7.5 mg, 0.01 mmol) and tributyltin hydride (0.372 ml, 1.39 mmol) to obtain the title compound (147 mg, 70.0% yield) as a powder.

NMR($D_2O$-$CD_3OD$) δ: 1.23 (3H,d,J=6 Hz), 1.9(1H,m), 2.7–2.9(3H,m), 3.16(2H,d,J=8 Hz), 3.37(2H,m), 3.48(2H,brt,J=6 Hz), 3.78(1H,dd,J=8,12 Hz), 4.02(1H,m), 4.18(2H,m), 4.44(1H,brq,J=8 Hz), 6.32(1H,dt,J=8,2 Hz)

IR(KBr)cm$^{-1}$: 1750, 1680, 1610, 1580, 1390

EXAMPLE 12

(1R,5S,6S)-6-[(R)-1-Hydroxyethyl]-1-methyl-2-[(2S,4S)-2[(E)-(2-oxopyrrolidin-3-ylidene)methyl]pyrrolidin-4-ylthio]-1-carbaoen-2-em-3-carboxylic acid The same operation as in Example 8-2) was carried out by using the compound (3.48 g, 6.55 mmol) obtained in the previous reaction, water (0.589 ml, 32.7 mmol), bis(triphen/lphosphine)palladium (II) chloride (92 mg, 0.13 mmol) and tributyltin hydride (5.28 ml, 19.6 mmol) to obtain the title compound (1.95 g, 73.3% yield) as a powder.

NMR(($D_2O$) δ: 1.24(3H,d,J=7 Hz), 1.30(3H,d,J=6 Hz), 1.92(1H,m), 2.8–3.0(3H,m), 3.3–3.6(5H,m), 3.78(1H,dd,J=8,12 Hz), 4.12(1H,m), 4.28(2H,m), 4.52(1H,brq,J=8 Hz), 6.42(1H,dt,J=8,2 Hz)

IR(KBr)cm$^{-1}$: 1760, 1680, 1620, 1580, 1450, 1390, 1310, 1280

EXAMPLE 13

1R,5S,6S)-6-[(R)-1-Hydroxyethyl]-1-methyl-2-(2S,4S)-2-(Z)-(2-oxopyrrolidin-3-ylidene)methylpyrrolidin-4-ylthio]-1-carbaoen-2-em-3-carboxylic acid

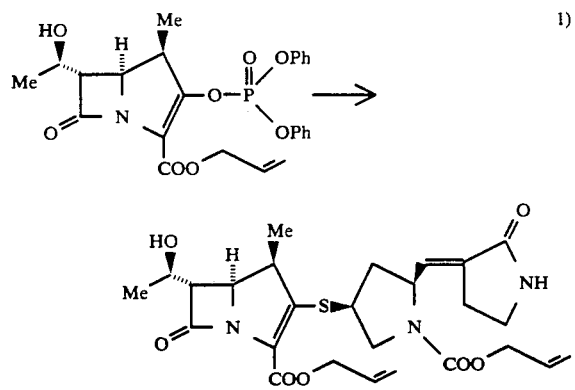

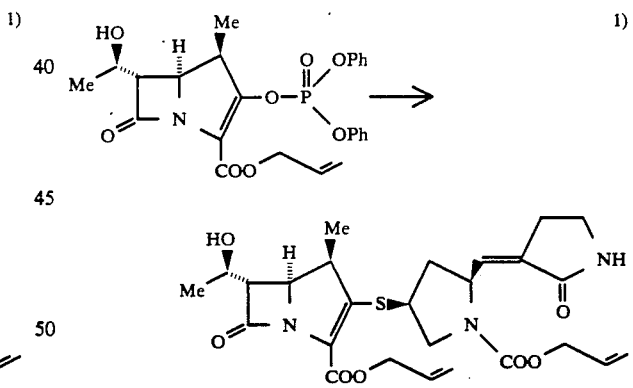

The same operation as in Example 8-1) was carried out by using allyl (1R,5S,6S)-2-diphenoxyphosphoryloxy-6-[(R)-1-hydroxyethyl],-1-methyl-1-carbapen-2-em-3-carboxylate 5.34 g, 10.69 mmol), (2S,4S)-N-allyloxycaroonyl-4-mercapro-2-[(E)-(2-oxopyrrolidin-3ylidene)metnyl]pyrrolidin (3.02 mg, 10.69 mmol) and N,N-diisopropylethylamine (1.86 ml, 10.69 mmol) to obtain allyl (1R,5S,6S)-2-[(2S,4S)-N-allyloxycarbonyl-2-[(E)-(2-oxopyrrolidin-3-ylidene)methyl]pyrrclidin-4-ylthio]-1-methyl-1-carbapen-2-em-3-carboxylate (3.48 g, 61.2% yield) as a foam powder.

NMR(CDCl$_3$) δ: 1.27(3H,d,J=7 Hz), 1.36 (3H,dJ=7 Hz), 1.8(1H,m), 2.5–2.9(2H,m), 3.2–3.5(6H,m), 3.65(1H,m), 4.0–4.3(3H,m), 4.5–4.9(5H,m), 5.2–5.5(4H,m), 5.8–6.2(3H,m), 6.35(1H,ors)

The same operation as in Example 8-1) was carr;ed out by using allyl (1R,5S,6S)-2-diphenoxyphosphoryloxy-6-(R)-1-hydroxyethyl]-1-methyl-1-carbapen-2-em-3-carboxylate (990 mg, 1.98 mmol), (2S,4S)-N-allyloxycarbonyl-4-mercapto-2-[(Z)-(2-oxopyrrolidin-3ylidene)methyl]pyrrolidine (560 mg, 1.98 mmol) and N,N-diisopropylethylamine (0.345 ml, 1.98 mmol) to obtain allyl (1R,5S,6S)-2-[(2S,4S)-N-allyloxycarbonyl-2-[(Z)-(2-oxopyrrolidin-3-ylidene)methyl]pyrrolidin-4-ylthio]-1-methyl-1-caroapen-2-em-3-carboxylate (443 mg, 42.0% yield) as a foam powder.

NMR(CDCl$_3$) δ: 1.28(3H,d,J=7 Hz), 1.36(3H,d,J=6 Hz), 1.8(1H,m), 2.7–2.9(2H,m), 3.3–3.5(6H,m), 3.66(1H,m), 4.0–4.3(3H,m), 4.5–4.9(4H,m), 5.1–5.5(4H,m), 5.7–6.1(5H,m)

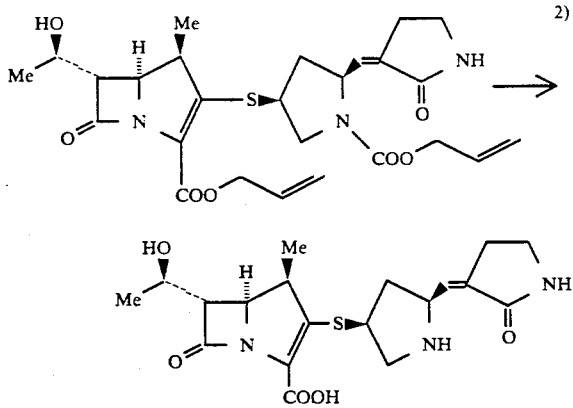

The same operation as in Example 8-2) was carried out by using the compound (440 mg, 0.828 mmol) obtained in the previous reaction, water (75 μl, 4.14 mmol), bis(triphenylphosphine)palladium (II) chloride (12 mg, 0.017 mmol) and tributyltin hydride (0.668 ml, 2.48 mmol) to obtain the title compound (165 mg, 48.9% yield) after purification by reverse phase column chromatography (YMC.GEL® ODS-AQ 120-S50, 50 ml; elution with methanol-water 1:4), concentration of fractions including the desired product and lyophilization.

NMR((D$_2$O) δ: 1.21(3H,d,J=6 Hz), 1.28(3H,d,J=6 Hz), 1.84(1H,m), 2.7-2.9(3H,m), 3.3-3.5(5H,m), 3.74(1H,dd,J=8,12 Hz), 4.06(1H,m), 4.1-4.3(2H,m), 5.42(1H,brq,J=8 Hz), 6.09(1H,brd,J=8 Hz)

IR(KBr)cm$^{-1}$: 1750, 1690, 1670, 1600, 1450, 1400, 1290

EXAMPLE 14

(5R,6S)-2-[(2S,4S)-2-[(E)-2-(N,N-dimethylaminocarbonyl)vinyl]pyrrolidin-4-ylthio-6-[(R)-1-hydroxyethyl]-1-carbapen-2-em-3-carboxylic acid

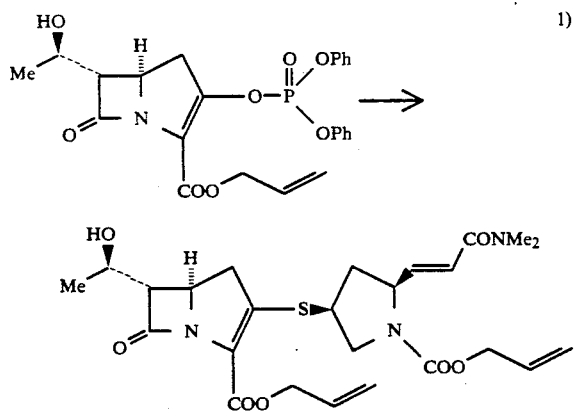

The same operation as in Example 8-1) was carried out by using allyl (5R,6S)-2-diphenoxyphosphoryloxy-6-[(R)-1-hydroxyethyl]-1-carbapen-2-em-3-carboxylate (485 mg, 1.00 mmol), (E)-3-[(2S,4S)-N-allyloxycarbonyl-4-mercaptopyrrolidin-2-yl]-N,N-dimethylacrylamide (284 mg, 1.0 mmol) and N,N-diisopropylethylamine (0.174 ml, 1.0 mmol) to obtain allyl (5R,6S)-2-[(2S,4S)-N-allyloxycarbonyl-2-[(E)-2-(N,N-dimethylaminocarbonyl)vinyl]pyrrolidin-4-ylthio]-1carbapen 2 em-3-carboxylate (330 mg, 63.5% yield) as a foam powder.

NMR(CDCl$_3$) δ: 1.35(3H,d,J=7 Hz), 1.86(1H,m), 2.65(1H,m), 3.0(3H,s), 3.06(3H,s), 3.1-3.3(4H,m), 3.6(1H,m), 4.1-4.3(3H,m), 4.5-4.9(5H,m), 5.2-5.5(4H,m), 5.96(2H,m), 6.36(1H,d,J=16 Hz), 6.7(1H,m)

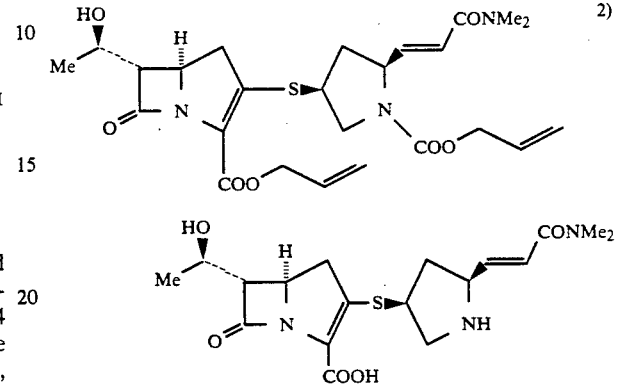

The same operation as in Example 8-2) was carried out by using the compound (330 mg, 0.635 mmol) obtained in the previous reaction, water (57 μl, 3.18 mmol), bis(triphenylphosphine)palladium (II) chloride (9.0 mg, 0.013 mmol) and tributyltin hydride (0.512 ml, 1.91 mmol) to obtain the title compound (140 mg, 55.7% yield) as a powder.

NMR((D$_2$O) δ: 1.29(3H,d,J=6 Hz), 2.0(1H,m), 2.86(1H,m), 3.01(3H,s), 3.14(3H,s), 3.23(2H,d,J=9 Hz), 3.45(1H,dd,J=3,6 Hz), 3.47(1H,dd,J=6,12 Hz), 3.85(1H,dd,J=8,12 Hz), 4.1(1H,m), 4.25(2H,m), 4.45(1H,m), 6.7(1H,dd,J=7,16 Hz), 6.82(1H,d,J=16 Hz)

IR(KBr)cm$^{-1}$: 1770, 1670, 1610, 1400, 1260

EXAMPLE 15

(1R,5S,6S)-2-[(E)-2-(N,N-Dimethylaminocarbonyl)-vinyl]pyrrolidin-4-ylthio]-6-[(R)-1-hydroxyethyl]-1-methyl-1-carbapen-2-em-3-carboxylic

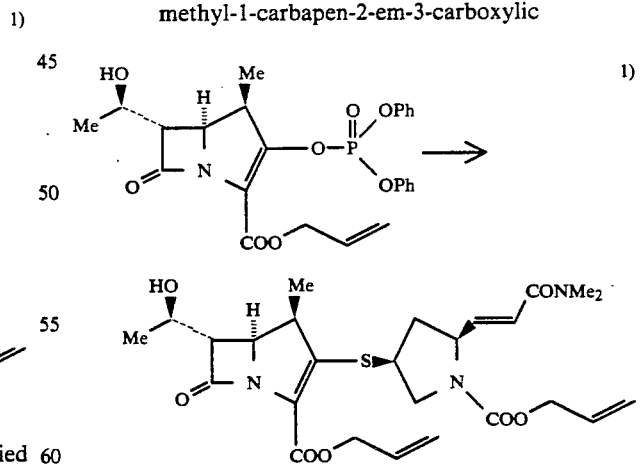

The same operation as in Example 8-1) was oarried out by using allyl (1R,5S,6S)-2-diphenoxyphosphoryloxy-6-(R)-1-hydroxyethyl]-1-methyl-1-carbapen-2-em-3-carboxylate (1.17 g, 2.34 mmol), (E)-3-[(2S,4S)-N-allyloxycarbonyl-4-mercaptopyrrolidin-2-yl]-N,N-dimethylacrylamide (730 mg, 2.34 mmol) and N,Ndiisopropylethylamine (0.406 ml, 2.34 mmol) to obtain allyl (1R,5S,6S)-2-[(2S,4S)-N-allyloxycarbonyl-2-[(E)-(N,N-dimethylaminocarbonyl)vinyl]pyrrolidin-4-ylthio]-1-methyl-1-carbapen-2-em-3-carboxylate (673 mg, 54.1% yield) as a foam powder.

NMR(CDCl₃) δ: 1.28(3H,d,J=7 Hz), 1.36(3H,d,J=7 Hz), 1.86(1H,m), 2.66(1H,m), 3.01(3H,s), 3.08(3H,s), 3.2–3.4(3H,m), 3.66(1H,m), 4.1–4.3(3H,m), 4.5–4.9(5H,m), 6.2–6.5(4H,m), 5.8–6.1(2H,m), 6.38(1H,d,J=15 Hz), 6.72(1H,m)

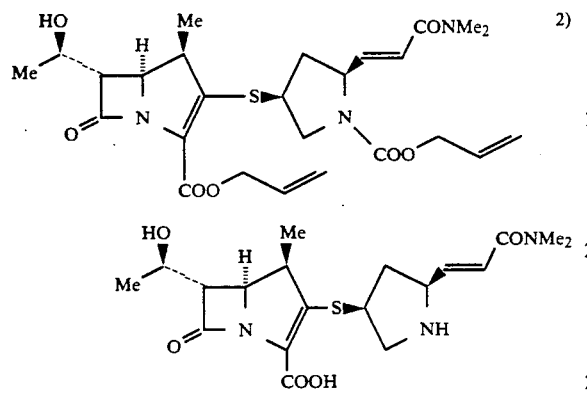

The same operation as in Example 8-2) was carried out by using the compound (673 mg, 1.26 mmol) obtained in the previous reaction, water (0.113 ml, 6.31 mmol), bis(triphenylphosphine)palladium (II) chloride (17.7 mg, 0.025 mmol) and tributyltin hydride (1.02 ml, 3.78 mmol) to obtain the title compound (373 mg, 72.2% yield) as a powder.

NMR(D₂O) δ: 1.26(3H,d,J=7 Hz), 1.3(3H,d,J=7 Hz), 2.0(1H,m), 3.9(1H,m), 3.0(3H,s), 3.18(3H,s), 3.3–3.5(3H,m), 3.8(1H,dd,J=8,12 Hz), 4.1(1H,m), 4.26(2H,m), 4.47(1H,m), 6.72(1H,dd,J=6,16 Hz), 6.82(1H,d,J=16 Hz)

IR(KBr)cm⁻¹: 1760, 1670, 1610, 1400, 1260

EXAMPLE 16

(1R,5S,6S)-6-[(R)-1-Hydroxyethyl]-1-methyl-2-[(2S,4S)-2[-(E)-2-(piperazinylcarbonyl)vinyl]pyrrolidin-4-ylthio]-1-carbapen-2-em-3-carboxylic acid

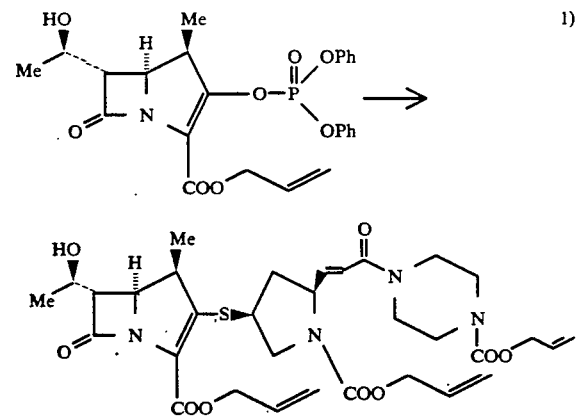

The same operation as in Example 8-1) was carried out by using allyl (1R,5S,6S)-2-diphenoxyphosphoryloxy-6[-(R)-1-hydroxyethyl]-1-methyl-1-carbapen-2-em-3-carboxylate (1.0 g, 2.0 mmol), (2S,4S)-N-allyloxycarbonyl-2-[(E)-2-[4(allyloxycarbonyl)-piperazinylcarbonyl]vinyl]-4mercaptopyrrolidine (820 mg, 2.0 mmol) and N,Ndiisopropylethylamine (0.35 ml, 2.0 mmol) to obtain allyl (1R,5S,6S)-2-[(2S,4S)-N-allyloxycarbonyl-2-[(E)-2-[4(allyloxycarbonyl)-piperazinylcarbonyl]piperazinylcarbonyl]vinyl]pyrrolidin-4ylthio]-1-methyl-1-carbapen-2-em-3-carboxylate (440 mg, 32.7% yield) as a foam powder.

NMR(CDCl₃) δ: 1.26(3H,d,J=7 Hz), 1.35(3H,d,J=6 Hz), 1.9(1H,m), 2.6(1H,m), 3.2–3.7(12H,m), 4.0–4.3(3H,m), 4.5–4.9(7H,m), 5.2–5.5(6H,m), 5.9(3H,m), 6.35(1H,d,J=15 Hz), 6.7(1H,m)

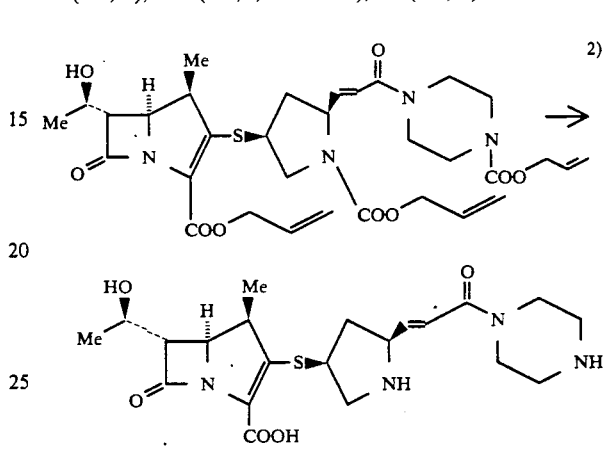

The same operation as in Example 8-2) was carried out by using the compound (440 mg, 0.65 mmol) obtained in the previous reaction, water (88 μl, 4.9 mmol), bis(triphenylphosphine)palladium (II) chloride (9.2 mg, 0.013 mmol) and tributyltin hydride (1.05 ml, 3.9 mmol) to obtain the title compound (147 mg, 49.9% yield) after purification by reverse phase column chromatography (YMC-GEL® ODS-AQ 120-S50, 50 ml; elution with methanol-water 1:4), concentration of fractions including the desired product and lyophilization.

NMR(D₂O) δ: 1.2(3H,d,J=6 Hz), 1.28(3H,d,J=6 Hz), 1.62(1H,m), 2.66(1H,m), 3.16(4H,br s), 3.3–3.5(3H,m), 3.7–4.0(6H,m), 4.05(1H,q,J=7 Hz), 3.2–3.3(2H,m), 6.62(1H,d,J=15 Hz), 6.79(1H,dd,J=6,15 Hz)

IR(KBr)cm⁻¹: 1760, 1600, 1450, 1380, 1270

REFERENCE EXAMPLE 1

(2S,4S)-N-Allyloxycarbonyl-2-hydroxymethyl-4-mercaptopyrrolidine

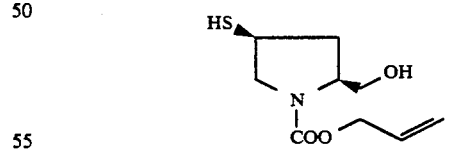

REFERENCE EXAMPLE 1-1)

L-Hydroxyproline methyl ester hydrochloride

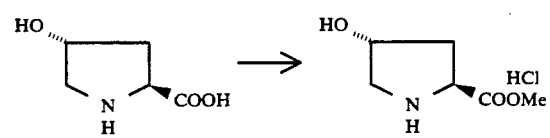

To a solution of hydrogen chloride-methanol prepared from acetyl chloride (19 ml, 270 mmol) and methanol (170 ml) was added L-hydroxyproline (25 g, 190 mmol), and the reaction mixture refluxed for 7 hours with stirring, cooled to room temperature. The mixture was stirred at 5° C. for 1 hour after addition of diethyl ether (340 ml). The resulting precipitate was collected by filtration, washed with a solution of diethyl ether-methanol (2:1, 50 ml), and dried under nitrogen for 4 hours to afford the title compound (30.64 g, 89% yield).

NMR(DMSO-d$_6$) δ: 2.14(2H,m), 3.1(1H,d,J=12 Hz), 3.4(1H,dd,J=4,12 Hz), 3.82(3H,s), 4.48(2H,m), 5.66(1H,brs), 9.9(2H,brs)

REFERENCE EXAMPLE 1-2)

(2S,4R)-N-Allyloxycarbonyl-4-hydroxyproline methyl ester

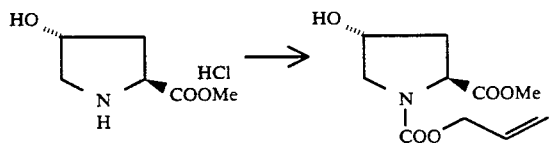

A mixture of L-hydroxyproline methyl ester hydrochloride (the compound obtained in Reference Example 1-1); 24.37 g, 134 mmol) and triethylamine (41.2 ml, 295 mmol) in methylene chloride (240 ml) was stirred at room temperature for 10 minutes, cooled to −5° C., treated dropwise with a solution of allyl chloroformate (14.9 ml, 140 mmol) in methylene chloride (30 ml). The reaction mixture was stirred at −5° C. for 1 hour, and washed twice with water. The organic layer was dried over anhydrous sodium sulfate and evaporated to afford the title compound (30.8 g, 100% yield) as an oil.

NMR(CDCl$_3$) δ: 2.1(1H,m), 2.35(1H,m), 3.65(2H,m), 3.74(1.5H,s), 3.77(1.5H,s), 4.55(4H,m), 5.3(2H,m), 5.9(1H,m)

REFERENCE EXAMPLE 1-3)

(2S,4R)-N-Allyloxycarbonyl-4-methanesulfonyloxyproline methyl ester

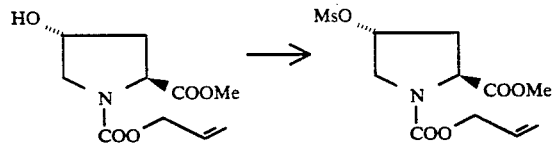

To a solution of (2S,4R)-N-allyloxycarbonyl-4-hydroxyproline methyl ester (the compound obtained in Reference Example 1-2); 50.15 g, 219 mmol) and triethylamine (45.8 ml, 328 mmol) in methylene chloride (480 ml) was dropwise added a solution of methanesulfonyl chloride (20.3 ml, 262 mmol) in methylene chloride (20 ml) at from 0° to 5° C. The reaction mixture was stirred at from 0° to 5° C. for 30 minutes, washed successively with water (100 ml, twice), saturated sodium bicarbonate (100 ml) and saturated sodium chloride (100 ml), dried over anhydrous sodium sulfate, and evaporated in vacuo to afford the title compound (67.2 g, 100% yield) as an oil.

NMR(CDCl$_3$) δ: 2.3(1H,m), 2.65(1H,m), 3.06(3H,s), 3.75(1.5H,s), 3.78(1.5H,s), 3.85(2H,m), 4.55(3H,m), 5.3(3H,m), 5.9(1H,m)

REFERENCE EXAMPLE 1-4)

(2S,4R)-N-Allyloxycarbonyl-2-hydroxymethyl-4-methanesulfonyloxypyrrolidine

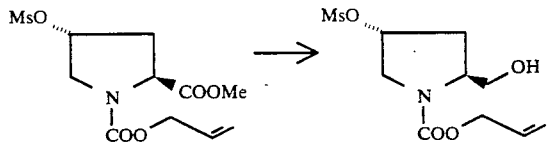

To a solution of lithium chloride (18.55 g, 437 mmol) and (2S,4R)-N-allyloxycarbonyl-4-methanesulfonyloxyproline methyl ester (67.2 g, 219 mmol) in tetrahydrofuran (280 ml) were successively added sodium borohydride (16.55 g, 437 mmol) and ethanol (420 ml) in one portion. The reaction mixture was stirred at room temperature for 5 hours, cooled to 5° C., treated carefully with acetic acid (25 ml, 437 mmol) to quench the reaction. The solvents were evaporated in vacuo, and the residue partitioned between ethyl acetate (300 ml) and water (300 ml). The organic layer was washed with saturated aqueous sodium chloride, dried over anhydrous sodium sulfate, and evaporated to afford the title compound (56.26 g, 92% yield) as an oil.

NMR(CDCl$_3$) δ: 2.05(1H,m), 2.4(1H,m), 3.05(3H,s), 3.65(2H,m), 3.9(2H,m), 4.15(1H,m), 4.63(2H,d,J=5 Hz), 5.3(3H,m), 5.95(1H,m)

REFERENCE EXAMPLE 1-5)

(2S,4S)-4-Acetylthio-N-allyloxycarbonyl-2-hydroxymethylpyrrolidine

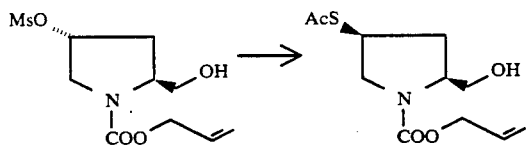

To a solution of sodium hydride (50% dispersion in mineral oil, 9.5 g, 198 mmol) in N,N-dimethylformamide (400 ml) was added thiolacetic acid (18.2 ml, 257 ml, 257 mmol), followed by stirring at room temperature for 30 minutes. The reaction mixture was treated successively with sodium iodide (35.58 g, 237 mmol) and a solution of (2S,4R)-N-allyloxycarbonyl-2-hydroxymethyl-4-methanesulfonyloxypyrrolidine (the compound obtained in Reference Example 1-4); 55.26 g, 198 mmol) in N,N-dimethylformamide (100 ml), followed by stirring at 70° C. for 5 hours, partitioned between ethyl acetate (500 ml) and water (2 l), and the each layer separated. The aqueous layer was treated with ethyl acetate (250 ml) for back extraction, the combined organic layer washed successively with water (1 l), 10% aqueous sodium bicarbonate (500 ml) and saturated aqueous sodium chloride (500 ml), dried over anhydrous sodium sulfate, and evaporated. The residue was subjected to flash column chromatography on silica gel (Wakogel ® C-300, 600 elution with ethyl acetate-hexane 1:4 2:3) to afford the title compound (30.63 g, 60% yield) as an oil.

NMR(CDCl$_3$) δ: 2.34(3H,s), 2.45(2H,m), 3.22(1H,dd,J=8,11 Hz), 3.74(2H,br s), 3.88(1H,m), 4.1(2H,m), 4.62(2H,d,J=5 Hz), 5.26(2H,dd,J=2,10 Hz), 5.34(1H,dd,J=2,17 Hz), 5.94(1H,ddt,J=10,17,5 Hz)

REFERENCE EXAMPLE 1-6)

(2S,4S)-N-Allyloxycarbonyl-2-hydroxymethyl-4-mercaptopyrrolidine

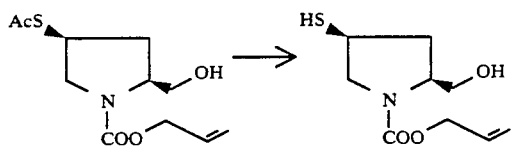

A solution of (2S,4S)-4-acetylthio-N-allyloxycarbonyl-2-hydroxymethylpyrrolidine (1.17 g, 4.5 mmol) in methanol (25 ml) was treated with 2N sodium hydroxide solution (4.95 ml) under ice-cooling, followed by stirring for 30 minutes, and partitioned between 6N hydrochloric acid (1.65 ml) and ethyl acetate (100 ml). The organic layer was washed with saturated aqueous sodium chloride (30 ml×3), dried over anhydrous sodium sulfate, and evaporated to afford the title compound (875 mg, 90% yield) as an oil.

REFERENCE EXAMPLE 2

(E)-3-[(2S,4S)-N-Allyloxycarbonyl-4-(p-methoxybenzylthio)pyrrolidin-2-yl]-2-methylacrylamide

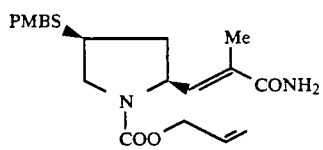

REFERENCE EXAMPLE 2-1)

(2S,4S)-4-Acetylthio-N-allyloxycarbonylproline methyl ester

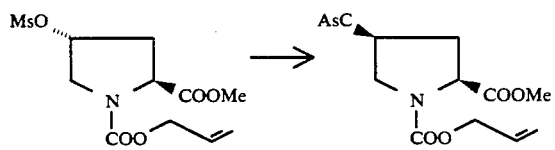

A solution of (2S,4R)-N-allyloxycarbonyl-4-methanesulfonyloxyproline methyl ester (the compound obtained in Reference Example 1-3); 13.3 g, 49.8 mmol) in N,N-dimethylformamide (120 ml) was treated with sodium iodide (2.6 g, 17.3 mmol) and potassium thioacetate (8.54 g, 74.8 mmol) at room temperature under nitrogen. After being stirred overnight from 60° to 70° C. The reaction mixture was extracted with ethyl acetate (500 ml), and the organic layer washed successively with water (×3) and saturated aqueous sodium chloride, dried over anhydrous sodium sulfate, and concentrated. The residue was purified by silica gel column chromatography (Wakogel ® C-300, elution with 10% ethyl acetate/hexane) to give the title compound (10.28 g, 71.9% yield).

NMR(CDCl$_3$) δ: 2.02(1H,m), 2.34(3H,s), 2.77(1H,m), 3.42(1H,m), 3.78(3H,s), 4.05(2H,m), 4.44(1H,m), 4.62(2H,m), 5.30(2H,m), 5.92(1H,m)

REFERENCE EXAMPLE 2-2)

(2S,4S)-N-Allyloxycarbonyl-4-(p-methoxybenzylthio)-proline methyl ester

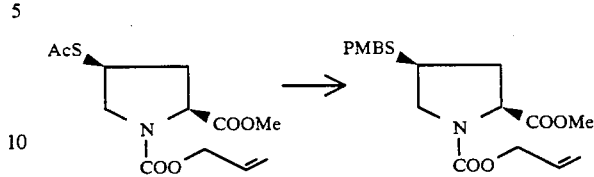

A solution of (2S,4S)-4-acetylthio-N-allyloxycarbonylproline methyl ester (the compound obtained in Reference Example 2-1); 10 g, 34.8 mmol) in methanol (100 ml) was dropwise treated with 1N sodium hydroxide (34.8 ml) under ice-cooling under nitrogen, and stirred there for 15 minutes at the same temperature. Triethylamine (5.1 ml, 36.7 mmol) and p-methoxybenzyl chloride (6.8 ml, 50.0 mmol) were added to the reaction mixture under ice-cooling. After being stirred for 2 hours, the reaction mixture was concentrated in vacuo, and the residue extracted with ethyl acetate (300 ml). The organic layer was washed with saturated aqueous sodium chloride, dried over anhydrous sodium sulfate and concentrated. The residue was purified by silica gel column chromatography (Wakogel ® C-300, elution with 20% hexane-ethyl acetate) to give the title compound (10 g, 8.6% yield).

NMR(CDCl$_3$) δ: 1.97(1H,m), 2.52(1H,m), 3.12(1H,m), 3.32(1H,m), 3.72(3H,s), 3.75(2H,s), 3.81(3H,s), 3.95(1H,m), 4.33(1H,m), 4.60(2H,m), 5.26(2H,m), 5.90(1H,m), 6.88(2H,d,J=8 Hz), 7.24(2H,d,J=8 Hz)

REFERENCE EXAMPLE 2-3)

2S,4S)-N-Allyloxycarbonyl-2-hydroxymethyl-4-(p-methoxybenzylthio)pyrrolidine

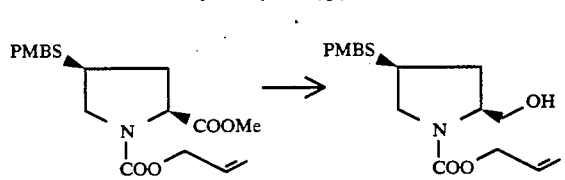

To a solution of (2S,4S)-N-allyloxycarbonyl-4-(p-methoxybenzylthio)proline methyl ester (the compound obtained in Reference Example 2-2); 4.64 g, 12.7 mmol) in tetrahydrofuran (50 ml), were successively added lithium chloride (1.08 g, 25.5 mmol), sodium borohydride (960 mg, 25.4 mmol) and ethanol (50 ml) and the reaction mixture was stirred overnight at room temperature. After being quenched by careful addition of acetic acid (5.8 ml, 101.3 mmol), the mixture was concentrated, and extracted with ethyl acetate (200 ml). The organic layer was washed with saturated sodium chloride, dried over anhydrous sodium sulfate and concentrated in vacuo. The residue was purified by silica gel column chromatography (Wakogel ® C-300, elution with hexane-ethyl acetate 3:1) to give the title compound (3.72 g, 86.8% yield).

NMR(CDCl$_3$) δ: 2.33(1H,m), 2.96–3.22(2H,m), 3.66–3.74(4H,m), 3.82(3H,s), 3.95(2H,m), 4.60(2H,d,J=6 Hz), 5.30(2H,m), 5.95(1H,m), 6.86(2H,d,J=8 Hz), 7.24(2H,d,J=8 Hz)

REFERENCE EXAMPLE 2-4)

(E)-3-[(2S,4S)-N-Allyloxycarbnyl-4-(p-methoxybenzyl-thio)pyrrolidin-2-yl]-2-methylacrylamide

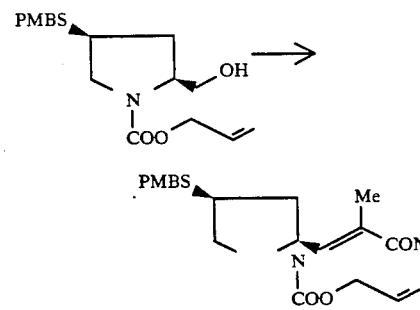

To a solution of oxalyl chloride (0.54 ml, 6.3 mmol) in methylene chloride (20 ml) was dropwise added a solution of dimethyl sulfoxide (0.67 ml, 9.4 mmol) in methylene chloride (5 ml) under nitrogen at −78° C. The reaction mixture was stirred at −78° C. for 20 minutes, treated dropwise with a solution of (2S,4S)-N-allyloxycarbonyl-2-hydroxymethyl-4-(p-methoxybenzylthio)-pyrrolidine (the compound obtained in Reference Example 2-3); 1.5 g, 4.45 mmol) in methylene chloride (10 ml) at the same temperature, and stirred for 30 minutes. The mixture was treated with triethylamine (2.04 ml, 14.7 mmol), stirred for 30 minutes at −78° C., extracted with methylene chloride (100 ml), and the organic layer washed successively with dil. hydrochloric acid, water and saturated aqueous sodium chloride, dried over anhydrous magnesium sulfate, and concentrated to give the crude product containing (2S,4S)-N-allyloxycarbonyl-2-formyl-4-(p-methoxybenzylthio)pyrrolidine.

To a mixture of sodium hydride (200 mg, 5.0 mmol, 60% dispersion in mineral oil) in tetrahydrofuran (15 ml) was dropwise added diethyl 1-aminocarbonylethyl phosphonate (1.07 g, 5.1 mmol) under ice-cooling under nitrogen and the reaction mixture stirred for 20 minutes, treated with the crude 2-formyl compound, obtained in the previous reaction, in tetrahydrofuran (10 ml), stirred for 1 hour, and extracted with ethyl acetate (50 ml). The organic layer was washed successively with water and saturated aqueous sodium chloride, dried over anhydrous magnesium sulfate, and concentrated in vacuo. The residue was purified by silica gel column chromatography (Wakogel® C-300, elution with 1% methanol-chloroform) to give the title compound (990 mg, 57% yield).

NMR(CDCl₃) δ: 1.88(3H,br s), 2.42(1H,m), 3.02–3.44(3H,m), 3.72(2H,s), 3.79(3H,s), 4.44–4.75(3H,m), 5.25(2H,m), 5.92(3H,m), 6.28(1H,m), 6.85(2H,d,J=8 Hz), 7.22(2H,d,J=8 Hz)

REFERENCE EXAMPLE 3

(Z)-3-[(2S,4S)-N-AllyloxycarbonVl-4-tritylthiopyrrolidin-2-yl]acrylamide

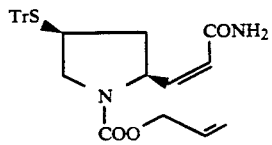

REFERENCE EXAMPLE 3-1)

(2S,4S)-N-Allyloxycarbonyl-2-hydroxymethyl-4-tritylthiopyrrolidine

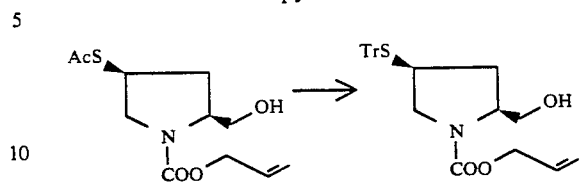

To a solution of (2S,4S)-4-acetylthio-N-allyloxycarbonyl-2-hydroxymethylpyrrolidine (the compound obtained in Reference Example 1-5); 111.1 g, 428 mmol) in methanol (1.1 l) was added 2N sodium hydroxide (225 ml) under ice-cooling. The reaction mixture was stirred under ice-cooling for 30 minutes, and 6N hydrochloric acid (78.5 ml), saturated aqueous sodium chloride (700 ml) and water (300 ml) were successively added, and the mixture was extracted with ethyl acetate (1 l and 250 ml×2). The combined organic layer was washed with saturated aqueous sodium chloride (500 ml×2), dried over anhydrous sodium sulfate, and concentrated in vacuo. The residue was dissolved in N,N-dimethylformamide (420 ml), treated with tritylchloride (118.8 g, 426 mmol), and the reaction mixture was stirred for 4 hours at 70° C. After cooling to room temperature, the mixture was diluted with water (1 l), extracted with ethyl acetate (1 and 250 ml×2). The combined organic layer was washed successively with saturated aqueous sodium bicarbonate (500 ml) and saturated aqueous sodium chloride (500 ml), dried over anhydrous sodium sulfate, and concentrated in vacuo. The residue was purified by flash column chromatography on silica gel (Wakogel® C-300, 1.2 l, elution with ethyl acetate-hexane 1:1) to give the title compound (115.3 g, 58.5% yield).

NMR(CDCl₃) δ: 1.35(1H,m), 1.95(1H,m), 2.65–3.1(3H,m), 3.5–3.8(3H,m), 4.45–4.7(3H,m), 5.2–5.3(2H,m), 5.9(1H,m), 7.2–7.6(15H,m)

REFERENCE EXAMPLE 3-2)

Methyl (Z)-3-[(2S,4S)-N-allyloxycarbonyl-4-tritylthiopyrrolidin-2-yl]acrylate

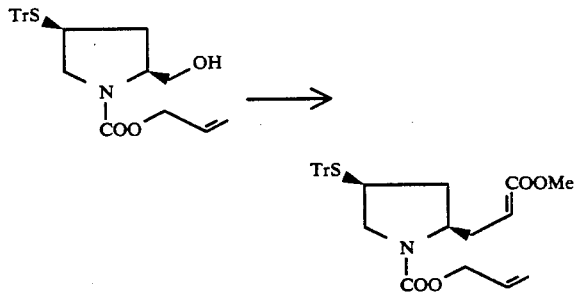

To a solution of oxalyl chloride (2.26 ml, 26.5 mmol) in methylene chloride (50 ml) was added dropwise a solution of dimethyl sulfoxide (3.05 ml, 42.9 mmol) in methylene chloride (10 ml) at −78° C. under nitrogen. After 20 minutes of stirring, treated with a solution of (2S,4S)-N-allyloxycarbonyl-2-hydroxymethyl-4-tritylthiopyrrolidine (the compound obtained in Reference Example 3-1); 8.67 g, 18.9 mmol) in methylene chloride was added at −78° C. (50 ml) thereto, and the mixture stirred there for 30 minutes. The resulting mixture was treated with triethylamine (9.39 ml, 67.5 mmol), stirred at −78° C. for 30 minutes, and extracted with methylene chloride (200 ml). The organic layer washed successively with 0.5N hydrochloric acid, water and saturated aqueous sodium chloride, dried over anhydrous magnesium sulfate, and concentrated to give the crude product containing (2S,4S)-N-allyloxycarbonyl-2-formyl-4-tritylthiopyrrolidine.

A solution of bis(2,2,2-trifluoroethyl)(methoxycarbonylmethyl)phosphonate (6.0 g, 18.9 mmol) and 18-crown-6 (24.96 g, 94.4 mmol) in tetrahydrofuran (250 ml) was treated dropwise successively with 0.5M potassium bis(trimethylsilyl)amide in toluene (37.7 ml) and the crude 2-formyl compound, obtained in the previous reaction, in tetrahydrofuran (50 ml) at −78° C. under nitrogen. After being for 30 minutes at −78° C., extracted with ethyl acetate (300 ml), and the organic layer washed successively with water and saturated aqueous sodium chloride, dried over anhydrous magnesium chloride, and concentrated. The residue was purified by silica gel column chromatography (Wakogel® C-300, elution with 10% hexane-ethyl acetate 9:1) to give the title compound (7.8 g, 80.8% yield).

NMR(CDCl₃) δ: 1.52(1H,m), 2.42(1H,m), 3.68(3H,s), 4.48(2H,m), 5.18(2H,m), 5.80(2H,m), 6.16(1H,m), 7.18-7.58(15H,m)

REFERENCE EXAMPLE 3-3)

(Z)-3-[(2S,4S)-N-Allyloxycarbonyl-4-tritylthiopyrrolidin-2-ylthio]acrylic acid

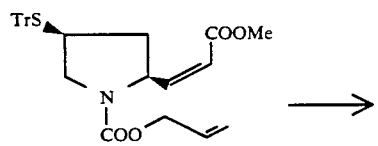

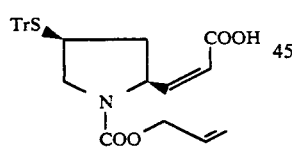

A solution of methyl (Z)-3-[(2S,4S)-N-allyloxycarbonyl-4-tritylthiopyrrolidin-2-ylthio]acrylate (the compound obtained in Reference Example 3-2); 1.38 g, 2.7 mmol) in methanol (50 ml) was treated with 1N sodium hydroxide (4.1 ml), and the mixture stirred for 2 days at 30°–40° C. After the addition of 1N hydrochloric acid (4.1 ml), the mixture was concentrated in vacuo, and extracted with ethyl acetate (100 ml). The organic layer was washed with saturated aqueous sodium chloride, dried over anhydrous magnesium sulfate, and concentrated. The residue was purified by silica gel column chromatography (Wakogel® C-300, elution with 1% MeOH/CHCl₃) to give the title compound (1.06 g, 79% yield).

NMR(CDCl₃) δ: 1.47(1H,m), 2.34(1H,m), 4.50(2H,m), 4.95-5.32(3H,m), 5.85(2H,m), 6.18(1H,m), 7.18-7.66(15H,m)

REFERENCE EXAMPLE 3-4)

(Z)-3-[(2S,4S)-N-Allyloxycarbonyl-4-tritylthiopyrrolidin-2-yl]acrylamide

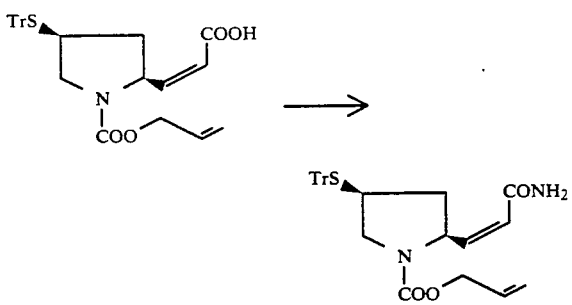

A solution of (Z)-3-[(2S,4S)-N-allyloxycarbonyl-4-tritylthiopyrrolidin-2-yl]acrylic acid (the compound obtained in Reference Example 3-3); 664 mg, 1.34 mmol) in tetrahydrofuran (10 ml) was treated with triethylamine (0.23 ml, 1.65 mmol) and isobutyl chloroformate (0.22 ml, 1.7 mmol) at −20° C. under nitrogen, and the mixture stirred for 30 minutes. The reaction mixture was treated with conc. aqueous ammonia (0.2 ml, 3.0 mmol) at −20° C., stirred there for 20 minutes, and extracted with ethyl acetate (100 ml), and the organic layer was washed successively with water and saturated aqueous sodium chloride, dried over anhydrous magnesium sulfate, and concentrated in vacuo. The residue was purified by silica gel column chromatography (Wakogel® C-300, elution with CHCl₃) to give the title compound (623 mg, 94% yield).

IR(KBr)cm⁻¹: 1680, 1600, 1400, 1110, 740, 700

NMR(CDCl₃) δ: 1.53(1H,m), 2.28(1H,m), 2.72-2.95(3H,m), 4.48(2H,m), 4.72(1H,m), 5.25(2H,m), 5.58-5.98(4H,m), 7.18-7.64(15H,m)

REFERENCE EXAMPLE 4

(E)-3-[(2S,4S)-N-Allyloxycarbonyl-4-mercaptopyrrolidin-2-yl]acrylamide

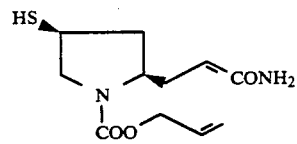

REFERENCE EXAMPLE 4-1)

(E)-3-[(2S,4S)-N-Allyloxycarbonyl-4-tritylthiopyrrolidin-2-yl]acrylamide

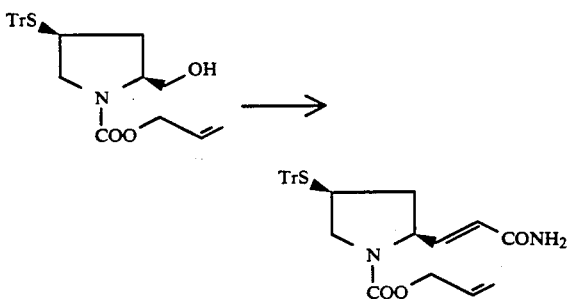

To a solution of dimethyl sulfoxide (49.9 ml, 703 mmol) in methylene chloride (1.1 l) was added oxalyl chloride (32.1 ml, 376 mmol) at −70° C., and the reaction mixture stirred for 30 minutes, treated with a precooled (−70° C.) solution of (2S,4S)-N-allyloxycarbonyl-2-hydroxymethyl-4-tritylthiopyrrolidine(115.3 g, 251 mmol) in methylene chloride (400 ml), and stirred for 30 minutes. The mixture was treated with triethylamine (174.9 ml, 1.25 mol), stirred for 30 minutes, and stirred for additional 30 minutes after removing an ice-bath. The mixture was poured into water (500 ml), the organic layer washed with 1M sodium dihydrogen phosphate (500 ml) and saturated sodium bicarbonate, dried over anhydrous sodium sulfate, and concentrated in vacuo. A solution of the obtained residue and 2-(diethylphosphono)acetamide (63.6 g, 326 mmol) in tetrahydrofuran (1.6 l) was treated with 60% sodium hydride (11 g, 275 mmol) under ice-cooling, and the reaction mixture stirred for 30 minutes, and concentrated. The residue was dissolved in ethyl acetate (1.5 l), washed successively with water (1 l and 500 ml) and saturated aqueous sodium chloride, dried over anhydrous sodium sulfate, and concentrated. The residual solid was collected by filtration after addition of diisopropyl ether (600 ml), recrystallized from a mixture of ethyl acetate (700 ml) and hexane (700 ml) to give the title compound (79.2 g), and the mother liquor was purified by flash column chromatography on silica gel (Wakogel ® C-300, 400 ml, elution with ethyl acetate) to give a second crop (combined weight 89.4 g, 71.5% total yield).

NMR(CDCl₃) δ: 1.54(1H,m), 2.1(1H,m), 2.7–3.4(3H,m), 4.18(1H,q,J=8 Hz), 4.3–4.5(2H,m), 5.1–5.3(2H,m), 5.42(2H,brs), 5.7–5.9(2H,m), 6.62(1H,dd,J=8,15 Hz), 7.2–7.6(15H,m)

REFERENCE EXAMPLE 4-2)

(E)-3-[(2S,4S)-N-Allyloxycarbonyl-4-mercaptopyrrolidin-2-yl]acrylamide

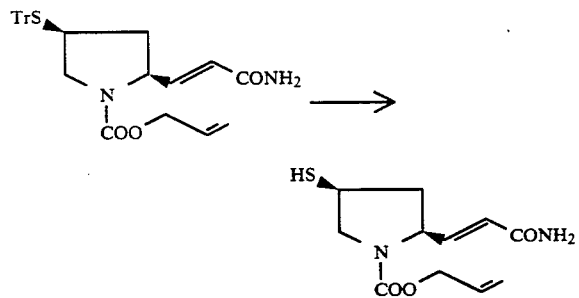

To a suspension of (E)-3-[(2S,4S)-N-allyloxycarbonyl 4-tritylthiopyrrolidin-2-yl]acrylamide (60 g, 120 mmol) in methylene chloride (60 ml) were added trifluoroacetic acid (60 ml) and triethylsilane (20 ml, 125 mmol) under ice-cooling. The reaction mixture was stirred under icecooling for 10 minutes and for additionally 30 minutes at room temperature, and concentrated. The residue was dissolved in methylene chloride (100 ml), and the solution concentrated. The obtained residue was dissolved ethyl acetate (750 ml), and the solution washed with 1M sodium phosphate buffer (pH 5.5, 500 ml and 250 ml×3) and saturated sodium chloride, dried over anhydrous sodium sulfate, and concentrated. The residue was dissolved in ethyl acetate (50 ml), treated with hexane (250 ml) to crystallize to give the title compound (30 g, 97.3% yield).

NMR(CDCl₃) δ: 1.75(2H,m), 2.65(1H,m), 3.2–3.4(2H,m), 4.1(1H,brs), 4.45–4.6(3H,m), 5.2–5.4(2H,m), 5.7–6.1(4H,m), 6.80(1H,dd,J=7,15 Hz)

REFERENCE EXAMPLE 5

(E)-3-[(2S,4S)-N-Allyloxycarbonyl-4-mercaptopyrrolidin-2-yl]-N-methylacrylamide

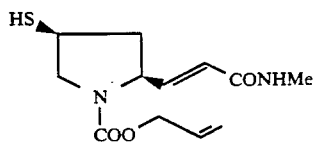

REFERENCE EXAMPLE 5-1)

(E)-3-[(2S,4S]-N-Allyloxycarbonyl-4-tritylthiopyrrolidin-2-yl]-N-methylacrylamide

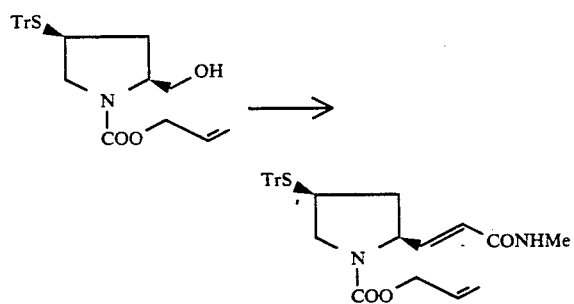

The same operation as in Reference Example 4–1) was carried out by using (2S,4S)-N-allyloxycarbonyl-2-hydroxymethyl-4-tritylthiopyrrolidine (the compound obtained in the Reference Example 3-1); 4.60 g, 10.0 mmol), dimethyl sulfoxide (1.99 ml, 28.0 mmol), oxalyl chloride (1.28 ml, 15.0 mmol), triethylamine (6.98 ml, 50.0 mmol), 2-(diethylphosphono)-N-methylacetamide (2.32 g, 11.0 mmol) and 60% sodium hydride (420 mg, 10.5 mmol), followed by flash column chromatographic purification on silica gel (Wakogel ® C-300, 100 ml, elution with hexaneethyl acetate 1:2) to give the title compound (4.60 g, 89.7% yield).

NMR(CDCl₃) δ: 1.56(1H,m), 2.08(1H,m), 2.8(3H,d,J=4 Hz), 2.7–3.4(3H,m), 4.16(1H,q,J=7 Hz), 4.44(2H,m), 5.2(2H,m), 5.5–5.9(3H,m), 6.6(1H,ml, 7.1–7.5(15H,m)

REFERENCE EXAMPLE 5-2)

(E)-3-[(2S,4S)-N-Allyloxycarbonyl-4-mercaptopyrrolidin-2-yl]-N-methylacrylamide

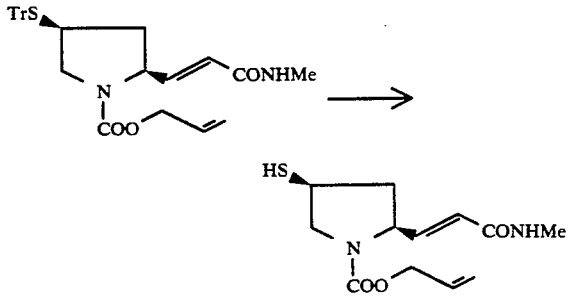

The same operation as in Reference Example 4-2) was carried out by using (E)-3-[(2S,4S)-N-allyloxycarbonyl-4-tritylthiopyrrolidin-2-yl]-N-methylacrylamide (the compound obtained in Reference Example 5-1); 1.54 g, 3 mmol) and triethylsilane (0.49 ml, 3.15 mmol), followed by flash column chromatographic purification on silica gel (Wakogel® C-300, 40 ml, elution with acetone-methylene chloride 1:1) to give the title compound (620 mg, 76.3% yield).

NMR(CDCl$_3$) δ: 1.73(1H,d,J=6 Hz), 1.77(1H,m), 2.65(1H,m), 2.86(3H,d,J=6 Hz), 3.1-3.4(2H,m), 4.1(1H,m), 4.47(1H,q,J=7 Hz), 4.56(2H,brd,J=6 Hz), 5.2-5.4(2H,m), 5.7(1H,brs), 5.8-6.0(2H,m), 6.75(1H,m)

REFERENCE EXAMPLE 6

(E)-3-[(2S,4S)-N-Allyloxycarbonyl-4-mercaptopyrrolidin-2-yl]-N,N-dimethylacrylamide

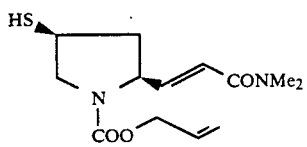

REFERENCE EXAMPLE 6-1)

(E)-3-[(2S,4S)-N-Allyloxycarbonyl-4-tritylthiopyrrolidin-2-yl]-N,N-dimethylacrylamide

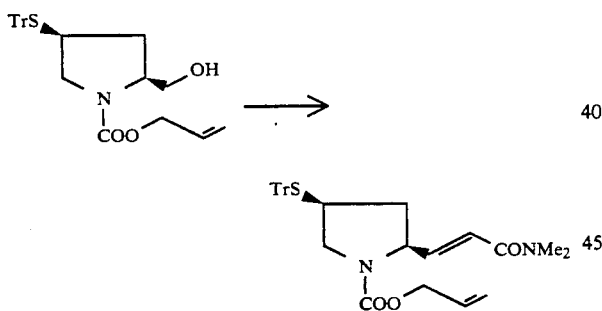

The same operation as in Reference Example 4-1) was carried out by using (2S,4S)-N-allyloxycarbonyl-2-hydroxymethyl-4-tritylthiopyrrolidine (the compound obtained in Reference Example 3-1); 2.00 g, 4.35 mmol), dimethyl sulfoxide (0.87 ml, 12.2 mmol), oxalyl chloride (0.56 ml, 6.5 mmol), triethylamine (3.03 ml, 21 8 mmol), 2-(diethylphosphono)-N,N-dimethylacetamide (1.17 g, 5.22 mmol) and 60% sodium hydride (174 mg, 4.35 mmol), followed by flash column chromatographic purification on silica gel (Wakogel® C-300, 40 ml, elution with hexane-ethyl acetate 1 1) to give the title compound (2.02 g, 88.1% yield)

NMR(CDCl$_3$) δ: 1.6(1H,m), 2.1(1H,m), 2.7-3.4(3H,m), 2.96(3H,s), 3.0(3H,s), 4.18(1H,q,J=7 Hz), 4.46(2H,m), 5.1-5.3(2H,m), 5.82(1H,m), 6.28(1H,m), 6.6(1H,m), 7.1-7.5(15H,m)

REFERENCE EXAMPLE 6-2)

(E)-3-[(2S,4S)-N-Allyloxycarbonyl-4-mercaptopyrrolidin-2-yl]-N,N-dimethylacrylamide

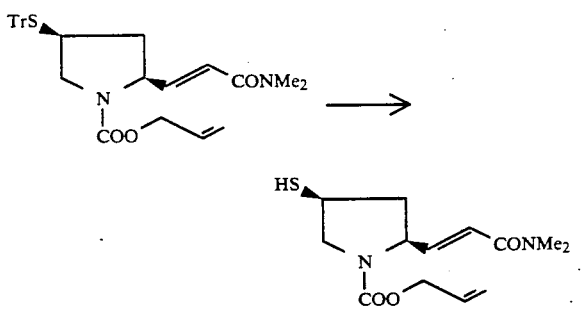

The same operation as in Reference Example 4-2) was carried out by using (E)-3-[(2S,4S)-N-allyloxycarbonyl-4-tritylthiopyrrolidin-2-yl]-N,N-dimethylacrylamide (the compound obtained in Reference Example 6-1); 2.02 g, 3.84 mmol) and triethylsilane (0.64 ml, 4.03 mmol), followed by flash column chromatographic purification on silica gel (Wakogel® C-300, 40 ml, elution with acetone-methylene chloride 1:1) to give the title compound (980 mg, 89.9% yield).

NMR(CDCl$_3$) δ: 1.73(1H,d,J=7 Hz), 1.76(1H,m), 3.0(3H,s), 3.06(3H,s), 3.1-3.4(2H,m), 4.1(1H,m), 4.49(1H,q,J=8 Hz), 4.58(2H,m), 5.15-5.35(2H,m), 5.9(1H,m), 6.36(1H,m), 6.74(1H,m)

REFERENCE EXAMPLE 7

(2S,4S]-N-Allyloxycarbonyl-4-mercapto-2-[(E)-(2-oxopyrrolidin-3-ylidene)methyl]pyrrolidine and its (Z)-isomer

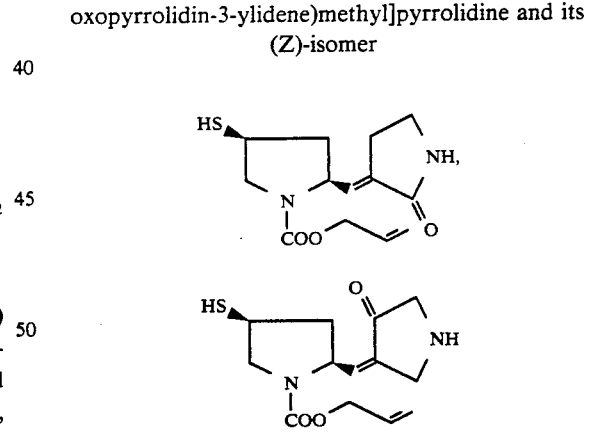

REFERENCE EXAMPLE 7-1)

(2S,4S)-N-Allyloxycarbonyl-2-[(E)-(2-oxopyrrolidin-3-ylidene)methyl]-4-tritylthiopyrrolidine and its (Z)-isomer

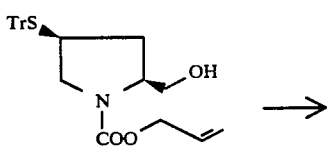

-continued

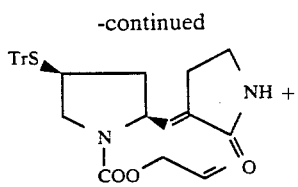

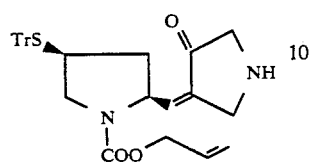

The same operation as in Reference Example 4-1) was carried out by using (2S,4S)-N-allyloxycarbonyl-2-hydroxymethyl-4-tritylthiopyrrolidine (the compound obtained in Reference Example 3-1); 11.12 g, 24.2 mmol), dimethyl sulfoxide (4.81 ml, 67.7 mmol), oxalyl chloride 3-(diethylphosphono)-2-oxopyrrolidine (5.35 g, 24.2 mmol) and 60% sodium hydride (870 mg, 21.8 mmol), followed by flash column chromatographic purification on silica gel (Wakogel® C-300, 100 ml, elution with hexane-ethyl acetate 1:1 - ethyl acetate) to give the title compounds ((Z)-form 2.72 g, 21.4% yield; (E)-form 5.15 g, 40.6 % yield).

(Z)-form
NMR(CDCl₃) δ: 1.55(1H,m), 2.4–3.2(5H,m), 3.37(2H,t,J=5 Hz), 4.3–4.6(3H,m), 5.1–5.3(2H,m), 5.5(1H,m), 5.7–5.9(2H,m), 6.25(1H,m), 7.2–7.7(15H,m)

(E)-form
NMR(CDCl₃) δ: 1.55(1H,m), 2.1(1H,m), 2.6–3.1(5H,m), 3.4(2H,m), 4.15(1H,m), 4.45(2H,m), 5.2(2H,m), 5.8(1H,m), 6.2(1H,brs), 6.45 and 6.6 (total 1H, each brs), 7.2–7.6(15H,m)

REFERENCE EXAMPLE 7-2)

(2S,4S]-N-Allyloxycarbonyl-4-mercapto-2-[(E)-(2-oxopyrrolidin-3-Ylidene)methyl]pyrroidine

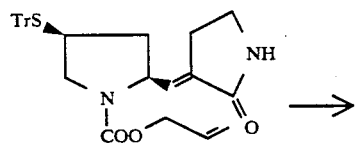

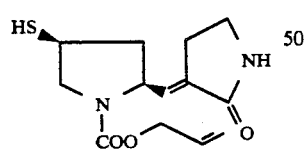

The same operation as in Reference Example 4-2) was carried out by using (2S,4S)-N-allyloxycarbonyl-2-[(E)-(2-oxopyrrolidin-3-ylidene)methyl]-4-tritylthiopyrrolidine (the compound obtained in Reference Example 7-1) ((E)-form); 6.80 g, 12.96 mmol) and triethylsilane (2.17 ml, 13.6 mmol), followed by flash column chromatographic purification on silica gel (Wakogel® C-300, 40 ml, elution with acetone-methylene chloride 1:1) to give the title compound (3.02 g, 82.5% yield).

NMR(CDCl₃) δ: 1.7(2H,m), 2.6–2.9(2H,m), 3.1–3.5(5H,m), 4.1(1H,brs}, 4.4–4.6(3H,m), 5.2–5.4(2H,m), 5.9(1H,m), 6.4(1H,m), 6.6 and 6.8 (total 1H, each brs).

REFERENCE EXAMPLE 7-3)

(2S,4S]-N-Allyloxycarbonyl-4-mercapto-2-[(Z)-(2-oxopyrrolidin-3-ylidene)methyl]pyrrolidine

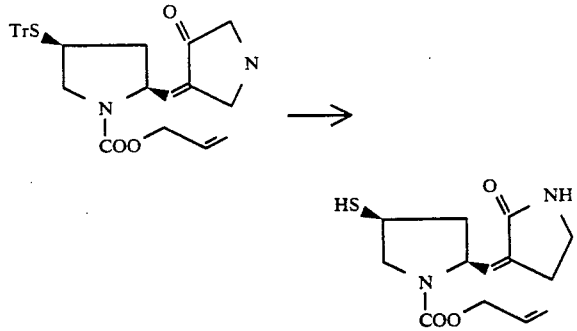

The same operation as in Reference Example 4-2) was carried out by using (2S,4S)-N-allyloxycarbonyl-2-[(Z)-(2-oxopyrrolidin-3-ylidene)methyl]-4-tritylthiopyrrolidine (the compound obtained in Reference Example 7-1) ((Z) form); 2.00 g, 3.81 mmol) and triethylsilane (0.64 ml, 4.00 mmol), followed by flash column chromatographic purification on silica gel (Wakogel® C-300, 40 ml, elution with acetone-methylene chloride 1:1) to give the title compound (844 mg, 78.4% yield).

NMR(CDCl₃) δ: 1.7(2H,m), 2.7–2.9(3H,m), 3.2–3.5(4H,m), 4.0(1H,m), 4.6(2H,m), 5.1–5.4(2H,m), 5.7–6.0(4H,m)

REFERENCE EXAMPLE 8

(2S,4S}-N-Allyloxycarbonyl-2-[(E)-2-[4-(allyloxycarbonyl)piperazinylcarbonyl]vinyl]-4-mercaptopyrrolidine

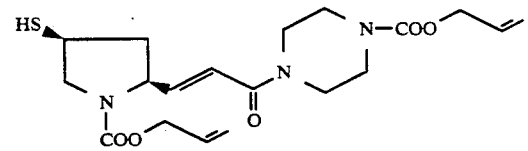

REFERENCE EXAMPLE 8-1)

(2S,4S]-N-Allyloxycarbonyl-2-[(E)-2-[4-(allyloxycarbonyl)piperazinylcarbonyl]vinyl]-4-tritylthiopyrrolidine

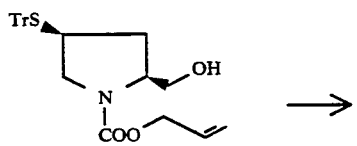

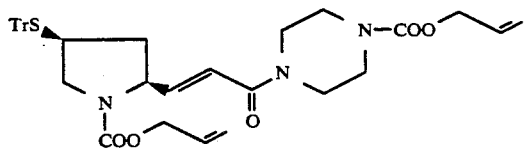

The same operation as in Reference Example 4-1) was carried out by using (2S,4S)-N-allyloxycarbonyl-2-hydroxymethyl-4-tritylthiopyrrolidine (the compound obtained in Reference Example 3-1); 1.5 g, 3.26 mmol), dimethyl sulfoxide (0.65 ml, 9.14 mmol), oxalyl chloride (0.42 ml, 4.90 mmol), triethylamine (2 ml, 14.9 mmol), N-allyloxycarbonyl-N'-(diethylphosphonoacetyl)piperazine (1.24 g, 3.92 mmol) and 60% sodium hydride (130 mg, 3.26 mmol), followed by flash column chromatographic purification on silica gel (Wakogel ® C-300, 40 ml, elution with ethyl acetate) to give the title compound (1.97 g, 92.6% yield).

NMR(CDCl$_3$) δ: 1.6(1H,m), 2.1(1H,m), 2.7-3.2(3H,m), 3.4-3.7(8H,m), 4.2(1H,m), 4.5(2H,br s), 4.62(2H,d,J=5 Hz), 5.1-5.4(4H,m), 5.8-6.0(2H,m), 6.26(1H,d,J=15 Hz), 6.6(1H,m), 7.2-7.6(15H,m)

REFERENCE EXAMPLE 8-2)

(2S,4S)-N-Allyloxycarbonyl-2-[(E)-2-[4-(allyloxycarbonyl)piperazinylcarbonyl]vinyl]-4-mercaptopyrrolidine

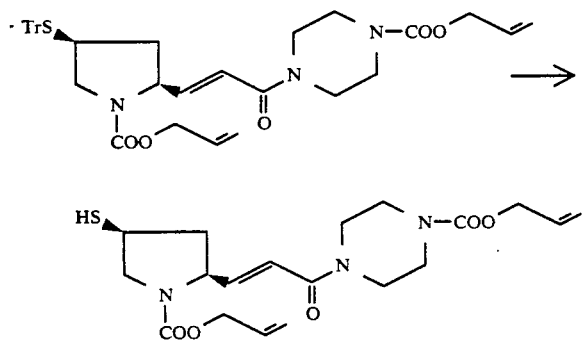

The same operation as in Reference Example 4-2) was carried out by using (2S,4S)-N-allyloxycarbonyl-2-[(E)-2-[4-(allyloxycarbonyl)piperazinylcarbonyl]vinyl]-4-tritylthiopyrrolidine (the compound obtained in Reference Example 8-1); 1.97 g, 3.02 mmol) and triethylsilane (0.51 ml, 3.17 mmol), followed by flash column chromatographic purification on silica gel (Wakogel ® C-300, 40 ml, elution with acetone-ethyl acetate 1:2) to give the title compound (1.24 g, 100% yield) as an oil.

NMR(CDCl$_3$) δ: 1.7(2H,m), 2.6(1H,m), 3.2-3.7(10H,m), 4.1(1H,m), 4.4-4.7(5H,m), 5.1-5.4(4H,m), 5.9(2H,m), 6.3(1H,d,J=15 Hz), 6.7(1H,m)

REFERENCE EXAMPLE 9

Allyl (5R,6S)-2-[(2S,4S)-N-allyloxycarbonyl-2-hydroxymethylpyrrolidin-4-ylthio]-6-[(R)-1-allyloxycarbonyloxyethyl]-1-carbapen-2-em-3-carboxylate

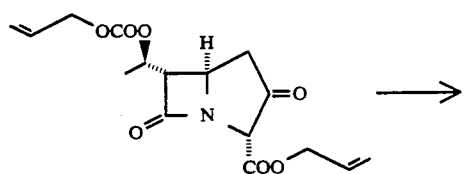

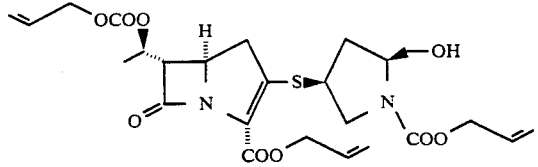

To a solution of allyl (3R,5R,6S)-6-[(R)-1-allyloxycarbonyloxyethyl]-2-oxo-1-carbapenam-3-carboxylate (1.01 g, 3 mmol) and N,N-diisopropylethylamine (0.73 ml, 4.2 mmol) in acetonitrile (20 ml) was dropwise added diphenyl chlorophosphate (0.75-3.6 mmol) under ice-cooling, and then the mixture stirred for 30 minutes. The reaction mixture under ice-cooling was treated successively with N,N-diisopropylethylamine (0.73 µl, 4.2 mmol) and (2S,4S)-N-allyloxycarbonyl-2-hydroxymethyl-4-mercaptopyrrolidine (780 mg, 3.6 mmol) in acetonitrile (4 ml), stirred for 1 hour, and partitioned between ethyl acetate (60 ml) and water (40 ml). The organic layer was successively washed with saturated aqueous sodium bicarbonate and saturated aqueous sodium chloride, dried over anhydrous sodium sulfate, concentrated, and the residue purified by flash column chromatography on silica gel (Wakogel ® C-300, 40 ml, elution with ethyl acetate-hexane 1:1) to afford the title compound (1.20 g, 75% yield).

NMR(CDCl$_3$) δ: 1.46(3H,d,J=6 Hz), 2.5(2H,m), 3.1-3.4(4H,m), 3.55(1H,t,J=7 Hz), 3.75(2H,brs), 4.0-4.3(4H,m), 4.7(6H,m), 5.15(1H,m), 5.2-5.5(6H,m), 6.0(3H,m)

REFERENCE EXAMPLE 10

Allyl (1R,5S,6S)-2-[(2S,4S)-N-allyloxycarbonyl-2-hydroxymethylpyrrolidin-4-ylthio]-6-[(R)-1-allyloxycarbonyloxyethyl]-1-methyl-1-carbapen-2-em-3-carboxylate

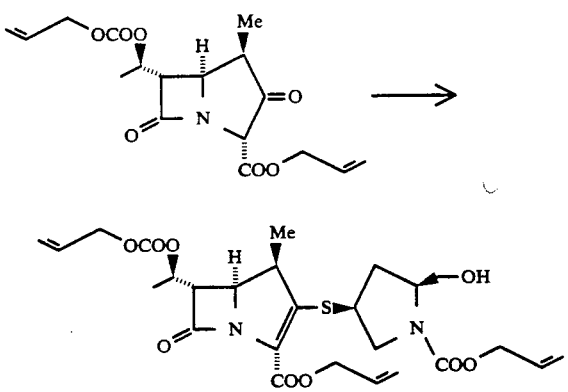

The same operation as in Reference Example 9 was carried out by using allyl (1R,3R,5S,6S)-6-[(R)-1-allyloxycarbonyloxyethyl]-1-methyl-2-oxo-1-carbapenam-3-carboxylate (700 mg, 2 mmol) and (2S,4S)-N-allyloxycarbonyl-2-hydroxymethyl-4-mercaptopyrrolidine (the compound obtained in Reference Example 1; 470 mg, 1.8 mmol) to obtain the title compound (410 mg, 37% yield).

NMR(CDCl$_3$) δ: 1.28(3H,d,J=7 Hz), 1.48(3H,d,J=7 Hz), 1.7(1H,m), 2.5(1H,m), 2.35(3H,m), 2.6(1H,m), 2.75(2H,d,J=5 Hz), 3.9–4.3(3H,m), 4.6–4.9(6H,m), 5.15(1H,m), 5.2–5.5(6H,m), 5.95(3H,m)

We claim:

1. A compound of the formula:

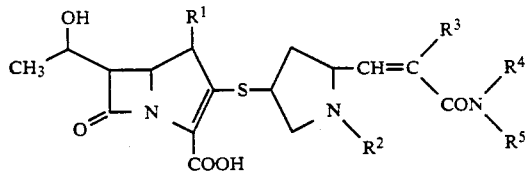

wherein $R^1$ is a hydrogen atom or a methyl group, $R^2$ is a hydrogen atom or a lower alkyl group, each of $R^3$, $R^4$ and $R^5$ is a hydrogen atom or a lower alkyl group, or $R^3$ and $R^4$ together form a methylene group, an ethylene group or a propylene group, or $R^4$ and $R^5$ form together with the adjacent nitrogen atom an aziridinyl group, an azetidinyl group, a pyrrolidinyl group, a piperidino group, a piperazinyl group or a morpholino group; or a pharmaceutically acceptable salt or ester thereof.

2. The compound according to claim 1, wherein $R^2$ is a methyl group.

3. The compound according to claim 1, wherein each of $R^2$ and $R^3$ is a hydrogen atom.

4. The compound according to claim 1, wherein $R^3$ and $R^4$ together form a methylene group, an ethylene group or a propylene group.

5. The compound according to claim 1, wherein at least one of $R^4$ and $R^5$ is a hydrogen atom.

6. The compound according to claim 1, wherein $R^4$ and $R^5$ form together with the adjacent nitrogen atom an aziridinyl group, an azetidinyl group, a pyrrolidinyl group, a piperidino group, a piperazinyl group or a morpholino group.

7. The compound according to claim 1, wherein the steric configuration of the compound of the formula (I) is (5R,6S,8R) or (1R,5S,6S,8R).

8. The compound according to claim 1, wherein the stereoisomer at the double bond of the compound of the formula (I) is an (E)-isomer.

9. The compound according to claim 1, which is: (5R,6S)-2 [(2S,4S)-2-[(E)-2-(aminocarbonyl)vinyl]pyrrolidin-4-ylthio]-6-[(R)-1-hydroxyethyl]-1-carbapen-2-em-3-carboxylic acid, (5R,6S)-2-[(2S,4S)-2-[(E)-2-(N,N-dimethylaminocarbonyl)vinyl]pyrrolidin-4-ylthio]-6-[(R)-1-hydroxyethyl]-1-carbapen-2-em-3-carboxylic acid, (1R,5S,6S)-2-[(2S,4S)-2-[(E)-2-(aminocarbonyl)vinyl]pyrrolidin-4-ylthio]-6-[(R)-1hydroxyethyl]-1-methyl-1-carbapen-2-em-3-carboxylic acid, (1R,5S,6S)-2-[(2S,4S)-2-[(Z)-2-(aminocarbonyl)vinyl]pyrrolidin-4-ylthio]-6-[(R)-1-hydroxyethyl]-1-methyl-1-carbapen-2-em-3-carboxylic acid, (1R,5S,6S)-2-[(2S,4S)-2-[(E)-2-(N,N-dimethylaminocarbonyl)vinyl]pyrrolidin-4-ylthio]-6-[(R)-1-hydroxyethyl]-1-methyl-1-carbapen-2-em-3-carboxylic acid, (5R,6S)-2-[(2S,4S)-2-[(E)-2-(aminocarbonyl)-2-methylvinyl]pyrrolidin-4-ylthio]-6-[(R)-1-hydroxyethyl]-1-carbapen-2-em-3-carboxylic acid, (1R,5S,6S)-2-[(2S,4S)-2-[(E)-2-(aminocarbonyl)-2-methylvinyl]pyrrolidin-4-ylthio]-6-[(R)-1-hydroxyethyl]-1-methyl-1-carbapen-2-em-3-carboxylic acid, (5R,6S)-6-[(R)-1-hydroxyethyl]-2-[(2S,4S)-2-[(E)-2-(N-methylaminocarbonyl)vinyl]pyrrolidin-4-ylthio]-1-carbapen-2-em-3-carboxylic acid, (1R,5S,6S)-6-[(R)-1-hydroxyethyl]-1-methyl-2-[(2S,4S)-2[-(E)-2-(N-methylaminocarbonyl)vinyl]pyrrolidin-4-ylthio]-1-carbapen-2-em-3-carboxylic acid, (5R,6S)-6-[(R)-1-hydroxyethyl]-2-[(2S,4S)-2-[(E)-(2-oxopyrrolidin-3-ylidene)-methyl]pyrrolidin-4-ylthio]-1-carbapen-2-em-3-carboxylic acid, (1R,5S,6S)-6-[(R)-1-hydroxyethyl]-1-methyl-2-[(2S,4S)-2[-(E)-(2-oxopyrrolidin-3-ylidene)-methyl]pyrrolidin-4-ylthio]-1-carbapen-2-em-3-carboxylic acid, (1R,5S,6S)-6-[(R)-1-hydroxyethyl]-1-methyl-2-[(2S,4S)-2[(Z)-(2-oxopyrrolidin-3-ylidene)methyl]pyrrolidin-4-ylthio]-1-carbapen-2-em-3-carboxylic acid or (1R,5S,6S)6-[(R)-1-hydroxyethyl]-1-methyl-2-[(2S,4S)-2-[(E)-2-pyrrolidin-4-ylthio]-1- carbapen-2-em-3-carboxylic acid.

10. The compound according to claim 1, which is (1R,5S,6S)-2-[(2S,4S)-2-[(E)-2-(aminocarbonyl)vinyl]-pyrrolidin-4-ylthio]-6-[(R)-1-hydroxyethyl]-1-methyl-1-carbapen-2-em-3-carboxylic acid or (1R,5S,6S)-6-[(R)-1-hydroxyethyl]-1-methyl-2-[(2S,4S)2-[(E)-(2-oxopyrolidin-3-ylidene)methyl]pyrrolidin-4-ylthio[-1-carbapen-2-em-3-carboxylic acid.

11. An antibacterial agent comprising an antibacterially effective amount of the compound of the formula (I) as defined in claim 1 or a pharmaceutically acceptable salt or ester thereof and a pharmaceutically acceptable carrier or diluent.

* * * * *